United States Patent
Miyake et al.

(10) Patent No.: US 12,405,258 B2
(45) Date of Patent: Sep. 2, 2025

(54) DIAGNOSIS DEVICE FOR ENVIRONMENTAL STRESS IN PLANTS AND ENVIRONMENTAL STRESS DIAGNOSIS METHOD

(71) Applicants: National University Corporation Kobe University, Kobe (JP); Bunkoukeiki Co., Ltd., Hachioji (JP)

(72) Inventors: Chikahiro Miyake, Kobe (JP); Takayuki Sohtome, Hachioji (JP)

(73) Assignees: National University Corporation Kobe University, Hyogo (JP); Bunkoukeiki Co., Ltd., Tokyo (JP)

( * ) Notice: Subject to any disclaimer, the term of this patent is extended or adjusted under 35 U.S.C. 154(b) by 225 days.

(21) Appl. No.: 18/036,857

(22) PCT Filed: Nov. 12, 2021

(86) PCT No.: PCT/JP2021/041742
§ 371 (c)(1),
(2) Date: May 12, 2023

(87) PCT Pub. No.: WO2022/102747
PCT Pub. Date: May 19, 2022

(65) Prior Publication Data
US 2023/0408478 A1    Dec. 21, 2023

(30) Foreign Application Priority Data
Nov. 12, 2020 (JP) .................. 2020-189009

(51) Int. Cl.
*G01N 33/00* (2006.01)
*A01G 7/04* (2006.01)
(Continued)

(52) U.S. Cl.
CPC ......... *G01N 33/0098* (2013.01); *A01G 7/045* (2013.01); *G01N 21/31* (2013.01);
(Continued)

(58) Field of Classification Search
None
See application file for complete search history.

(56) References Cited

U.S. PATENT DOCUMENTS 6,624,887 B1     9/2003 Kramer et al.
2005/0072935 A1* 4/2005 Lussier ............. G01N 21/6486
                                                  250/458.1
(Continued)

FOREIGN PATENT DOCUMENTS

JP    2005-326241 A    11/2005
JP       5881082 B2     3/2016
(Continued)

OTHER PUBLICATIONS

Aug. 29, 2018. Japanese Society of Soil Science and Plant Nutrition. Program of 2018 Kanagawa University Meeting. Session VII-6. Internet: <URL: https:// doi.org/10.20710/dohikouen.64.0_205>. p. 205. (Abstracts of the Annual Meetings. Japanese Society of Soil Science and Plant Nutrition). non-official translation (SEJIMA. Takehiro et al. Realization of Pulse Methods Intended for Inherent Reactive Oxygen Generation. Applications to Cultivation Environment Diagnosis: Practical Application of Reactive Oxygen (ROS) Diagnosis Based on P700 Oxidation System.) entire text. all drawings.

(Continued)

*Primary Examiner* — Marcus H Taningco
(74) *Attorney, Agent, or Firm* — Andrew F. Young, ESQ.; Nolte Lackenbach Siegel

(57) ABSTRACT

The present invention relates to an improved technology for a device that identifies and diagnoses an environmental
(Continued)

stress state of plants. A control circuit 20b controls a measurement light source 12 such that a second measurement light ML2 has higher power than a first measurement light ML1 and the first measurement light ML1 and the second measurement light ML2 become opposite-phase rectangular waves, and further controls the measurement light source 12 such that the first measurement light ML1 and the second measurement light ML2 are output in synchronization to form the first measurement light ML1 and the second measurement light ML2 into a quasi-single composite rectangular wave measurement light ML3 of 5 kHz to 30 kHz. A transmitted light detector 18 detects the composite rectangular wave measurement light ML3 transmitted through a plant sample S as a composite rectangular wave transmitted light TL. An analysis circuit 20a calculates a light absorption difference by utilizing the composite rectangular wave transmitted light TL, and calculates Y(ND) which is an oxidized state of P700 as a ROS marker utilizing the light absorption difference, and diagnoses an environmental stress state of plants by utilizing the ROS marker.

12 Claims, 94 Drawing Sheets

(51) Int. Cl.
  *G01N 21/31* (2006.01)
  *G01N 21/64* (2006.01)
  *G01N 21/84* (2006.01)
(52) U.S. Cl.
  CPC ......... *G01N 21/6486* (2013.01); *G01N 21/84* (2013.01); *G01N 2021/8466* (2013.01)

(56) References Cited

U.S. PATENT DOCUMENTS

| | | | |
|---|---|---|---|
| 2011/0179706 A1 | 7/2011 | Hunt | |
| 2015/0204787 A1* | 7/2015 | Kramer | G01N 21/6456 250/206 |
| 2018/0313760 A1* | 11/2018 | Kramer | G01N 21/6486 |

FOREIGN PATENT DOCUMENTS

| | | |
|---|---|---|
| JP | 2020-05034 A | 6/2020 |
| JP | 2020-95034 A | 6/2020 |

OTHER PUBLICATIONS

Furutani. R. et al. Chapter Five P700 oxidation suppresses the production of reactive oxygen species in photosystem I. Advances in Botanical Research. Sep. 1, 2020. vol. 96. pp. 151-176. Internet: <URL: https://doi.org/10.1016/bs.abr.2020.08.001> entire text. all drawings.

Mattila. H. et al. Singlet oxygen. flavonols and photoinhibition in green and senescing silver birch leaves. Trees. Mar. 16, 2021. vol. 35. pp. 1267-1282. Internet: <URL: https:// doi.org/10.1007/s00468-021-02114-x>, entire text, all drawings.

PCT/JP2021/041742, International Search Report and Written Opinion dated Feb. 1, 2022, 8 pages—Japanese, 6 pages—English.

Ru Zhang et al:"Photosynthetic electron transport and proton flux under moderate heat stress", Photosynthesis Research ; Official Journal of the International Society of Photosynthesis Research, Springer, Berlin, DE,vol. 100, No. 1, Apr. 3, 2009 (Apr. 3, 2009) , pp. 29-43.

Klughammer Christof et al:"Continuous ECS-indicated recording of the proton-motive charge flux in leaves", Photosynthesis Research, Springer Netherlands, Dordrecht, NL, vol. 117, No. 1,Jul. 17, 2013 (Jul. 17, 2013) , pp. 471-487.

Klughammer Christof et al:"Deconvolution of ferredoxin, plastocyanin, and P700 transmittance changes in intact leaves with a new type of kinetic LED array spectrophotometer", Photosynthesis Research, Springer Netherlands, Dordrecht, NL, vol. 128,No. 2,Feb. 2, 2016 (Feb. 2, 2016) , pp. 195-214.

Klughammer Christof et al: "Saturation Pulse method for assessment of energy conversion in PS I", PAM Application Notes, Jan. 1, 2008 (Jan. 1, 2008) , Retrieved from the Internet: URL:https://www.walz.com/files/downloads/pan/PAN07002.pdf.

Popova Antoaneta V et al: "Differential temperature effects on dissipation of excess light energy and energy partitioning in lut2 mutant of Arabidopsis thaliana under photoinhibitory conditions",Photosynthesis Research, Springer Netherlands, Dordrecht, NL,vol. 139, No. 1,May 3, 2018 (May 3, 2018) ,pp. 367-385.

EP 21891992.6, Supplemental European Search Report dated Oct. 2, 2024, 12 pages—English.

* cited by examiner (a)             (b)

30a  30b (a)  (b)

Phase difference 90°
Duty ratio 5:5

(a)

Phase difference 90°
Duty ratio 8:2

(b)

Y(ND)/V(O2) plot

Data of Y(ND)-V(O2)

K free

Mo free

Zn free (upper leaf)

B free (1 week)

DIAGNOSIS DEVICE FOR ENVIRONMENTAL STRESS IN PLANTS AND ENVIRONMENTAL STRESS DIAGNOSIS METHOD

CROSS REFERENCE TO RELATED APPLICATIONS

This application relates to and claims priority from PCT/JP2021/041742 filed Nov. 12, 2021 the entire contents of which are incorporated herein by reference. which in turn claims the priority to Japanese Patent Application No. 2020-189009 filed on Nov. 12, 2020, which is incorporated herein by reference.

TECHNICAL FIELD

The present invention relates to an improved technology for a device that measures photosynthetic activity, in particular, a device (an environmental stress diagnosis device) that identifies and diagnoses an environmental stress state of plants by measuring the photosynthetic activity.

BACKGROUND OF THE INVENTION

Chlorophyll fluorescence measurement has conventionally been utilized as means for learning the photosynthetic activity of plants. This chlorophyll fluorescence measurement is a technology for mainly detecting the activity of photosystem II which is an initial stage of photosynthesis. In chlorophyll fluorescence measurement, how many electrons are produced from water molecules in a photochemical reaction can be quantitatively identified by monitoring slight light energy (chlorophyll fluorescence) emitted from chlorophyll.

Plants are subject to various types of environmental stress on a daily basis. This environmental stress inhibits photosynthesis of plants, and surplus light energy is accompanied by production of reactive oxygen species (ROS), which may damage the growth of plants.

Specifically, accumulation of ROS in plant cells causes generation of activated nitrogen, lipid peroxide, and activated carbonyl, which resultantly might lead even to damage of cellular functions or withering. For example, cucumber which is a model plant of cucurbitaceous crops and is known as a cold-sensitive crop is subject to growth disorders due to ROS under cold stress. This results in a large cost for temperature management particularly in greenhouse cultivation in winter.

In other words, an ability to find production of ROS in plants and eventually environmental stress in plants in an early stage enables appropriate temperature management in the example of greenhouse cultivation of cucumber. Further, early finding of environmental stress can also contribute to selection of stress tolerant varieties or the like in addition to the cost reduction effect in growing plants and growth evaluation of plants. Besides, early finding of environmental stress may allow finding of a mineral nutrient deficiency in plants in an early stage. From such perspectives, research related to early diagnosis of environmental stress in plants has been worked on recently.

Patent Literature 1, for example, discloses a technology related to a plant health diagnosis device that diagnoses health condition of plants by calculating, on a time-dependent changing curve of chlorophyll fluorescence intensity, a smallest local minimum point s (defined as S) appearing after a local maximum point p at which the chlorophyll fluorescence intensity is maximized and a local maximum point m (defined as M) appearing first after the local minimum point s and comparing the values of S and M.

CITATION LIST

Patent Literature

Patent Literature 1: Japanese Patent No. 5881082

SUMMARY OF THE INVENTION

Technical Problem

Patent Literature 1 enables early finding of the health condition of plants by performing an analysis under predetermined conditions utilizing the chlorophyll fluorescence measurement. However, the chlorophyll fluorescence measurement is a technology for mainly detecting the activity of the photosystem II which is the initial stage of photosynthesis as described above. In other words, only with the chlorophyll fluorescence measurement, it cannot be learned how electrons resulting from a photochemical reaction are used in the downstream of electron transfer (photosystem I).

That is, only with the chlorophyll fluorescence measurement, even a state in which electrons have passed to oxygen and produced reactive oxygen species (ROS) in the photosystem I might be detected as an effective activity of the photosystem II, which leaves room for further improvement for performing an accurate environmental stress diagnosis.

The present invention was made in view of the problems in the conventional technology, and an object thereof is to achieve a diagnosis device for environmental stress in plants that can diagnose an environmental stress state of plants more accurately, earlier, and non-destructively than in conventional measurement, and can also be used outdoors, and an environmental stress diagnosis method.

Solution to Problem

In order to solve the problems, an environmental stress diagnosis device according to the present invention comprises:

a measurement light source that radiates a measurement light to a plant sample; an induction light source that radiates a photosynthesis inducing light to the plant sample; a sealed chamber that stores the plant sample and allows entry of the measurement light and the photosynthesis inducing light; a transmitted light detector that detects the measurement light transmitted through the plant sample as a transmitted light; and a control unit that receives the transmitted light detected by the transmitted light detector as a measurement signal, the environmental stress diagnosis device diagnosing an environmental stress state of the plant sample, in which the measurement light source outputs two types of a first measurement light and a second measurement light having different wavelengths, the induction light source outputs two types of a first photosynthesis inducing light and a second photosynthesis inducing light having different wavelengths, the control unit has an analysis circuit that analyzes a detection result acquired by the transmitted light detector, and a control circuit that controls the measurement light source and the induction light source to correspond to the plant sample, the control circuit adjusts and controls the first measurement light and the second measurement light to have different output amplitudes, and controls the measurement light source such that the first measurement light and the second measurement light become opposite-phase rectangular waves, the control circuit controls the measurement light source to output the first measurement light and the second measurement light in synchronization to form the first measurement light and the second measurement light into a quasi-single composite rectangular wave measurement light of 5 kHz to 30 kHz including a DC component, the transmitted light detector detects the composite rectangular wave measurement light transmitted through the plant sample as a composite rectangular wave transmitted light, the analysis circuit calculates a light absorption difference between the first measurement light and the second measurement light transmitted through the plant sample utilizing the composite rectangular wave transmitted light, and calculates Y(ND) which is a state in which P700 in photosystem I has been oxidized in photosynthesis as a ROS marker which is a reactive oxygen species suppression index for a plant utilizing the light absorption difference, and the analysis circuit diagnoses the environmental stress state of the plant sample utilizing the ROS marker.

In addition, the environmental stress diagnosis device according to the present invention is further equipped with a communication unit for network connection, in which the environmental stress diagnosis device is network-connected to a communication terminal via the communication unit, the communication terminal is utilized for operating the environmental stress diagnosis device, and displays the ROS marker as a measurement result and an environmental stress diagnosis result, and the communication terminal is network-connected to a data server in which environmental stress diagnosis data is accumulated, and compares the environmental stress diagnosis data and the ROS marker to diagnose the environmental stress state of the plant sample.

In addition, in the environmental stress diagnosis device according to the present invention, the control circuit synchronizes the first measurement light and the second measurement light that are output from the measurement light source by PWM control, the control circuit compares falling timings of rectangular waves in the first measurement light and the second measurement light with a reference signal waveform as a command frequency, and in a case in which the falling timings in the first measurement light and the second measurement light lose synchronization due to output from the measurement light source, the control circuit adjusts the falling timings in a unit of 0.25 μs to maintain synchronization.

In addition, in the environmental stress diagnosis device according to the present invention, the induction light source performs stationary radiation with the first photosynthesis inducing light as continuous radiation, performs pulse radiation with the first photosynthesis inducing light as higher power radiation than the stationary radiation without providing a pausing period after the stationary radiation, thereafter provides a pausing period, performs stationary radiation with the second photosynthesis inducing light, and performs pulse radiation with the second photosynthesis inducing light without providing a pausing period after the stationary radiation, and a radiation time of the pulse radiation is 1 ms to 300 ms.

In addition, in the environmental stress diagnosis device according to the present invention, the sealed chamber is equipped with an oxygen concentration detector that measures an oxygen production rate of the plant sample inside the sealed chamber, and the analysis circuit diagnoses the environmental stress state of the plant sample utilizing a correlation between the ROS marker and the oxygen production rate (a photosynthesis rate).

In addition, in the environmental stress diagnosis device according to the present invention, the sealed chamber is equipped with all or any of a temperature sensor, a humidity sensor, and an atmospheric pressure sensor as an environment sensor, and the analysis circuit performs correction processing on the oxygen production rate detected by the oxygen concentration detector based on a detection result acquired by the environment sensor.

In addition, in the environmental stress diagnosis device according to the present invention, the oxygen concentration detector is a galvanic cell type oxygen concentration detector.

In addition, in the environmental stress diagnosis device according to the present invention, the sealed chamber is equipped with an exhaled air introduction port for externally introducing exhaled air and an air output port for replacing air inside the sealed chamber.

In addition, the environmental stress diagnosis device according to the present invention is further equipped with a fluorescence detector that detects chlorophyll fluorescence from the plant sample, in which the analysis circuit calculates, from a chlorophyll fluorescence detection result (when in a saturated CO2 state) acquired by the fluorescence detector, Y(II) as a photosynthesis rate, Y(NPQ) as light energy that cannot be utilized for photosynthesis, Y(NO) as fundamental heat dissipation performance in photosystem II, and 1-pL as a plastoquinone reduction rate, the analysis circuit utilizes the light absorption difference to calculate Y(I) which is a ground state of P700 and Y(NA) which is a state in which P700 is absorbing light energy, and the analysis circuit utilizes all or any of the Y(II), Y(NPQ), Y(NO), 1-pL, Y(I), Y(NA), and Y(ND) which is the ROS marker to diagnose a mineral nutrient deficiency in the plant sample.

In addition, in the environmental stress diagnosis device according to the present invention, the analysis circuit creates a sample diagnosis graph in which an elapse of time is expressed circularly and values acquired by dividing Y(I), Y(ND), and Y(NA) by Y(II) are plotted, and the analysis circuit compares a basic diagnosis graph showing a plant in which mineral nutrients are controlled and the sample diagnosis graph to diagnose deficiency of all or any of N, P, K, S, Mg, Ca, B, Zn, Mo, Cu, Fe, and Mn which are essential nutrients in the plant sample.

In addition, in the environmental stress diagnosis device according to the present invention, the sealed chamber is equipped with a temperature adjustment unit for controlling a temperature of the plant sample positioned inside the sealed chamber.

Then, an environmental stress diagnosis method for a plant according to the present invention comprises the steps of:

storing a plant sample in a sealed chamber, and by a control circuit, adjusting a first measurement light and a second measurement light that are output from a measurement light source and adjusting a first photosynthesis inducing light and a second photosynthesis inducing light that are output from an induction light source;

controlling the measurement light source by the control circuit such that the second measurement light has higher power than the first measurement light and the first measurement light and the second measurement light become opposite-phase rectangular waves, controlling the measurement light source by the control circuit such that the first measurement light and the second measurement light are output in synchronization to form the first measurement light and the second measurement light into a quasi-single composite rectangular wave measurement light of 5 kHz to 30 kHz including a DC component, and radiating the composite rectangular wave measurement light together with the first photosynthesis inducing light and the second photosynthesis inducing light to the plant sample;

detecting, by a transmitted light detector, the composite rectangular wave measurement light transmitted through the plant sample as a composite rectangular wave transmitted light having a single frequency;

calculating, by an analysis circuit, a light absorption difference between the first measurement light and the second measurement light transmitted through the plant sample by utilizing the composite rectangular wave transmitted light, and calculating, by the analysis circuit, Y(ND) which is a state in which P700 in photosystem I has been oxidized in photosynthesis as a ROS marker which is a reactive oxygen species suppression index for a plant by utilizing the light absorption difference; and diagnosing an environmental stress state of the plant sample by utilizing the ROS marker.

Advantageous Effects of Invention

According to the present invention, the control circuit controls the measurement light source such that the second measurement light has slightly higher power than the first measurement light and the first measurement light and the second measurement light become opposite-phase rectangular waves. Further, the control circuit controls the measurement light source such that the first measurement light and the second measurement light are output in synchronization to form the first measurement light and the second measurement light into a quasi-single composite rectangular wave measurement light of 5 kHz to 30 kHz including a DC component. Then, the ROS marker is calculated by utilizing the composite rectangular wave transmitted light transmitted through the plant sample, and an environmental stress diagnosis utilizing the acquired ROS marker is performed. Thus, an environmental stress diagnosis device that can diagnose an environmental stress state of plants more accurately and earlier than in conventional chlorophyll fluorescence measurement can be provided.

As a result, the ROS marker measured (and calculated) by the environmental stress diagnosis device according to the present invention (or the correlation between the ROS marker and the oxygen production rate or the like) can be utilized as a selection marker for cold stress tolerant varieties, for example. Further, the ROS marker (or the correlation between the ROS marker and the oxygen production rate, and in addition, chlorophyll fluorescence parameters) can also be utilized for diagnosing a mineral nutrient deficiency in plants (diagnosing mineral nutrient stress).

DESCRIPTION OF EMBODIMENTS

Hereinafter, an environmental stress diagnosis device of the present invention is described with reference to the drawings, but is not limited to the following examples without departing from the purpose of the present invention.

Figure 1:
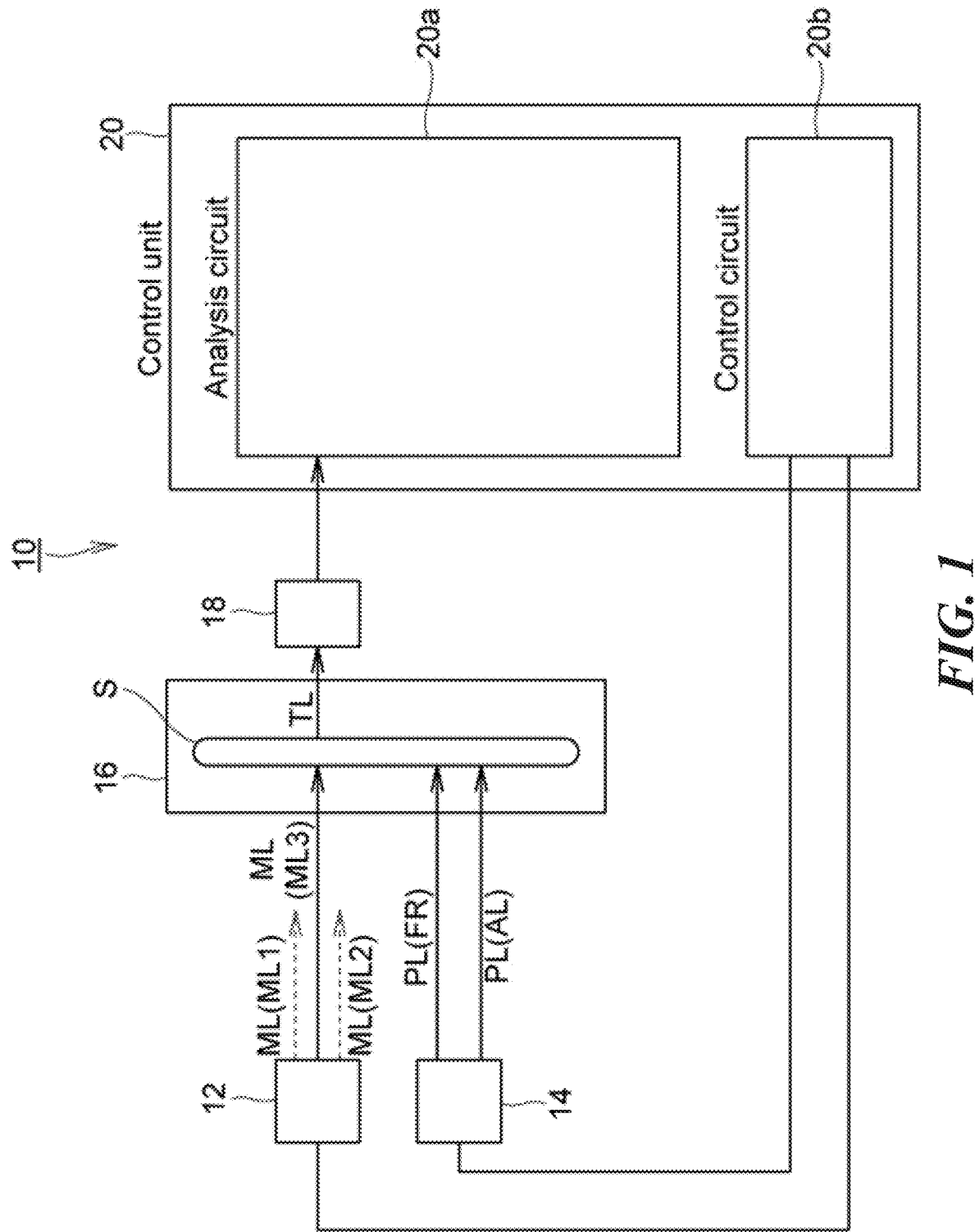
FIG. 1 shows a schematic configuration diagram of an environmental stress diagnosis device according to an embodiment of the present invention.

FIG. 1 shows a schematic configuration diagram of an environmental stress diagnosis device according to an embodiment of the present invention. An environmental stress diagnosis device 10 according to the present embodiment is mainly intended to be used outdoors. That is, the environmental stress diagnosis device 10 is a portable device that can be brought to a field environment, and is brought to a site to directly gauge plants (living leaves) and perform an environmental stress diagnosis. The environmental stress diagnosis device 10 according to the present embodiment can be driven with a power battery of 5 V to 20 V (a power battery of 12 V, for example).

Figure 2:
FIG. 2 shows schematic image views of the environmental stress diagnosis device according to the embodiment of the present invention.
Figure 2:
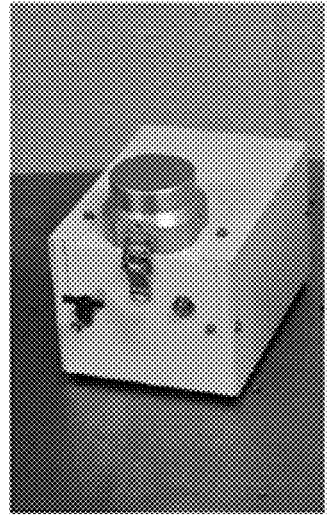

In the present embodiment, an operation display unit can be provided on a portion of a housing in the environmental stress diagnosis device 10, for example, to operate the device and display diagnosis results by the operation display unit (see FIG. 2(a)).

In addition, the environmental stress diagnosis device 10 may not be equipped with the operation display unit (see FIG. 2(b)), and operation of the device and display of diagnosis results may be performed by a communication terminal (portable terminal) such as a smartphone or a tablet. In this case, communication between the communication terminal and the environmental stress diagnosis device 10 can be performed through wireless communication (in this case, the environmental stress diagnosis device is equipped with a communication unit).

Although electric components such as a battery and the like are actually required because the environmental stress diagnosis device 10 according to the present embodiment is a portable device, illustration of components and the like other than essential components necessary for an environmental stress diagnosis is omitted in FIG. 1.

The environmental stress diagnosis device 10 shown in FIG. 1 is configured to include a measurement light source 12 that radiates a measurement light ML to a plant sample S, an induction light source 14 that radiates a photosynthesis inducing light PL to the plant sample S, a sealed chamber 16 that stores the plant sample S and allows entry of the measurement light ML and the photosynthesis inducing light PL, a light detector 18 that detects the measurement light ML transmitted through the plant sample S as a measurement signal (an electric signal), and a control unit 20 that receives the transmitted light detected by the light detector 18 as a measurement signal (an electric signal).

The environmental stress diagnosis device 10 according to the present embodiment performs characteristic measurement light radiation on the plant sample S (a living leaf of a plant) stored in the sealed chamber 16, thereby measuring a ROS marker as a reactive oxygen species suppression index.

The measurement light source 12 outputs two types of a first measurement light ML1 and a second measurement light ML2 having different wavelengths. In the present embodiment, characteristic measurement light radiation and dual-wavelength light absorption difference measurement are performed by utilizing the first measurement light ML1 and the second measurement light ML2. Specifically, the first measurement light ML1 and the second measurement light ML2 are radiated to the plant sample S as a single composite measurement light ML3 (called a composite rectangular wave measurement light, details of which is described later) as shown in FIG. 1.

The measurement light source 12 is configured to include two types of LEDs, for example. In the present embodiment, the first measurement light ML1 has a wavelength of 810 nm or 830 nm, and the second measurement light ML2 has a wavelength of 880 nm or 910 nm. Note that the wavelengths of the first measurement light ML1 and the second measurement light ML2 can be changed as appropriate depending on the type of the plant sample S or measurement.

Here, in the dual-wavelength light absorption difference measurement in the present embodiment, a dual-wavelength light absorption difference waveform can be acquired by subtracting waveform data of a transmitted light TL acquired when the first measurement light ML1 is transmitted through the plant sample S from waveform data of the transmitted light TL acquired when the second measurement light ML2 is transmitted through the plant sample S.

That is, although details is described later, three states of P700(Y(ND)) in a ground state, P700(Y(NA)) in an excited state, and P700+(Y(ND)) in an oxidized state are present in P700 which is a measurement target. Thus, in order to estimate the amount of Y(ND), a wavelength region that changes largely depending on Y(ND) is selected as the first measurement light ML1, and a wavelength region that is common to the three states and does not depend largely on Y(ND) is selected as the second measurement light ML2, thereby acquiring a difference between the first measurement light ML1 and the second measurement light ML2.

Then, in the present embodiment, the dual-wavelength light absorption difference waveform can be acquired by utilizing the single measurement light ML3 in which ML1 and ML2 are synthesized. In the present embodiment, the ROS marker and the like can be calculated by utilizing this light absorption difference waveform.

In addition, when the plant sample S is brought into a photosynthetically active state, various parameters such as the ROS marker change with time. At this time, a background of the plant sample S also changes with time in measurement of light absorption (detection of light transmitted through the plant sample S).

Hence, in the present embodiment, the background in measurement can also be corrected by performing the dual-wavelength light absorption difference measurement. That is, the dual-wavelength absorption difference measurement in the present embodiment cancels the time-dependent change of the background and thus can achieve accurate measurement.

A wavelength of 880 nm or 910 nm at which changes through absorption are small and which is close to the wavelength (810 nm or 830 nm) of the first measurement light ML1 is adopted for the second measurement light ML2 in the present embodiment.

The induction light source 14 radiates two types of a first photosynthesis inducing light FR and a second photosynthesis inducing light AL having different wavelengths to the plant sample S. The induction light source 14 is configured to include two types of LEDs, for example. In the present embodiment, the first photosynthesis inducing light FR has a wavelength of 740 nm, and the second photosynthesis inducing light AL has a wavelength of 640 nm. Note that the wavelengths of the first photosynthesis inducing light FR and the second photosynthesis inducing light AL can be changed as appropriate depending on the type of the plant sample S or measurement. For example, the wavelength of the second photosynthesis inducing light AL can also be changed as appropriate in a range from 400 nm to less than 700 nm.

In the present embodiment, a filter can also be provided between the LED for outputting the first photosynthesis inducing light FR and the sealed chamber 16. By providing the filter, interference between the measurement light ML and the first photosynthesis inducing light FR can be suppressed. Further, in the present embodiment, an optical filter that interrupts the first photosynthesis inducing light FR and AL can also be provided between the sealed chamber 16 and the light detector 18 (in front of the light detector 18).

The first photosynthesis inducing light FR and the second photosynthesis inducing light AL are radiated to the plant sample S by combining a continuous radiation (called stationary radiation) and a pulsed radiation (called pulse radiation; SP in FIG. 3) which is higher power radiation than the stationary radiation as shown in FIG. 3.

Specifically, the induction light source 14 stationarily radiates the first photosynthesis inducing light FR as the continuous radiation, performs the pulse radiation as higher power radiation than the stationary radiation without providing a pausing period after the stationary radiation, thereafter provides a pausing period and stationarily radiates the second photosynthesis inducing light AL, and performs the pulse radiation without providing a pausing period after the stationary radiation.

Figure 3:
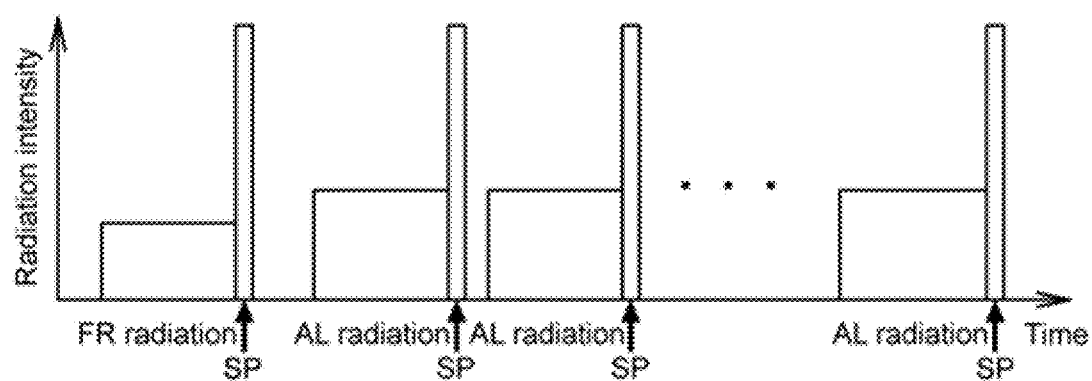
FIG. 3 shows a schematic operation explanatory diagram of an induction light source according to the embodiment of the present invention.

Thereafter, the induction light source 14 radiates only the second photosynthesis inducing light AL to the plant sample S as in FIG. 3. Note that radiation of the first photosynthesis inducing light FR can also be performed at the end of inducing light radiation, for example. In addition, the stationary radiation in the present embodiment is performed for approximately 5 seconds to 60 seconds both for the first photosynthesis inducing light FR and the second photosynthesis inducing light AL. Note that the time for this stationary radiation may be 60 seconds or more depending on the type of the plant sample S to be measured.

In addition, in the present embodiment, radiation (stationary radiation and pulse radiation) of the first photosynthesis inducing light FR may be performed twice or more. By performing radiation of the first photosynthesis inducing light FR twice or more, an idling state of the plant sample S, which is described later, can be acquired more stably.

The amount of light (photon flux density) of the first photosynthesis inducing light FR in the stationary radiation in the present embodiment is approximately 30 $\mu molm^{-2}s^{-1}$ to 70 $\mu molm^{-2}s^{-1}$. In addition, the amount of light (photon flux density) of the second photosynthesis inducing light AL in the stationary radiation is approximately 100 $\mu molm^{-2}s^{-1}$ to 2000 $\mu molm^{-2}s^{-1}$.

Figure 4:
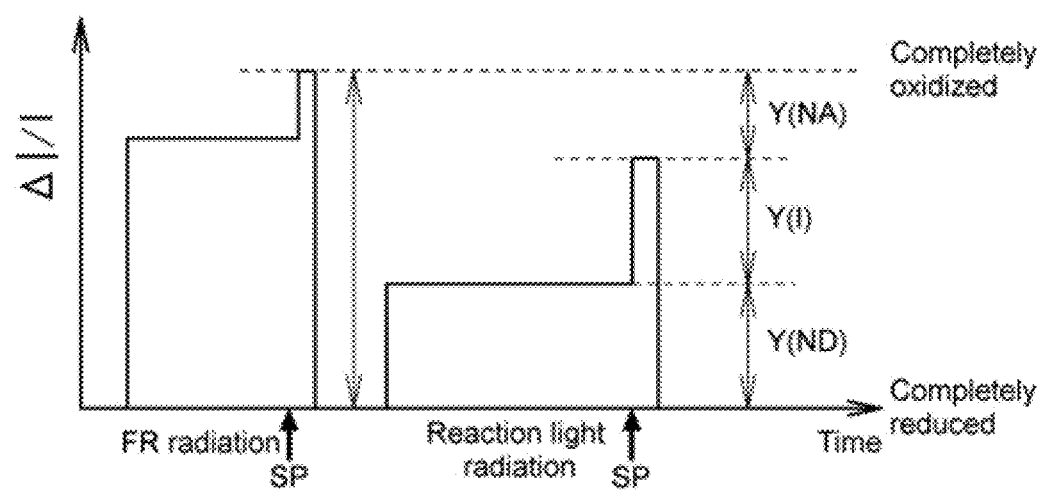
FIG. 4 shows a schematic image diagram of P700 absorption change obtained by radiation of photosynthesis inducing lights in the present embodiment.

FIG. 4 shows a schematic image diagram of P700 light absorption change acquired by radiation of the photosynthesis inducing light in the present embodiment. As shown in FIG. 4, the stationary radiation of the first photosynthesis inducing light FR is performed for bringing the photosystem I in the plant sample S into a stationary operation state (idling state) (to trigger a photosynthesis cycle of the photosystem I in the plant sample S because the inside of the sealed chamber 16 is dark). Moreover, the pulse radiation of the first photosynthesis inducing light FR is performed for identifying the total amount of P700 in the photosystem I (the total amount of Y(I), Y(NA), and Y(ND) indicating the respective states in P700, which is described later).

In the present embodiment, the pulse radiation of the first photosynthesis inducing light FR (740 nm) to the plant sample S enables only the photosystem I to be driven without driving the photosystem II (or the photosystem I can be driven faster than driving of the photosystem II).

Specifically, the photosystem I in the plant sample S is brought into the stationary operation state by the stationary radiation of FR. The pulse radiation of FR at this time brings P700 into a completely oxidized state. That is, P700 is brought into the completely oxidized state before the photosynthesis cycle in the photosystem I operates, and the total amount of P700 in the photosystem I can be identified by gauging this state.

In addition, if the first photosynthesis inducing light FR has a wavelength of 700 nm or greater, only the photosystem I can be driven. In this manner, in the present embodiment, the total amount of P700 can be appropriately identified by driving only the photosystem I by the pulse radiation of FR.

The stationary radiation of the second photosynthesis inducing light AL is performed for bringing the photosynthesis cycle (the photosynthesis cycle that operates both the photosystem II and the photosystem I) in the plant sample S into the idling state and identifying Y(ND) which is a state in which P700 has been oxidized. That is, the second photosynthesis inducing light AL plays a role of quasi-solar light radiation.

Then, the pulse radiation of the second photosynthesis inducing light AL is performed for identifying P700(Y(I)) that is reduced and in the ground state. In addition, calculation of a difference between the total amount of P700 acquired by the pulse radiation of FR and Y(I)+Y(ND) that can be identified by the radiation of AL enables P700*(Y(NA)) which is a state absorbing light energy to be identified.

A radiation time of the pulse radiation SP is preferably 1 ms to 300 ms, more preferably is 50 ms to 250 ms, and still more preferably 200 ms. In addition, the amount of light (photon flux density) of the pulse radiation of AL in the present embodiment is approximately 5000 $\mu molm^{-2}s^{-1}$ to 15000 $\mu molm^{-2}s^{-1}$. The environmental stress diagnosis device 10 according to the present embodiment can accurately measure the oxidized state (the ROS marker) of P700 in the photosystem I by this characteristic inducing light radiation technology.

The sealed chamber 16 stores the plant sample S as a measurement target. In the present embodiment, a living leaf cut into approximately 8 to 16 mm squares can be utilized as the plant sample S (the plant sample S is measured non-destructively). Although illustration is omitted in FIG. 1, the sealed chamber 16 is equipped with a light guide window at a position where the measurement light ML (ML3) from the measurement light source 12 and the photosynthesis inducing light PL (FR, AL) from the induction light source 14 can enter the sealed chamber 16.

In addition, in the present embodiment, a light guide can also be provided between both the measurement light source 12 and the induction light source 14 and the sealed chamber 16. By providing the light guide, the measurement light ML and the photosynthesis inducing light AL are radiated along the same optical path, and uniform radiation to the measurement sample S (a surface of S) can be achieved.

Similarly, a light guide can also be provided between the sealed chamber 16 and the light detector 18, for example. By providing the light guide at this position, the transmitted light TL can be detected efficiently. Specifically, by providing the light guide, the transmitted light detector 18 can detect the transmitted light TL 20% to 30% more than in the conventional measurement.

The volume of the sealed chamber 16 in the present embodiment is preferably approximately 2 ml to 20 ml, more preferably 5 ml to 10 ml, and particularly preferably 8 ml. When the sealed chamber 16 has such a volume, measurement can be performed without exhausting $CO_2$ for approximately about 20 minutes to 30 minutes from a saturated $CO_2$ state. The saturated $CO_2$ state herein means a state in which the carbon dioxide concentration has reached approximately 1% to 4%. The present embodiment performs measurement with the carbon dioxide concentration inside the sealed chamber 16 set at approximately 1% to 4%. In addition, the sealed chamber 16 according to the present embodiment has a columnar shape, but may have another shape such as a quadrangular prism shape or a hemispherical shape, for example.

Figure 5:
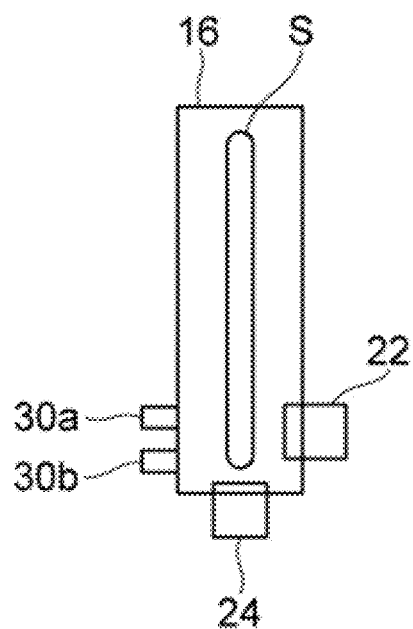
FIG. 5 shows a schematic explanatory diagram of an exhaled air introduction port and an air output port according to the embodiment of the present invention.
Figure 6:
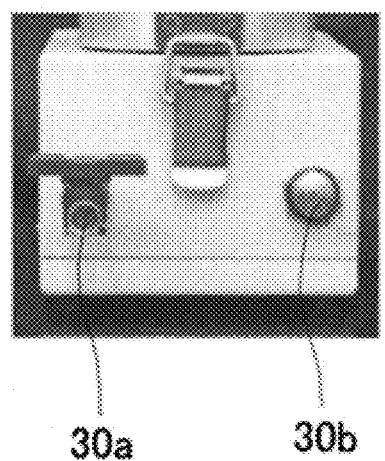
FIG. 6 shows schematic image views of the exhaled air introduction port and the air output port according to the embodiment of the present invention.
Figure 6:
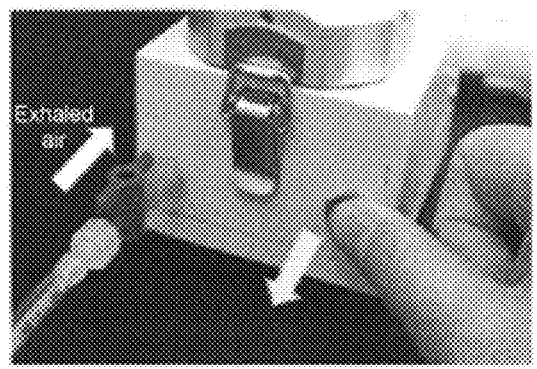

Further, in the present embodiment, the sealed chamber 16 can also be equipped with an exhaled air introduction port 30a for introducing human exhaled air (beath) (or for connection to the sealed chamber 16 from the outside of the device) as shown in FIG. 5 and FIG. 6(a), for example.

The sealed chamber 16 can easily create the saturated $CO_2$ state inside the sealed chamber 16 when human exhaled air is introduced through this exhaled air introduction port 30a (FIG. 6(b)). By creating this saturated $CO_2$ state, the maximum photosynthetic ability can be gauged upon measurement (particularly upon outdoor measurement). That is, the maximum photosynthetic performance can be evaluated in the present embodiment, thus enabling highly accurate measurement (measurement of the ROS marker and oxygen concentration measurement, which is described later) which does not depend on the state of pores, offers high reproducibility, and facilitates comparative evaluation to be performed.

In addition, in the present embodiment, by putting a sodium bicarbonate solution, for example, into the sealed chamber 16, carbon dioxide can be produced in the sealed chamber 16. For example, in the present embodiment, the oxygen concentration measurement can also be performed by impregnating a cloth or felt with the sodium bicarbonate solution and putting the cloth or felt into the sealed chamber 16.

On the other hand, when the exhaled air introduction port 30a is closed without letting in exhaled air, the sealed chamber 16 can be maintained in a sealed state, so that a low $CO_2$ state can be created resultantly, and a minimum photosynthetic ability can also be gauged.

Additionally, the sealed chamber 16 can also be equipped with an air output port 30b as shown in FIG. 5 and FIG. 6(a). In the present embodiment, by providing this air output port 30b, air in the sealed chamber 16 can easily be replaced even in the state in which the plant sample S is stored in the sealed chamber 16. Positions at which the exhaled air introduction port 30a and the air output port 30b are provided are not particularly limited.

The transmitted light detector 18 detects the composite rectangular wave measurement light ML3 (ML1 and ML2) transmitted through the plant sample S as the composite rectangular wave transmitted light TL. A PIN photodiode, for example, can be utilized as the transmitted light detector 18 according to the present embodiment.

The control unit 20 has an analysis circuit 20a that analyzes a detection result acquired by the transmitted light detector 18, and a control circuit 20b that controls the measurement light source 12 and the induction light source 14 in correspondence to the plant sample S. A microprocessor or FPGA, for example, can be utilized for the analysis circuit 20a and the control circuit 20b. The analysis circuit 20a performs a data analysis and an environmental stress diagnosis for plants which are characteristic in the present embodiment.

Next, a flow of measurement of the plant sample S (and an environmental stress diagnosis) performed by the environmental stress diagnosis device 10 according to the present embodiment is described. The first measurement light ML1 and the second measurement light ML2 output from the measurement light source 12 reach the plant sample S positioned inside the sealed chamber 16.

At this time, the first measurement light ML1 and the second measurement light ML2 output from the measurement light source 12 are radiated as a quasi-single measurement light (the composite rectangular wave measurement light ML3) to the plant sample S by characteristic control performed by the control circuit 20b in the present embodiment. In addition, the intensity of the measurement light ML (ML1, ML2) output from the measurement light source 12 is automatically adjusted by the control unit 20 (the control circuit 20b) to have the same signal intensity in conformity with the type of the plant sample S (the measurement light ML is automatically adjusted to enable adequate transmission measurement).

At the start of measurement, measurement in a dark state is performed without radiating the photosynthesis inducing light PL (FR, AL) to the plant sample S. Note that the measurement in the dark state can be omitted in the present embodiment. Thereafter, the first photosynthesis inducing light FR and the second photosynthesis inducing light AL are radiated to the plant sample S together with the composite rectangular wave measurement light ML3 (ML1 and ML2).

When the photosynthesis inducing light PL (FR, AL) is radiated, the plant sample S is brought into a photosynthetically active (photochemical reaction) state. Then, the composite rectangular wave measurement light ML3 radiated to the plant sample S is transmitted through the plant sample S, and the composite rectangular wave transmitted light TL transmitted through the plant sample S is detected by the transmitted light detector 18. The detected composite rectangular wave transmitted light TL is sent to the analysis circuit 20a of the control unit 20 as a measurement signal (an electric signal).

The analysis circuit 20a performs an analysis based on the detection result. The analysis circuit 20a calculates a light absorption difference between the first measurement light ML1 and the second measurement light ML2 transmitted through the plant sample S by utilizing the composite rectangular wave transmitted light TL (the dual-wavelength absorption difference gauging).

Thereafter, the analysis circuit 20a calculates Y(ND) which is the state in which P700 in the photosystem I in photosynthesis has been oxidized as the ROS marker which is the reactive oxygen species suppression index for plants by utilizing this light absorption difference. Then, the analysis circuit 20a performs an environmental stress diagnosis for plants by utilizing the ROS marker. By utilizing this ROS marker, the environmental stress diagnosis can be performed more accurately and earlier than in the conventional measurement.

Modification

Figure 7:
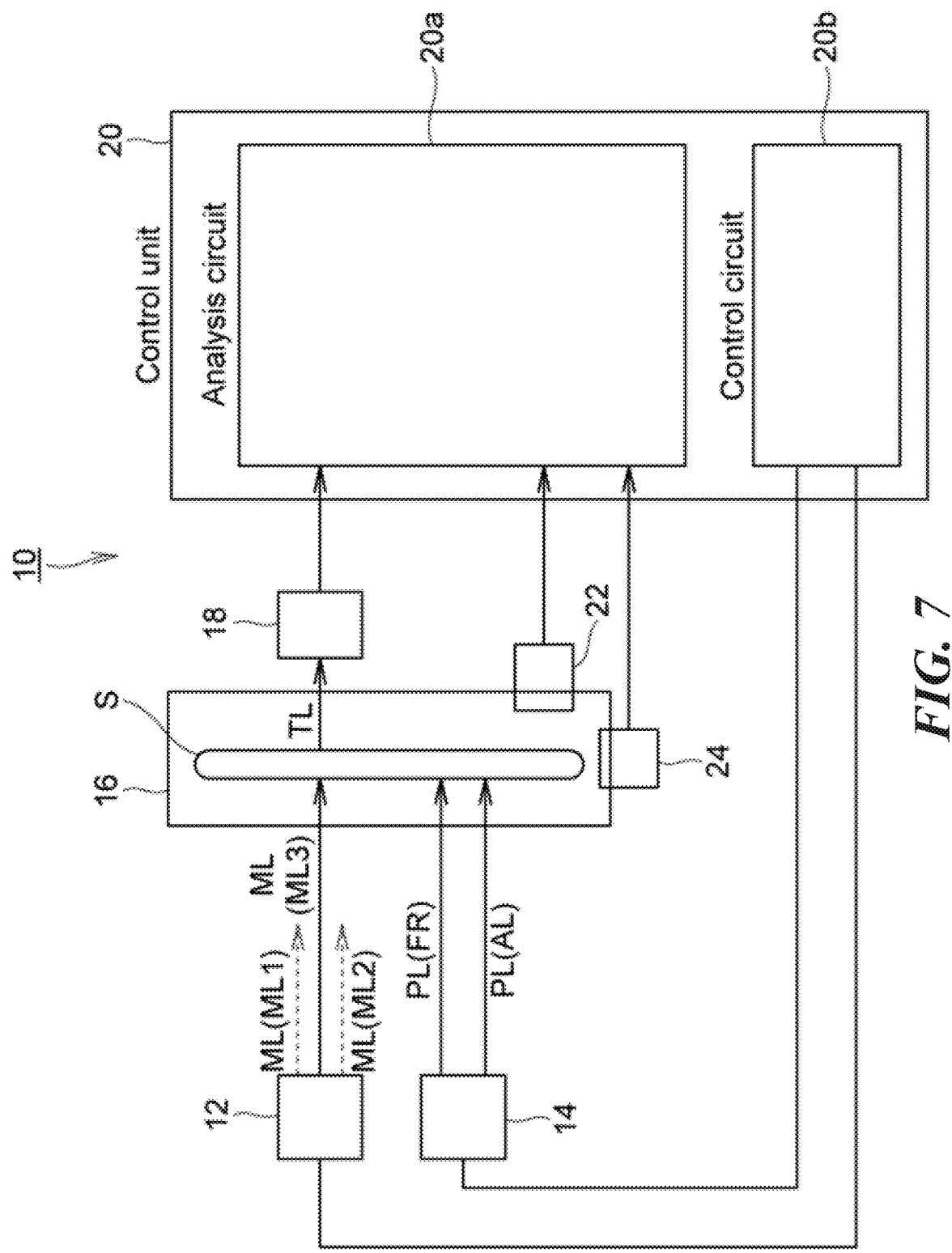
FIG. 7 shows a modification of the environmental stress diagnosis device according to the embodiment of the present invention.

Next, a modification of the environmental stress diagnosis device according to the present embodiment is described. FIG. 7 shows a modification of the environmental stress diagnosis device according to the present embodiment. In FIG. 7, components common to those of the environmental stress diagnosis device 10 shown in FIG. 1 are described with the same reference numerals. As shown in FIG. 7, the sealed chamber 16 of the environmental stress diagnosis device 10 according to the present embodiment is equipped with an oxygen concentration detector 22 that measures an oxygen production rate (also called an oxygen concentration change) of the plant sample S inside the sealed chamber 16, and an environment sensor 24 for identifying an environmental state inside the sealed chamber 16.

The oxygen concentration detector 22 provided in the sealed chamber 16 measures, as the oxygen production rate, the photosynthetic activity of the plant sample S inside the sealed chamber. The oxygen concentration detector 22 is preferably a galvanic cell type oxygen concentration detector, for example.

In the present embodiment, the use of the galvanic cell type (also called an oxygen electrode type) oxygen concentration detector 22 eliminates the need for a power source for driving the oxygen concentration detector 22 in outdoor use, and an effect of improving maintenance properties can be expected.

Further, the galvanic cell type oxygen concentration detector detects oxygen by means of the voltage, and thus has no concentration-dependent detection limit, so that a condition in which the $CO_2$ concentration is higher (approximately 40000 ppm) can be set. If the condition in which the $CO_2$ concentration is high can be set, $CO_2$ can be supplied rapidly into a leaf (the inside of the plant sample S) regardless of an open/close state of pores, which enables rapid stationary-state photosynthetic activity measurement.

In a case of detecting the oxygen concentration through general gas exchange measurement, for example, a constant flow rate of air has to be continuously flowed into the sealed chamber 16. This means that air is always blown onto the plant sample S. That is, plants vulnerable to dryness such as aquatic plants may lose moisture due to continuous air blowing during the gas exchange measurement, and the plant sample S may be damaged.

Note that in the present invention, oxygen measurement is performed even in a state in which no light is radiated. This is to determine a dark respiration rate (oxygen consumption).

In the analysis of the present embodiment, an overall photosynthesis rate (photosynthetic activity performance) acquired by adding an oxygen concentration changing rate (an apparent photosynthesis rate) when the photosynthesis inducing light is radiated and the dark respiration rate.

In addition, when the photosynthetic performance is determined from chlorophyll fluorescence, Y(II) is used, and a value of which is in the saturated $CO_2$ state is used. This is because Y(II) not being in the saturated $CO_2$ state does not correctly express the photosynthetic performance.

In addition, also in a case of converting the photosynthetic performance from the oxygen concentration changing rate (photosynthetic activity performance) into Y(II) for evaluation with a Y(ND)-Y(II) graph and a Y(ND)/Y(II) value, the dark respiration rate is also added to the oxygen concentration changing rate (photosynthetic activity performance). An advantage of converting the oxygen concentration changing rate (photosynthetic performance) into Y(II) lies in that the dimension can be unified with Y(ND).

Y(II) is calculated from an oxygen production rate $V(O_2)$ by the following expression.

$$Y(II) = 4/(\alpha \times PFD) \times \{V'(t) + |V'_o(t)|\}$$
$$= 4/(\alpha \times PFD) \times \{V(O_2)\}$$

α: a constant of 0.42 to 0.48
PFD: the photon flux density: the photosynthesis inducing light AL [μmol/m²/s]
V'(t): the apparent oxygen production rate (the apparent photosynthesis rate)
V'₀(t): the dark respiration rate (a value in a stable state before light radiation: a value acquired by subtracting an oxygen sensor consumption rate)

On the other hand, in the galvanic cell type oxygen concentration detector 22, the inside of the sealed chamber 16 can be maintained in the sealed state and in a highly wet state because a felt impregnated with water can be disposed inside the chamber. Thus, moisture of the plant sample S will not be lost during the oxygen concentration measurement.

The environment sensor 24 is provided for measuring an environmental state (environmental information) inside the sealed chamber 16. All or any of a temperature sensor, a humidity sensor, and an atmospheric pressure sensor, for example, can be utilized as the environment sensor 24. In addition, the environment sensor 24 is not limited to the temperature sensor, the humidity sensor, and the atmospheric pressure sensor, but may be a sensor for measuring another environmental parameter.

As described above, the environmental stress diagnosis device 10 according to the present embodiment is mainly intended to be used outdoors. It is needless to say that in an outdoor field site, respective conditions of temperature, humidity, atmospheric pressure, and the like are different depending on a district in question or environment. The environmental stress diagnosis device 10 in FIG. 7 can perform data correction (correction processing) on the oxygen production rate of the plant sample S inside the sealed chamber 16 by detecting the temperature, humidity, and atmospheric pressure inside the sealed chamber 16 in outdoor use under different environments.

Specifically, data correction on the oxygen production rate of the plant sample S inside the sealed chamber 16 can be performed by utilizing a correction factor $\gamma$ for correcting the oxygen concentration because the oxygen concentration changes due to time-dependent variation of the humidity, temperature, and atmospheric pressure.

$$\gamma = P(t)/P(t0) \times [\{(-4 \times 10^{-7}) \times T^2(t) - (2 \times 10^{-6}) \times T(t)\} \times H(t)+1] \quad \text{[Expression 1]}$$

H(t): a humidity sensor value [%] at a gauging time t
T(t): a temperature sensor value [° C.] at the gauging time t
P(t): an atmospheric pressure sensor value [hPa] at the gauging time t
t0: a time at the time of calibration In the present embodiment, the oxygen concentration $O_2$ can be calculated with the following expression by utilizing this correction factor $\gamma$.

$$O_2[\mu mol\ O_2] = K(t_0) \times Vs(t) \times \gamma(t) \quad \text{[Expression 2]}$$

Vs(t): a voltage signal [V] of the oxygen sensor at the gauging time t
$K(t_0)$: a conversion coefficient between the oxygen concentration and the voltage signal at the time of calibration Further, the oxygen production rate $V(O_2)$ can be calculated with the following expression.

$$V(O_2)[\mu mol\ O_2/m^2 \cdot s] = 10^4/A \times K(t_0) \times d/dt\{Vs(t) \times \gamma(t)\} \quad \text{[Expression 3]}$$

A: leaf area [cm$^2$]

The analysis circuit 20a in FIG. 7 calculates the light absorption difference between the first measurement light ML1 and the second measurement light ML2 transmitted through the plant sample S by utilizing the composite rectangular wave transmitted light TL (the dual-wavelength absorption difference gauging). Thereafter, by utilizing this light absorption difference, the analysis circuit 20a calculates Y(ND) which is the state in which P700 in the photosystem I in photosynthesis has been oxidized as the ROS marker which is the reactive oxygen species suppression index for the plant.

In the present embodiment, radiation intensity of the measurement light is adjusted by constant current control over an LED light source, and a drive current can be changed to be linear.

The present embodiment is characteristic in that a waveform after having been transmitted through the sample and passed through the light sensor becomes a single composite rectangular wave waveform. By setting a sample and making light detection signals of the two measurement lights to have the same value wherever possible, spectroscopic characteristics of the two measurement lights can be made the same.

When a light (the photosynthesis inducing light) is radiated in this state, the light absorption difference between the two measurement lights can be calculated accurately.

Specifically, in the dual-wavelength absorption difference measurement, a sample is set first, and the signal intensities of the dual wavelengths of the measurement lights are made to be equivalent. However, there is actually a noise width, and it is difficult to equalize the signal intensities with a DC signal. In the present embodiment, by forming a single composite rectangular wave waveform, lock-in amplifier processing is performed by signal processing. A signal intensity difference of less than or equal to the noise width is calculated by this lock-in amplifier processing, and the signal difference between the dual-wavelength measurement lights can be made small, so that light absorption when the measurement lights are transmitted through the sample and the optical system as well as spectral sensitivity characteristics of the light sensor can be cancelled.

Note that because the frequency is not locked in the lock-in amplifier processing when there is no unevenness between two signals, unevenness is created to a detectable degree. A difference in the unevenness of approximately about 1 to 2% is recognizable. This difference in the unevenness is usually less than or equal to the noise width, and thus, actual measurement is not affected.

In the present embodiment, each intensity of the dual-wavelength measurement lights is adjusted as described below.

First, the signal intensity of either one of the measurement lights (herein, ML2) is measured through the sample, and a supply current to the ML2 light source (LED) is adjusted to have a desired signal intensity.

Next, the other measurement light (ML1) is radiated, the signal intensity is measured through the sample, and a supply current to the ML1 light source (LED) is adjusted such that the signal intensity difference from ML2 becomes about 1 to 2% of the desired signal intensity by the lock-in amplifier processing.

These adjustments are executed automatically after the sample is disposed, and ML1 and ML2 are both adjusted to have the desired signal intensity and have an intensity difference of 2% or lower.

At this time, the oxygen concentration detector 22 detects the oxygen production rate of the plant sample S inside the sealed chamber 16, and an acquired detection result is sent to the analysis circuit 20a. Similarly, the environment sensor 24 detects environmental information (such as temperature, humidity, and atmospheric pressure) inside the sealed chamber 16, and an acquired detection result is sent to the analysis circuit 20a.

The analysis circuit 20a performs correction processing on the oxygen production rate acquired by the oxygen concentration detector 22 based on the environmental information acquired by the environment sensor 24. This correction processing on the oxygen production rate is particularly effective upon outdoor measurement in which various environmental states are assumed.

Then, the analysis circuit 20a analyzes a correlation between the ROS marker and the oxygen production rate (also called a correlation analysis result or a correlation analysis graph), and performs an environmental stress diagnosis for plants by utilizing the acquired correlation analysis result.

Figure 8:
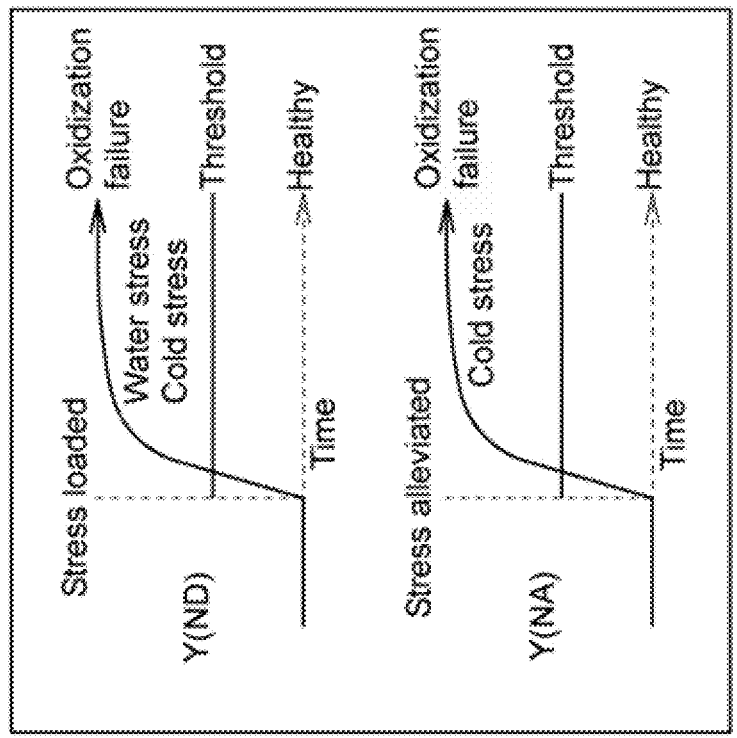
FIG. 8 shows an example of an environmental stress correlation according to the embodiment of the present invention.
Figure 8:
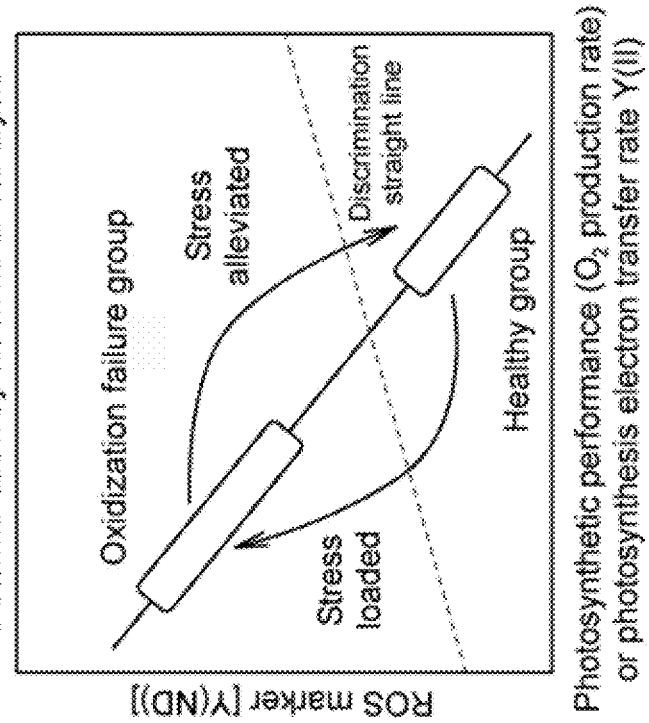

Comparison of this correlation analysis result with environmental stress correlation data (also called an oxidation failure diagnosis manual) stored in advance in the analysis circuit 20a as shown in FIG. 8, for example, enables an accurate and early diagnosis of the environmental stress state of plants (such as whether or not the plants are subject to environmental stress, or the degree of environmental stress).

Figure 9:
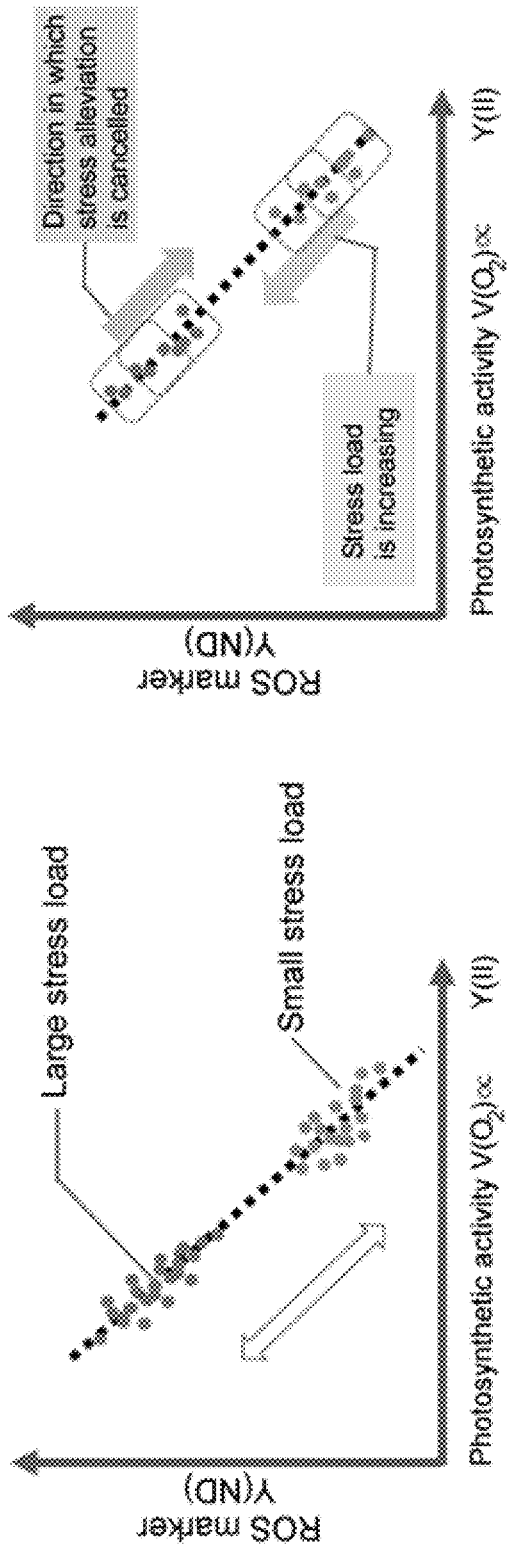
FIG. 9 shows an image diagram of a correlation between a ROS marker and photosynthesis rate acquired by actual measurement in the embodiment of the present invention.

In addition, whether stress loads on plants have been increased or stress loads have been reduced or not can also be diagnosed from the correlation between the ROS marker and the photosynthetic activity (oxygen production rate) V($O_2$) acquired by actual measurement as shown in FIG. 9, for example. Note that Y(II) can also be calculated from the oxygen production rate V($O_2$), and a correlation between the ROS marker and Y(II) as the photosynthesis rate can also be utilized.

Figure 10:
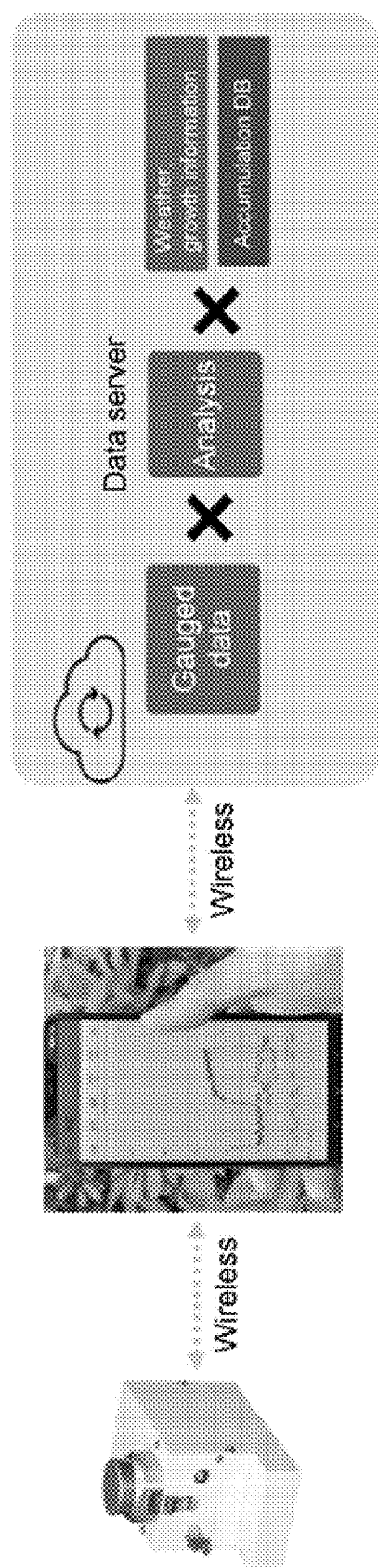
FIG. 10 shows a schematic image diagram of an environmental stress diagnosis utilizing a data server in the present embodiment.

Further, the environmental stress diagnosis device in the present embodiment can diagnose environmental stress in plants by utilizing a data server on a network, for example. FIG. 10 shows a schematic image diagram of an environmental stress diagnosis utilizing a data server.

As shown in FIG. 10, the environmental stress diagnosis device 10 according to the present embodiment can be connected to a communication terminal such as a smartphone or a tablet terminal to the Internet. In this case, the environmental stress diagnosis device 10 is equipped with a communication unit (illustration is omitted) for network connection. The environmental stress diagnosis device 10 is network-connected to the communication terminal via this communication unit (through wireless communication in FIG. 10). Note that the network connection can be performed through wired connection.

As shown in FIG. 10, the environmental stress diagnosis device 10 is operated by utilizing the communication terminal. In addition, the ROS marker as a measurement result, an environmental stress diagnosis result, and the like, for example, are displayed on the communication terminal.

Figure 11:
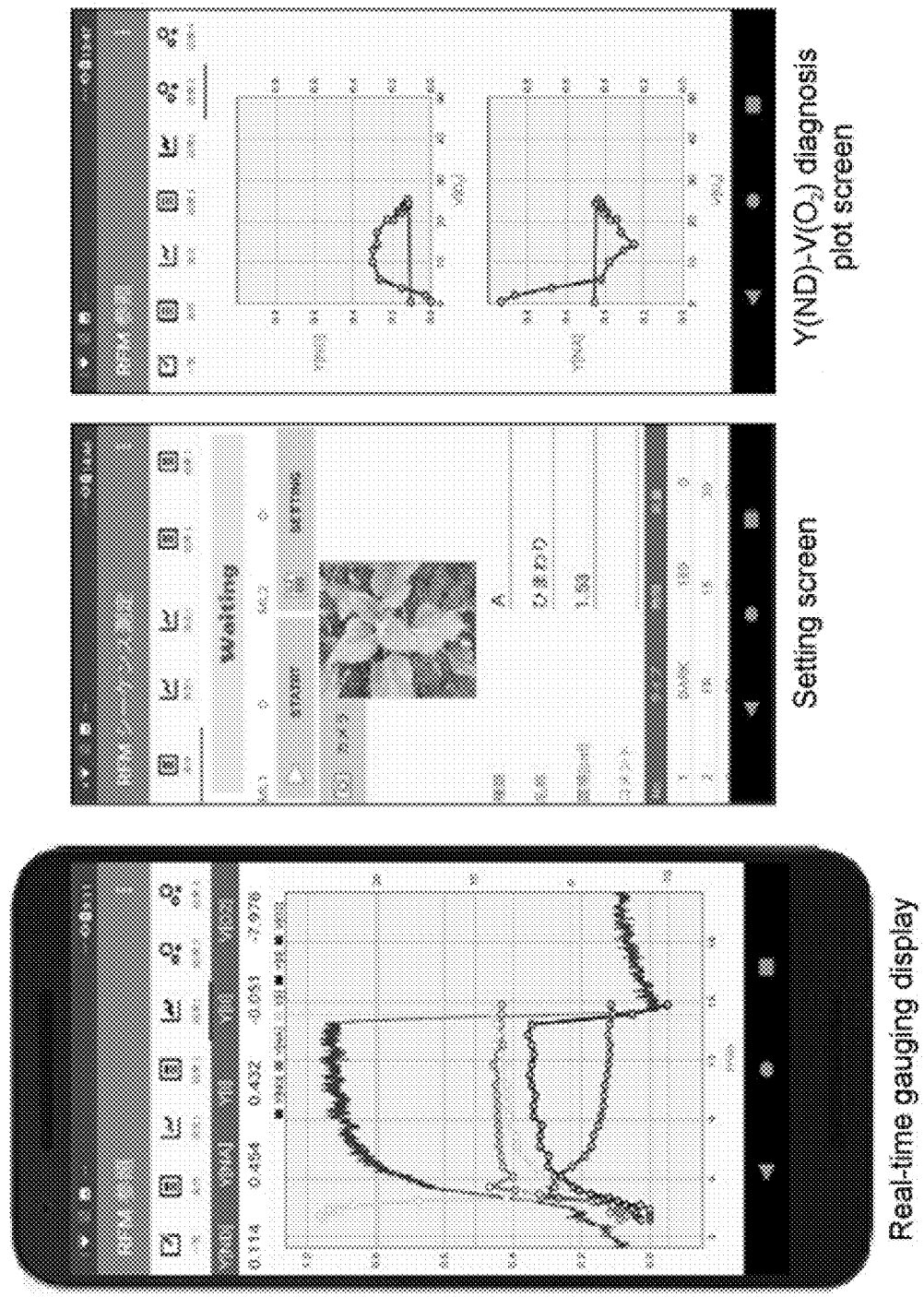
FIG. 11 shows an example of display screens on a portable terminal according to the present embodiment.

As shown in screen images in FIG. 11, for example, a real-time gauging display, a diagnosis plot screen, and the like can also be displayed on the screen of the portable terminal, in addition to a setting screen. Besides, in the present embodiment, the measurement result and the environmental stress diagnosis result may be displayed by utilizing an application, for example.

The communication terminal is network-connected to a data server in which environmental stress diagnosis data and the like are accumulated, for example. Measurement data in the past (such as the ROS marker and other measurement results measured by the device), weather information, other types of growth information, and the like are accumulated in the data server as a database (they are also collectively called environmental stress diagnosis data).

Then, the environmental stress diagnosis device 10 (or the portable terminal) can also compare the environmental stress diagnosis data accumulated in the data server and the measurement results (such as the ROS marker) to diagnose the environmental stress state of the plant sample. Note that classification prediction and an environmental stress diagnosis through machine learning, for example, may be performed.

In this manner, the environmental stress diagnosis device in the present embodiment can diagnose environmental stress in the plant sample accurately and early by utilizing the ROS marker without selecting the location where the plant is measured (even outdoors). The environmental stress diagnosis in the present embodiment is performed generally in the flow as described above.

Regarding Composite Rectangular Wave Measurement Light

Figure 12:
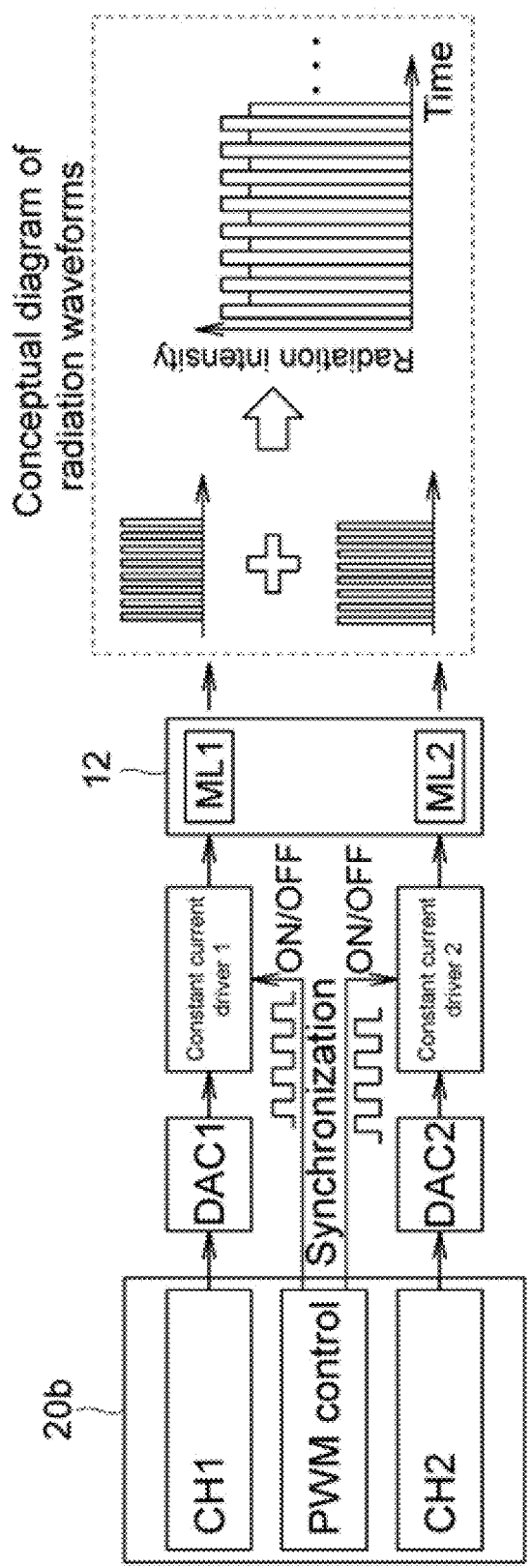
FIG. 12 shows a schematic explanatory diagram of measurement light radiation according to the present embodiment of the present invention.

Next, the composite rectangular wave measurement light is described in detail. In the present embodiment, measurement light radiation utilizing the composite rectangular wave measurement light is performed for measuring the ROS marker accurately. FIG. 12 shows a schematic explanatory diagram of measurement light radiation according to the present embodiment. FIG. 12 is a block diagram showing an operation (control) of the control circuit 20b in FIG. 1 (and FIG. 7).

The control circuit 20b performs constant current control utilizing PWM control (ON/OFF switching control in PWM control) for forming the composite rectangular wave measurement light. As shown in FIG. 12, the control circuit 20b has CH1 for controlling the first measurement light ML1 and CH2 for controlling the second measurement light ML2. CH1 and CH2 output digital signals as control commands.

The digital signals from the control circuit 20b (CH1 and CH2) are converted respectively into predetermined current values (analog signals) in a D/A converter 1 (DAC1) and a D/A converter 2 (DAC2), and the converted analog signals are input to a constant current driver 1 and a constant current driver 2.

At this time, the control circuit 20b outputs PWM signals (on/off signals) for performing PWM control to the constant current driver 1 and the constant current driver 2. These PWM signals make the constant current driver 1 and the constant current driver 2 to operate in accordance with the PWM signals. Specifically, the PWM signals are input in synchronization to the constant current driver 1 and the constant current driver 2 such that ML1 and ML2 become opposite-phase rectangular waves, respectively.

Further, the control circuit 20b according to the present embodiment controls the constant current driver 1 and the constant current driver 2 such that the second measurement light ML2 has higher power than the first measurement light ML1. Note that the control circuit 20b can also control the constant current driver 1 and the constant current driver 2 such that the first measurement light ML1 has higher power than the second measurement light ML2. Based on these PWM signals, the constant current driver 1 makes the measurement light source 12 to output the first measurement light ML1, and the constant current driver 2 makes the measurement light source 12 to output the second measurement light ML2.

The first measurement light ML1 and the second measurement light ML2 from the measurement light source 12 are controlled as opposite-phase rectangular waves, respectively, and thus form a quasi-single rectangular wave (the composite rectangular wave measurement light ML3) including a DC component as shown in FIG. 12. The frequency of the composite rectangular wave measurement light ML3 is preferably 5 kHz to 30 kHz to perform favorable light absorption difference measurement for acquiring the ROS marker, and particularly 8 kHz to 20 kHz is preferred. The frequency of the composite rectangular wave measurement light ML3 in the present embodiment is controlled to be 10 kHz. In addition, the control circuit 20b can adjust and control output amplitudes of the first measurement light ML1 and the second measurement light ML2.

In other words, the control circuit 20b according to the present embodiment controls the measurement light source 12 such that the second measurement light ML2 has higher power than the first measurement light ML1 and the first measurement light ML1 and the second measurement light ML2 become opposite-phase rectangular waves. Further, the control circuit 20b controls the measurement light source 12 to output the first measurement light ML1 and the second measurement light ML2 in synchronization, thereby forming the first measurement light ML1 and the second measurement light ML2 into the quasi-single composite rectangular wave measurement light ML3 of 5 kHz to 30 kHz including a DC component.

The present embodiment can achieve accurate measurement by performing feedback control while performing monitoring with the transmitted light detector 18 such that an output value of the first measurement light ML1 and an output value of the second measurement light ML2 become the same output value, and controlling a detection signal of the second measurement light ML2 (or the first measurement light ML1) transmitted through the plant sample S to fall within 1 to 5% or 1 to 2% of a target set detection value.

The control circuit 20b controls the measurement light source 12 such that the difference between the output values (output amplitudes) of the first measurement light ML1 and the second measurement light ML2 falls within 1% to 5% or 1% to 2% (this numerical value is a numerical value close to an actual noise level). However, when this difference between the output values becomes 0 (the same output value), lock-in amplifier signal processing, which is described later, can no longer be performed. That is, the composite rectangular wave measurement light ML3 including an AC component can no longer be acquired. Thus, the output value of the first measurement light ML1 and the output value of the second measurement light ML2 are controlled to have a slight difference.

Specifically, in a case of assuming that the output value (a current value or a voltage value) of the first measurement light ML1 is 100% in the present embodiment, the output value of the second measurement light ML2 becomes approximately 101% to 105% or approximately 101% to 102%. By adjusting the output values of the first measurement light ML1 and the second measurement light ML2 to fall within this range, accurate measurement can be achieved.

Figure 13:
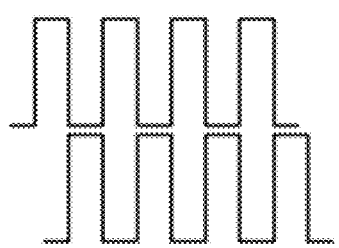
FIG. 13 shows schematic image diagrams of duty ratio in a composite rectangular wave measurement light according to the present embodiment.
Figure 13:
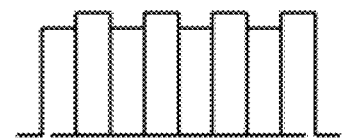
Figure 13:
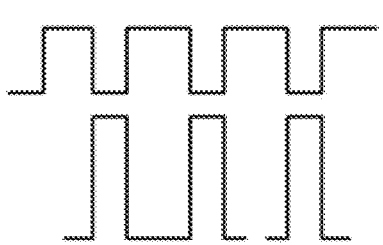
Figure 13:
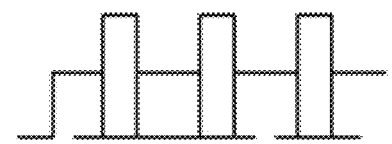

In addition, PMW control (PWM signals) by the control circuit 20b may be set such that the phase difference is 90° and the duty ratio of ML1 and ML2 is 50% each (a duty ratio of 5:5) as shown in FIG. 13(a), for example, or such that the phase difference is 90° and the duty ratio of ML1 and ML2 is 80% and 20% (a duty ratio of 8:2) as in FIG. 13(b). The duty ratio of ML1 and ML2 is not limited to those shown in FIG. 10, and should only be set as appropriate in accordance with measurement. In the present embodiment, the phase difference is 90° and the duty ratio of ML1 and ML2 is 50% each considering easiness of a waveform shaping technology, analytical convenience, and the like.

In addition, regarding an overlapping degree of the two measurement lights, an interval can also be created between overlapping times by setting the duty ratio at 48:48 or 47:47 because the fall times of the two measurement lights can each be adjusted by PWM control.

Figure 14:
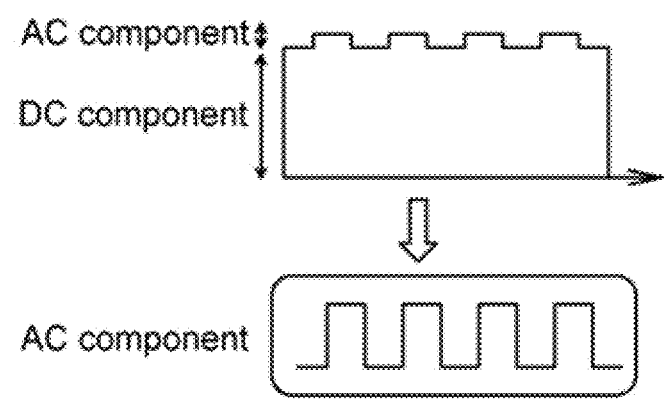
FIG. 14 shows a schematic image diagram of a composite rectangular wave transmitted light according to the embodiment of the present invention.

The composite rectangular wave measurement light ML3 acquired from the first measurement light ML1 and the second measurement light ML2 is acquired as a quasi-rectangular wave having a DC component and an AC component. Then, the composite rectangular wave measurement light ML3 transmitted through the plant sample S is detected by the transmitted light detector 18 (see FIG. 1) as the composite rectangular wave transmitted light TL (see FIG. 14). As shown in FIG. 14, the composite rectangular wave transmitted light TL includes the DC component and the AC component. The AC component of this composite rectangular wave transmitted light TL corresponds to the dual-wavelength light absorption difference between the first measurement light ML1 and the second measurement light ML2 transmitted through the plant sample S.

That is, in the present embodiment, the two transmitted lights transmitted through the plant sample S can be detected with the single transmitted light detector 18. Thus, the stress diagnosis device 10 according to the present embodiment can be miniaturized because components can be reduced than in conventional products.

The transmitted light detector 18 detects the composite rectangular wave transmitted light TL as a rectangular wave of 10 kHz having slight unevenness (the AC component) on the DC component (FIG. 14). In the present embodiment, the DC component can be removed by utilizing AC coupling, for example, to detect the AC component alone. Then, by amplifying this AC component with an amplifier, a sufficient dynamic range can be ensured (even a minute signal change can be sufficiently magnified and gauged).

In addition, in the present embodiment, by utilizing this composite rectangular wave measurement light ML3 (the composite rectangular wave transmitted light TL), a noise reduction effect can also be expected as compared with the case of detecting the dual-wavelength light absorption difference by utilizing the first measurement light ML1 and the second measurement light ML2 as in the conventional measurement. Further, even in a case in which a base line changes irregularly in measurement of ML1 and ML2, a difference between minute changes in dual-wavelength absorption can be calculated at a high S/N ratio by performing the lock-in amplifier signal processing by utilizing the composite rectangular wave measurement light ML3.

Here, the composite rectangular wave measurement light ML3 can be acquired by making the second measurement light ML2 to have higher power than the first measurement light ML1 (specifically, have slightly higher power in the range of approximately 1% to 5%) and subjecting the first measurement light ML1 and the second measurement light ML2 as opposite-phase rectangular waves to synchronous control, as described above. However, very high-speed light source output waveform control (a frequency of 5 kHz to 30 kHz) is actually performed, and LED control currents for the first measurement light ML1 and the second measurement light ML2 are variably adjusted depending on the difference in absorption in a sample to be measured.

Thus, a settling time differs depending on the set currents (the LED control currents), so that the first measurement light ML1 and the second measurement light ML2 may overlap (the first measurement light ML1 and the second measurement light ML2 may lose synchronization, or the composite waveform may be deformed). In the present embodiment, the settling time (fall time) is several tens to several hundreds of nanoseconds. In the case of such high-speed control, the composite rectangular wave measurement light ML3 can no longer be acquired when synchronization is lost even slightly.

Hence, in addition to the control of forming the composite rectangular wave measurement light ML3, the control circuit 20b according to the present embodiment further performs control (synchronous control) for loss of synchronization between the first measurement light ML1 and the second measurement light ML2 simultaneously.

Figure 15:
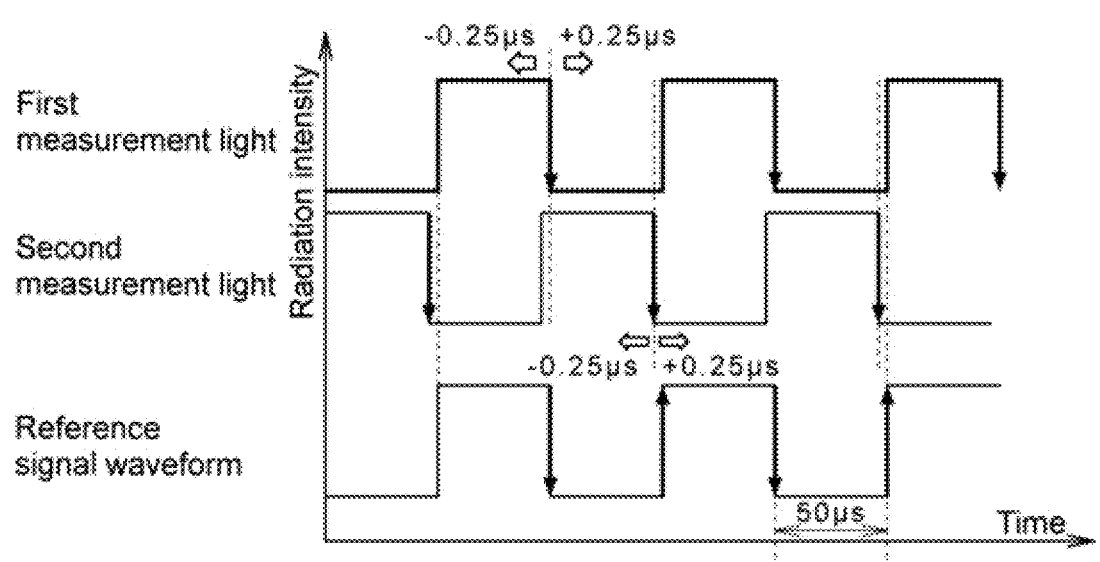
FIG. 15 shows a schematic explanatory diagram of synchronous control according to the embodiment of the present invention.

FIG. 15 shows a schematic explanatory diagram of synchronous control according to the present embodiment. As shown in FIG. 15, the control circuit 20b monitors rising and falling timings of the rectangular waves in the first measurement light ML1 and the second measurement light ML2 as well as a reference signal as a command frequency when adjusting the measurement light source at the start of measurement. Then, the control circuit 20b compares the falling timings of the rectangular waves in ML1 and ML2 with a reference signal waveform.

Herein, the control circuit 20b can synchronize the rising timings in the first measurement light ML1 and the second measurement light ML2. On the other hand, the falling timings in the first measurement light ML1 and the second measurement light ML2 might lose synchronization due to outputs (such as output currents) of the measurement light source 12 depending on the transmittance of the sample or the like (the ways in which the rectangular waves fall are actually different depending on the difference between output values). For example, the first measurement light ML1 and the second measurement light ML2 may have different falling timings depending on the difference between output values of the first measurement light ML1 and the second measurement light ML2.

Hence, in the case in which the falling timings of the first measurement light ML1 and the second measurement light ML2 lose synchronization, the control circuit 20b according to the present embodiment adjusts the falling timings in a unit of 0.25 μs (−0.25 μs to +0.25 μs) to maintain synchronization. Specifically, the control circuit 20b compares the falling timings of the rectangular waves in the first measurement light ML1 and the second measurement light ML2 with the reference signal waveform as the command frequency. Then, in the case in which the falling timings in the first measurement light ML1 and the second measurement light ML2 lose synchronization due to the outputs from the measurement light source 12, the control circuit 20b adjusts the falling timings in the unit of 0.25 μs to maintain synchronization.

The control circuit 20b synchronizes the mutual rising timings of the respective rectangular waves in the first measurement light ML1 and the second measurement light ML2 output from the measurement light source 12 by PWM control with a delay of a half cycle. Then, as to the falling timings in the first measurement light ML1 and the second measurement light ML2, loss of synchronization in the timings (the overlapping degree of the two measurement lights) due to the difference between the fall times caused by the difference between measurement light intensities can be adjusted in the unit of 0.25 μs.

In this manner, the present embodiment also copes with loss of synchronization that may inevitably occur in measurement light control, thus a stable composite rectangular wave measurement light can be obtained. As a result, an accurate environmental stress diagnosis can be achieved.

Regarding Ros Marker (Reactive Oxygen Species Suppression Index)

Here, the ROS marker in the present embodiment is described. The environmental stress diagnosis device 10 according to the present embodiment diagnoses environmental stress in plants more accurately and earlier than in the conventional measurement by utilizing a correlation between the ROS marker and the oxygen production rate (or the photosynthesis rate Y(II) calculated from V(O$_2$)). That is, although an environmental stress diagnosis for plants has conventionally been performed only with the photosynthetic activity in the photosystem II or the like, the present embodiment also analyzes the state of P700 in the photosystem I further in addition to the photosystem II (or the oxygen production rate) to perform a diagnosis.

Figure 16:
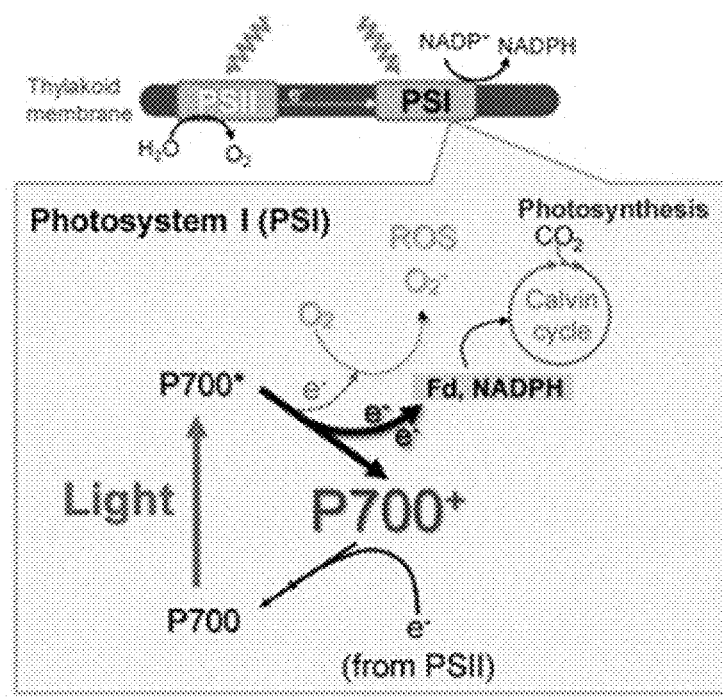
FIG. 16 shows a schematic explanatory diagram of an induction principle of a ROS marker (Y(ND)).

FIG. 16 shows a schematic explanatory diagram of an induction principle of the ROS marker (Y(ND)) according to the present embodiment. When exposed to environmental stress, $CO_2$ fixation through photosynthesis is suppressed in plants. Recent research has revealed that production of reactive oxygen species (ROS) can be avoided by appropriately suppressing supply of electrons from the photosystem II (also called PSII).

In plants, P700 (reaction center chlorophyll of the photosystem I) takes three states of P700(Y(I)) having been reduced and being in the ground state, P700*(Y(NA)) which is the state absorbing light energy, and P700+(Y(ND)) which is the state having emitted light energy to be oxidized, and has a relation of Y(I)+Y(NA)+Y(ND)=1.

When P700 is in the state of Y(I) or Y(NA) having electrons, the risk of ROS production increases. On the other hand, when P700 is in the state of Y(ND) having no electrons, ROS production is suppressed. In other words, whether ROS production is suppressed in plants can be determined from an abundance ratio of Y(ND), that is, the environmental stress state in plants can be identified non-destructively and early.

Specifically, when electrons from the photosystem II is supplied, P700 in the photosystem I (also called PSI) is oxidized to be P700+. By detecting this P700+(Y(ND)), the danger of ROS production due to photosynthesis deterioration can be detected in an early stage. In the present embodiment, this (Y(ND)) is called the ROS marker as the reactive oxygen species suppression index.

Regarding Correlation Between ROS Marker and Oxygen Production Rate

Next, a correlative relationship between the ROS marker (Y(ND)) and the oxygen production rate (photosynthesis rate) according to the present embodiment is described. As described above, the environmental stress diagnosis device 10 according to the present embodiment comprises the oxygen concentration detector 22 together with the transmitted light detector 18, and calculates the correlation between the ROS marker and the oxygen production rate by the analysis circuit 20a, thereby performing an environmental stress diagnosis for plants more accurately and earlier than in the conventional measurement.

Figure 17:
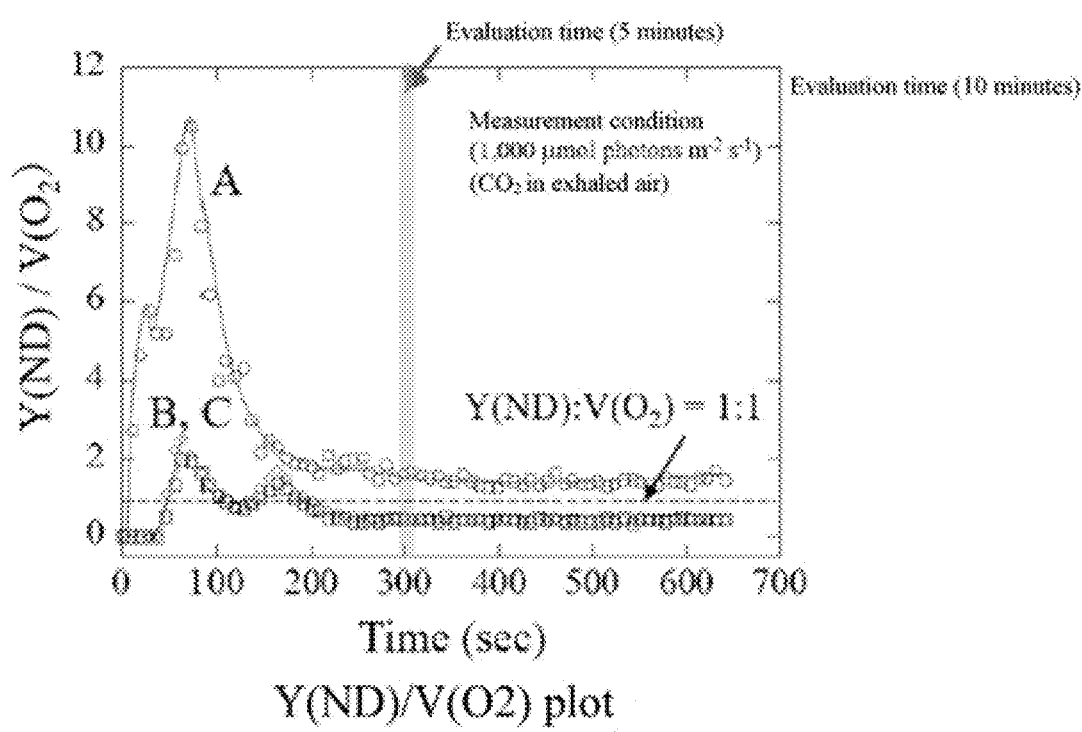
FIG. 17 shows an example of relationship between the ROS marker and an oxygen production rate in the present embodiment.

FIG. 17 shows an example of relationship between the ROS marker and the oxygen production rate. FIG. 17 shows results of measuring and analyzing plant samples in respective fields of a field A (in which a plant (wheat) subject to environmental stress is grown; A in FIG. 17), a field B (in which a plant (wheat) not subject to environmental stress is grown; B in FIG. 17), and a field C (in which a plant (wheat) not subject to environmental stress is grown; C in FIG. 17).

As shown in FIG. 17, in the field A in which the plant subject to environmental stress is grown, Y(ND)/V(O$_2$) has a large numeric value. On the other hand, in the field B and the field C in which the plants not subject to environmental stress are grown, this numeric value is smaller than in the field A. In this manner, by identifying the relationship between the ROS marker (Y(ND)) and the oxygen production rate (V(O$_2$)), the environmental stress state of the plants can be diagnosed accurately.

Figure 18:
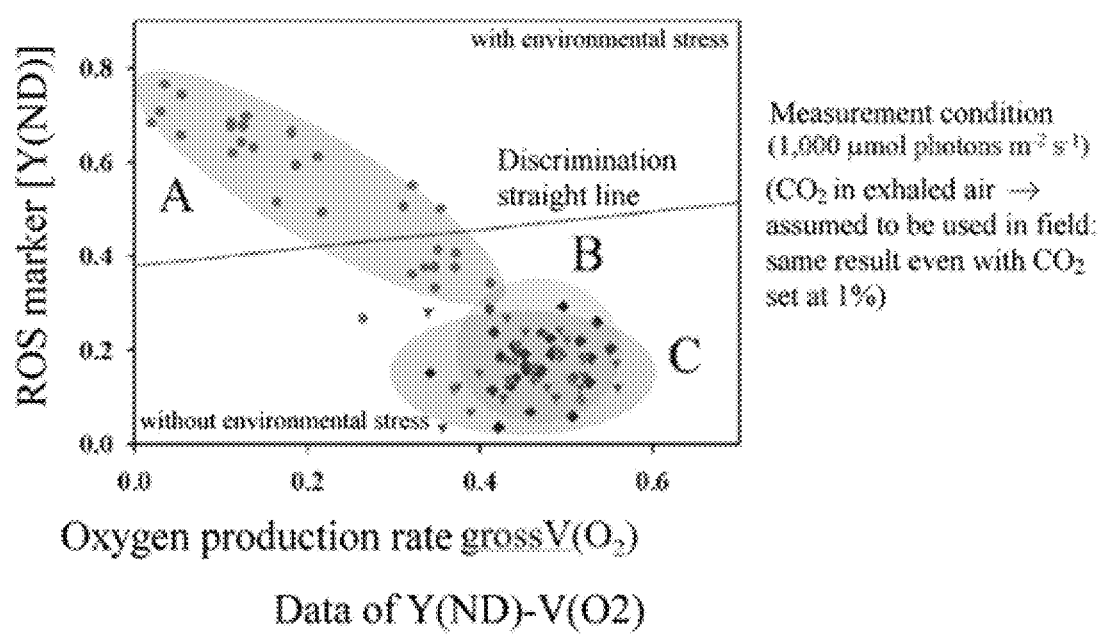
FIG. 18 shows an image diagram of correlation between the ROS marker and the oxygen production rate in the present embodiment.

In addition, FIG. 18 shows an image diagram of the correlation between the ROS marker and the oxygen production rate in the present embodiment. A, B, and C in FIG. 18 indicate A (the field A), B (the field B), and C (the field C) in FIG. 17. A straight line at the center of FIG. 18 is a discrimination straight line for discriminating whether plants are subject to environmental stress or not.

As shown in FIG. 18, it is understood that measurement results of the field A (in which the plant subject to environmental stress is grown) concentrate on the upper side of the discrimination straight line (diagnosed as being subject to environmental stress), whilst measurement results of the field B and the field C concentrate on the lower side of the discrimination straight line (diagnosed as not being subject to environmental stress). In other words, FIG. 18 indicates that an accurate environmental stress diagnosis result is acquired by utilizing the correlation between the ROS marker and the oxygen production rate.

According to the present invention, the composite rectangular wave measurement light ML3 is formed by the control circuit 20b (making ML2 to have higher power than ML1 and performing synchronous control over ML1 and ML2 as opposite-phase rectangular waves), and the composite rectangular wave transmitted light TL through the plant sample S stored in the sealed chamber 16 (the ROS marker is calculated by the analysis circuit 20a) and the oxygen production rate are simultaneously gauged by utilizing the oxygen concentration detector 22 together with the transmitted light detector 18. Further, by performing an environmental stress diagnosis utilizing the correlation between the ROS marker and the oxygen production rate by the analysis circuit 20a, the environmental stress diagnosis device 10 that can diagnose an environmental stress state of plants more accurately and earlier than in the conventional chlorophyll fluorescence measurement can be acquired.

In addition, although the diagnosis device for environmental stress in plants has been described in the present embodiment, an environmental stress diagnosis can be performed more accurately and earlier than in the conventional measurement by performing steps similar to those of the present device, for example.

Specifically, a step of storing a plant sample in the sealed chamber, adjusting, by the control circuit, the first measurement light and the second measurement light that are output from the measurement light source, and adjusting the first photosynthesis inducing light and the second photosynthesis inducing light to be output from the induction light source is performed first.

Thereafter, a step of controlling the measurement light source by the control circuit such that the second measurement light has higher power than the first measurement light and the first measurement light and the second measurement light become opposite-phase rectangular waves, controlling the measurement light source by the control circuit such that the first measurement light and the second measurement light are output in synchronization to form the first measurement light and the second measurement light into a quasi-single composite rectangular wave measurement light of 5 kHz to 30 kHz including a DC component, and radiating the composite rectangular wave measurement light together with the first photosynthesis inducing light and the second photosynthesis inducing light to the plant sample is performed.

Thereafter, a step of detecting the composite rectangular wave measurement light transmitted through the plant sample as a composite rectangular wave transmitted light by a transmitted light detector is performed. Then, a step of calculating, by an analysis circuit, a light absorption difference between the first measurement light and the second measurement light transmitted through the plant sample by utilizing the composite rectangular wave transmitted light, and calculating, by the analysis circuit, Y(ND) which is the state in which P700 in the photosystem I has been oxidized in photosynthesis as the ROS marker which is the reactive oxygen species suppression index for plants by utilizing the light absorption difference is performed. Finally, a step of diagnosing an environmental stress state of the plants by utilizing the ROS marker is performed. Thus, an environmental stress diagnosis can be performed more accurately and earlier than in the conventional measurement.

Figure 19:
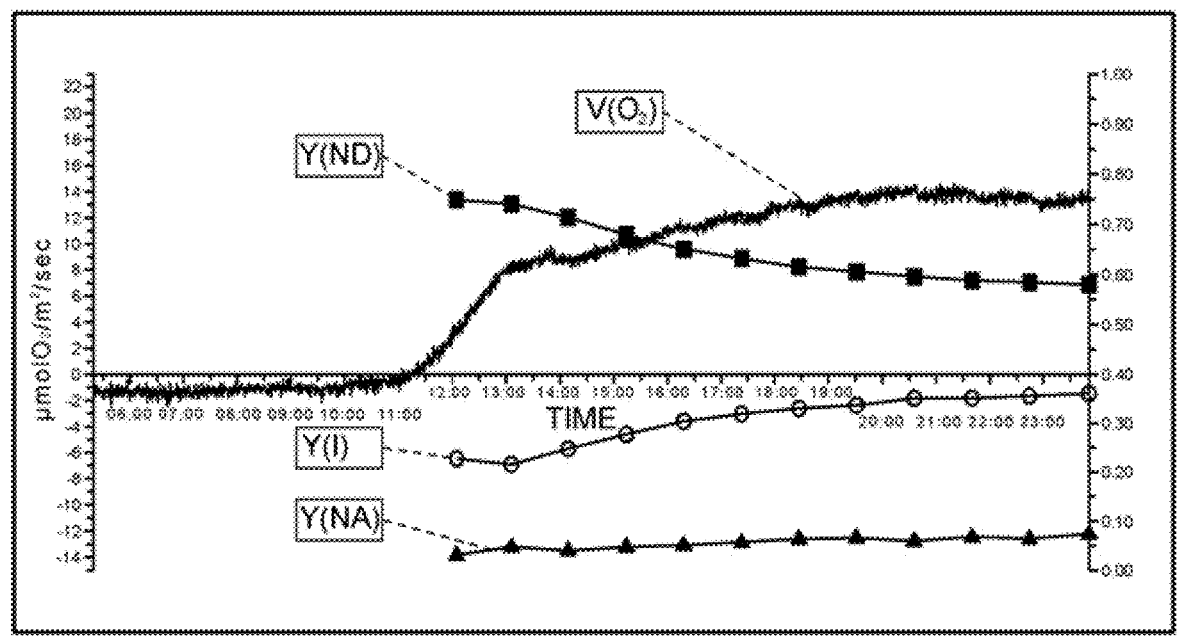
FIG. 19 shows a measurement example of Y(ND), Y(I), Y(NA), and V(O2).

In addition, the environmental stress diagnosis device 10 according to the present embodiment can also calculate Y(I) and Y(NA) together with Y(ND) and the oxygen production rate V(O2) as shown in FIG. 19, for example. By combining these other parameters as well, an optimum analysis (environmental stress diagnosis) can be performed.

Regarding Diagnosis of Mineral Nutrient Stress

As described above, the present embodiment performs an environmental stress diagnosis by utilizing measurement information about the photosystem I (mainly the ROS marker) and the oxygen production rate (or the photosynthesis rate). In addition, the inventors of the present invention have found out that mineral nutrient stress in plants can be diagnosed by utilizing other types of measurement information in the photosystem II together with the measurement information about the photosystem I.

Figure 20:
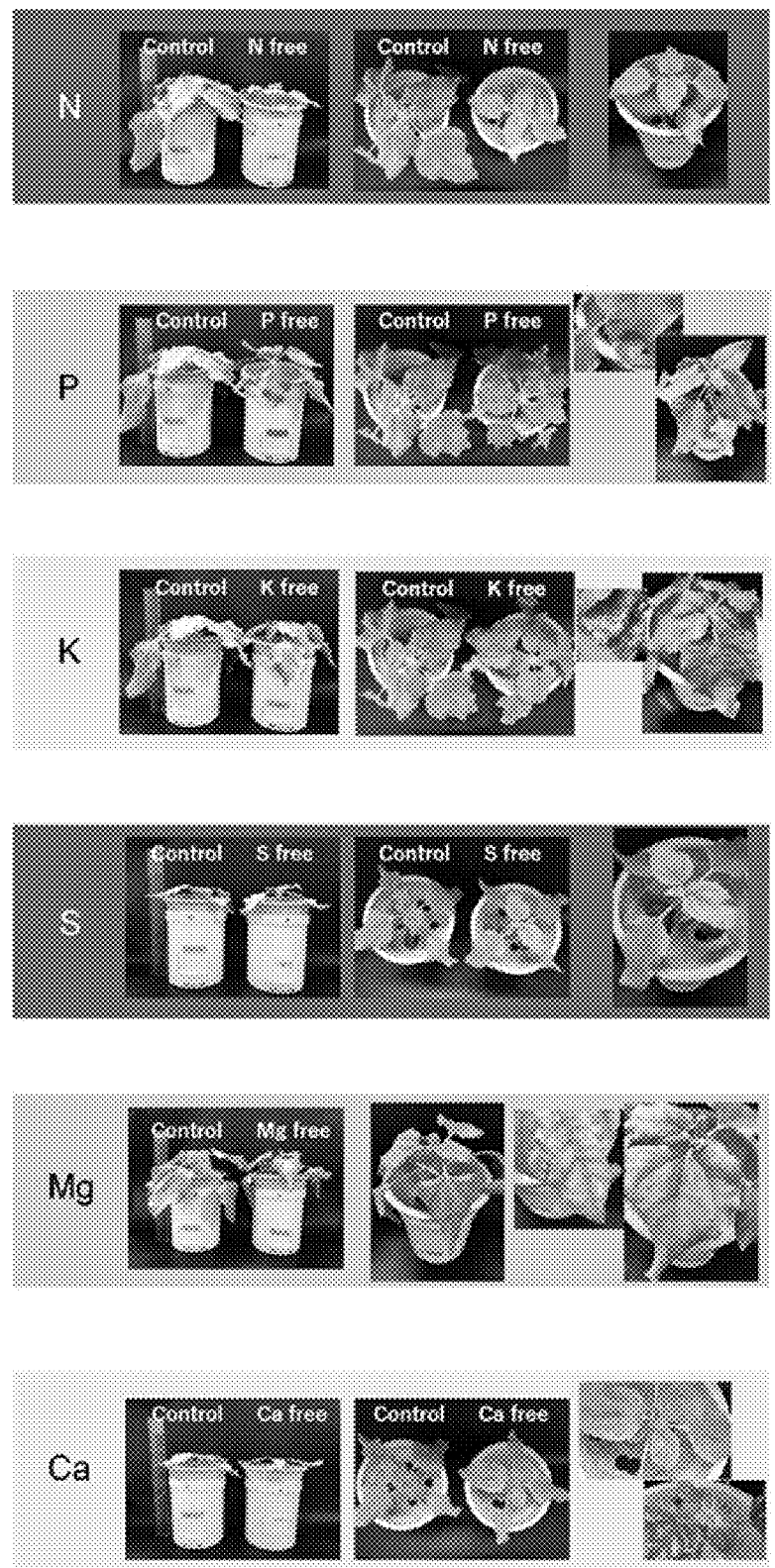
FIG. 20 shows comparative image views of plants (control) in a state in which mineral nutrients are normal and plants (free) in a state deficient in mineral nutrients.
Figure 21:
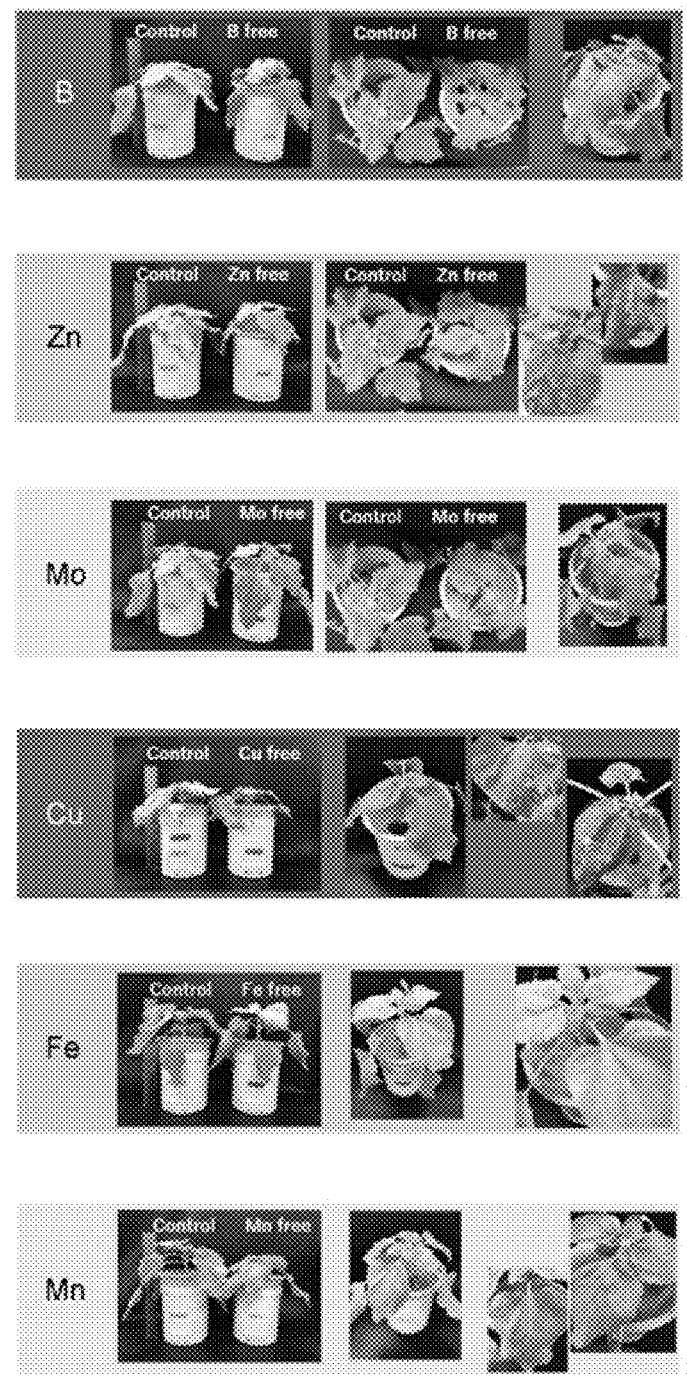
FIG. 21 shows comparative image views of plants (control) in the state in which mineral nutrients are normal and plants (free) in the state deficient in mineral nutrients.

FIG. 20 and FIG. 21 show comparative image views of plants (control) in a state in which mineral nutrients are normal and plants (free) in a state deficient in mineral nutrients. The mineral nutrients in the present description refer to other elements except C, O, and H among essential nutrients for plants. FIG. 20 shows comparative images of N, P, K, S, Mg, and Ca which are essential nutrients for plants. In addition, FIG. 21 shows comparative images of B, Zn, Mo, Cu, Fe, and Mn.

FIG. 20 and FIG. 21 shows comparison of growth of sunflowers. Specifically, sunflowers were grown for two weeks, and then, the concentration of each of the mineral nutrients was changed. Then, growth of each sunflower was compared one week later. In the following, measurement results and the like acquired when living leaves of sunflower were used as the plant sample S is indicated.

As shown in FIG. 20 and FIG. 21, it is understood that lack of mineral nutrients largely affects the growth of plants. In the present embodiment, a deficient state of mineral nutrients can be found early by detecting various parameters of the photosystem I and the photosystem II. The diagnosis of mineral nutrient stress in plants can be expected to achieve an effect of reducing mismatch in a period of applying an additional fertilizer and resultantly ensuring stable harvesting of the plants, for example.

Figure 22:
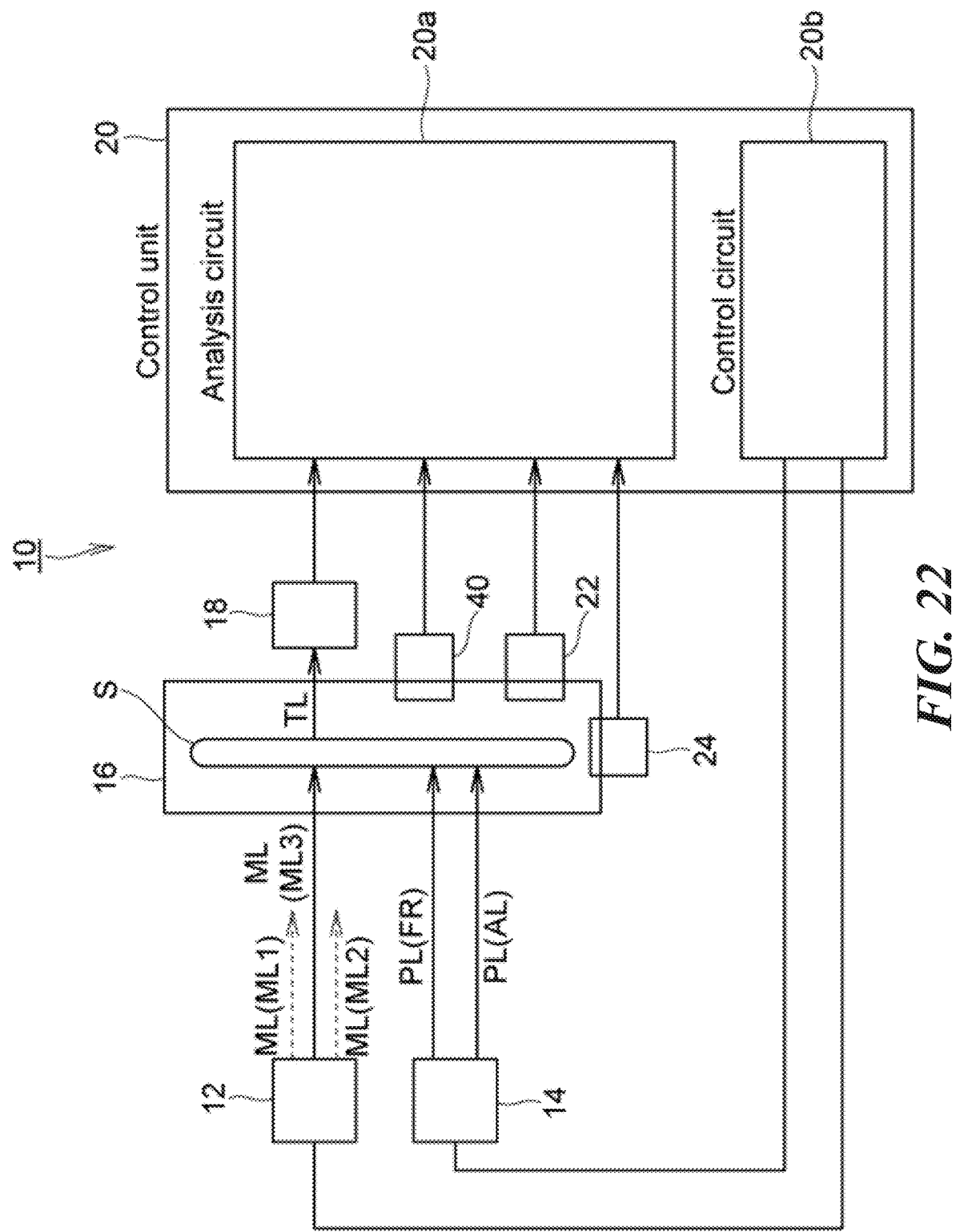
FIG. 22 shows a schematic configuration diagram in a case of performing chlorophyll fluorescence measurement in an environmental stress diagnosis device 10 according to the present embodiment.

As described above, the environmental stress diagnosis device 10 according to the present embodiment mainly measures the ROS marker and the oxygen production rate, and can achieve a mineral nutrient stress diagnosis by additionally measuring chlorophyll fluorescence. FIG. 22 shows a schematic configuration diagram in the case of performing the chlorophyll fluorescence measurement in the environmental stress diagnosis device 10 according to the present embodiment. In FIG. 22, components common to those of the environmental stress diagnosis device 10 shown in FIG. 1 and FIG. 7 are described with the same reference numerals.

As shown in FIG. 22, the environmental stress diagnosis device 10 is equipped with a fluorescence detector 40 for measuring chlorophyll fluorescence in addition to the transmitted light detector 18 and the oxygen concentration detector 22 (and the environment sensor 24). In the present embodiment, to perform the chlorophyll fluorescence measurement, a 450 nm LED, for example, can be utilized as a light source. In the present embodiment, the 450 nm LED can be added to the induction light source 14, for example.

In this manner, by measuring the chlorophyll fluorescence together with the ROS marker and the oxygen production rate and analyzing an obtained chlorophyll fluorescence detection result, a further specific environmental stress diagnosis, for example, a diagnosis of mineral nutrient stress in plants, can be performed.

Figure 23:
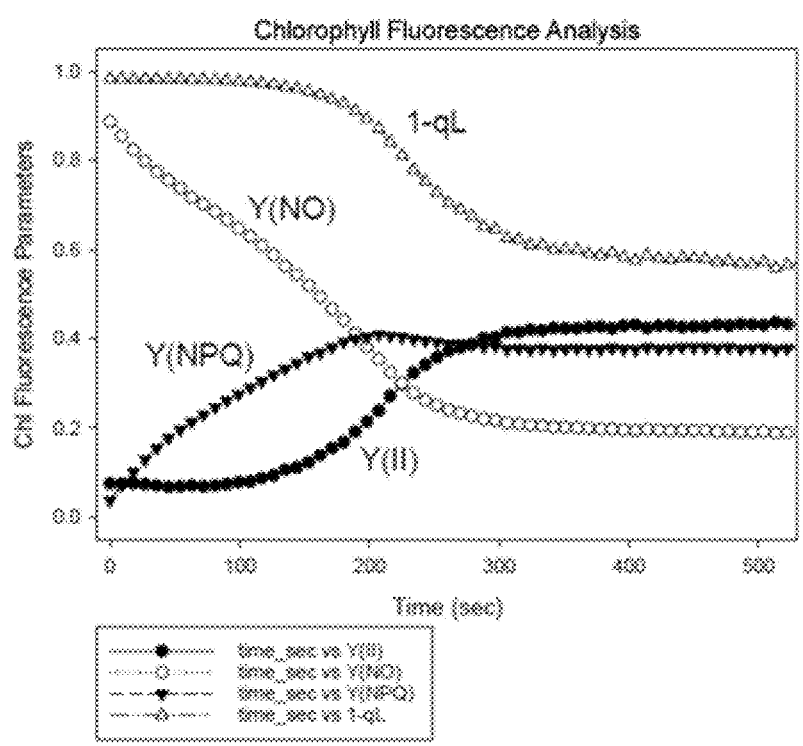
FIG. 23 shows a schematic image diagram of each parameter in chlorophyll fluorescence detection.

The analysis circuit 20a in FIG. 22 can calculate Y(II) as the photosynthesis rate, Y(NPQ) as light energy that cannot be utilized for photosynthesis, Y(NO) as fundamental heat dissipation performance in the photosystem II, and 1-pL as a plastoquinone reduction rate by utilizing the chlorophyll fluorescence detection result acquired by the fluorescence detector 40 (FIG. 23).

Figure 24:
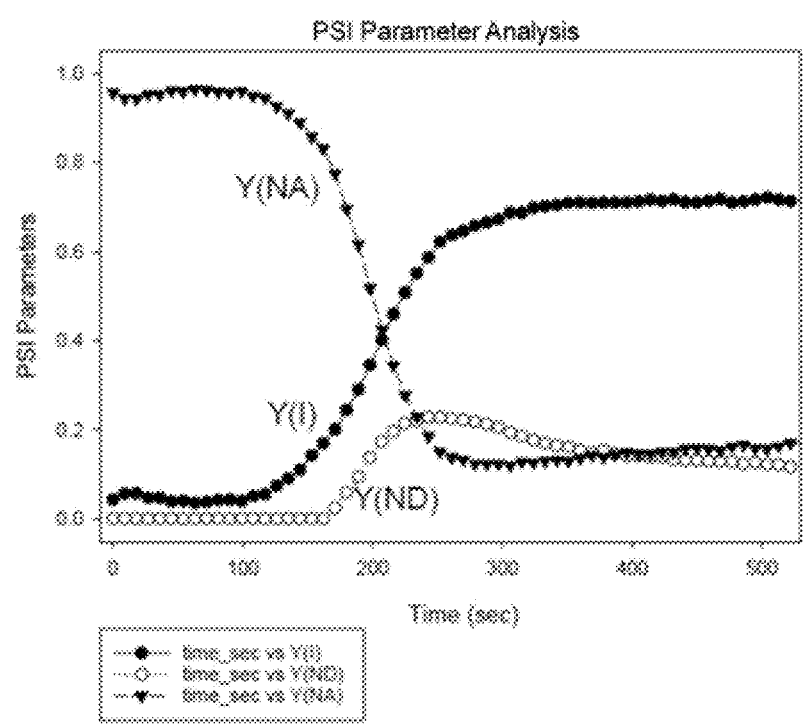
FIG. 24 shows a schematic image diagram of each parameter in the photosystem I.
Figure 25A:
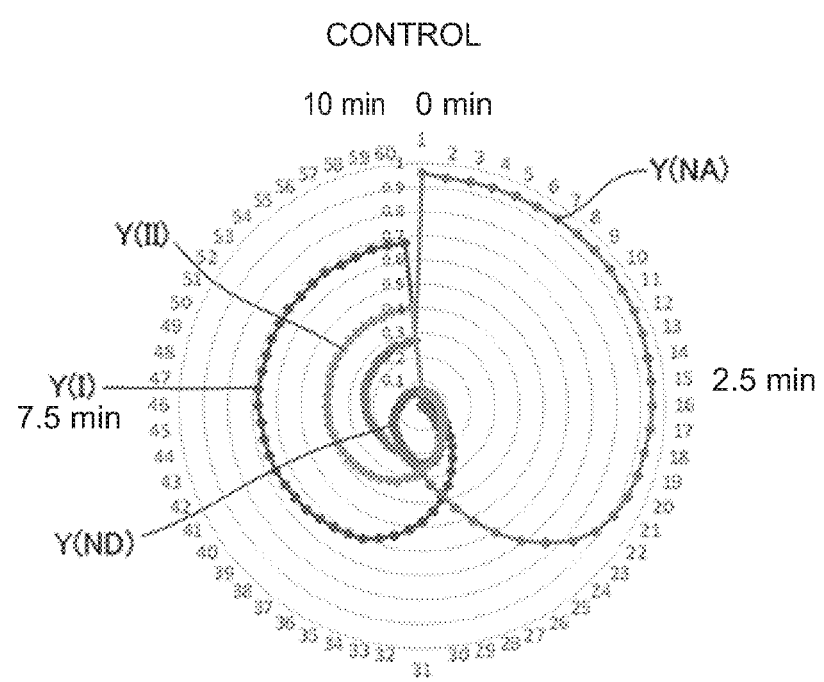
FIG. 25 shows an example of measurement result graphs in which the elapse of time is expressed circularly and Y(I), Y(ND), Y(NA), and Y(II) are plotted.
Figure 25B:
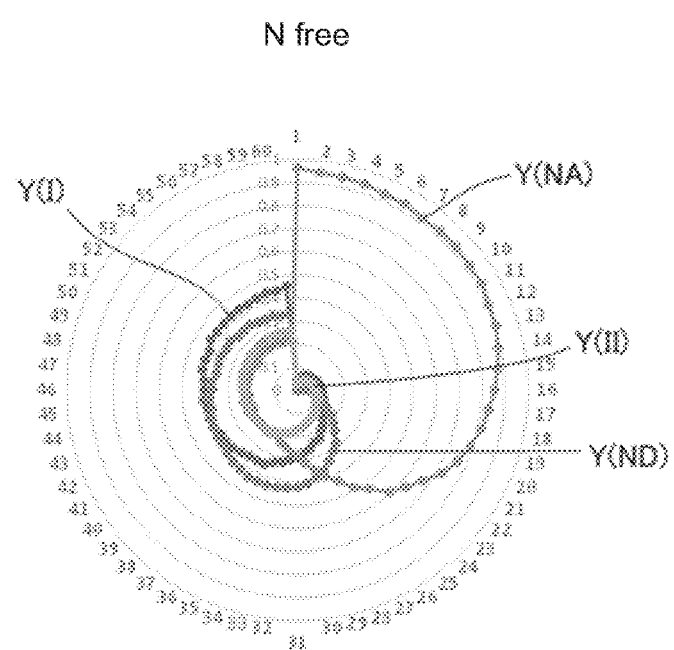
Figure 25C:
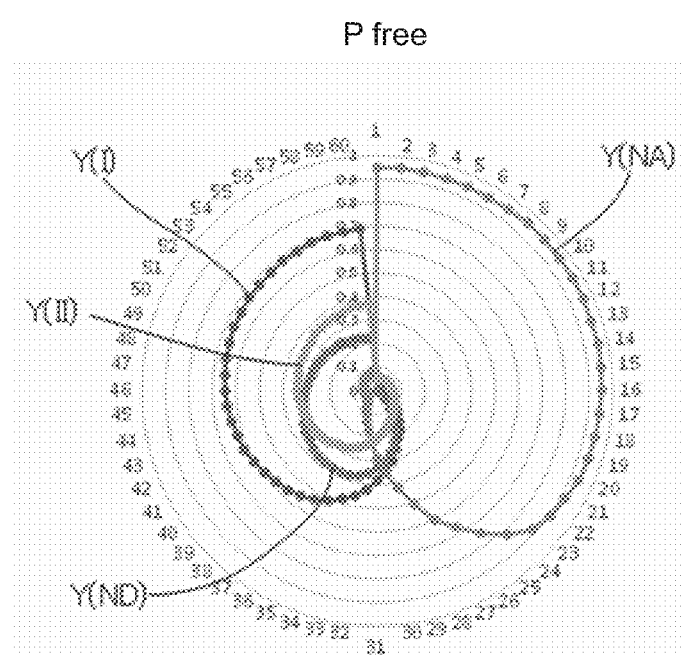
Figure 25D:
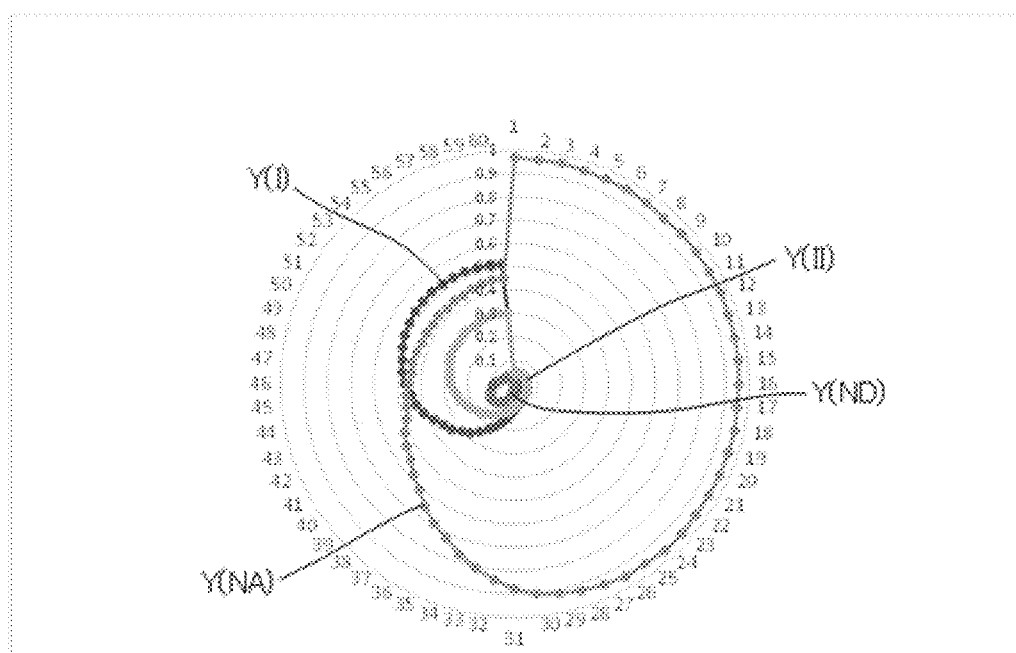
Figure 25E:
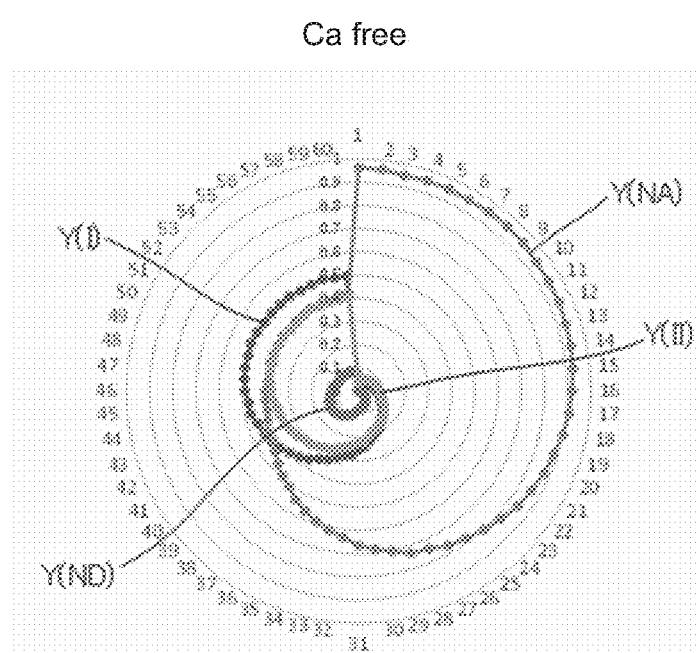
Figure 25F:
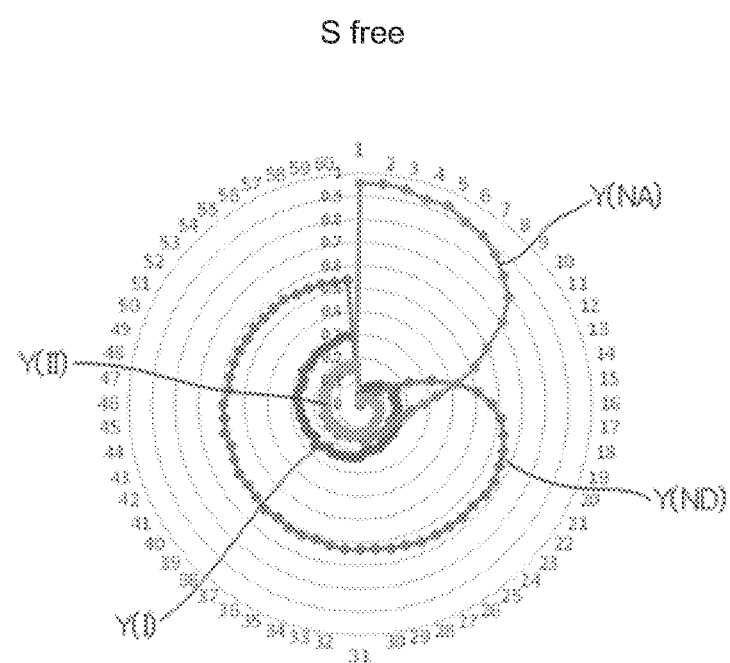
Figure 25G:
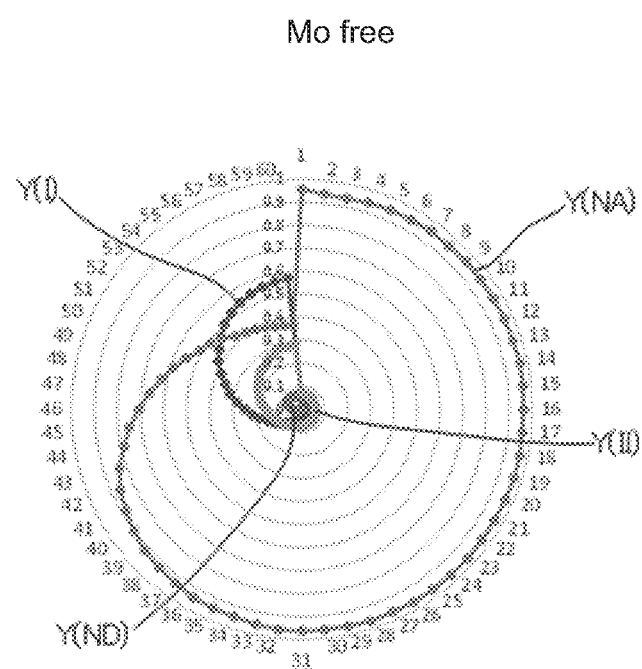
Figure 25H:
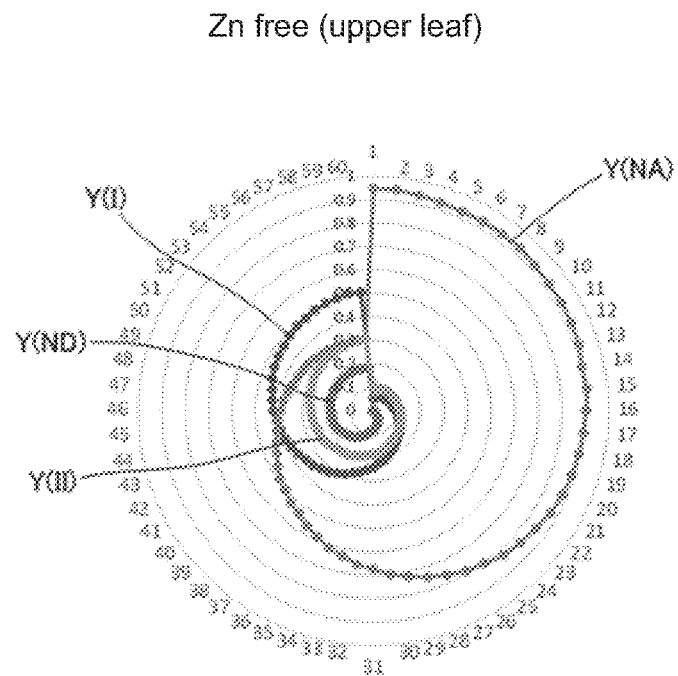
Figure 25I:
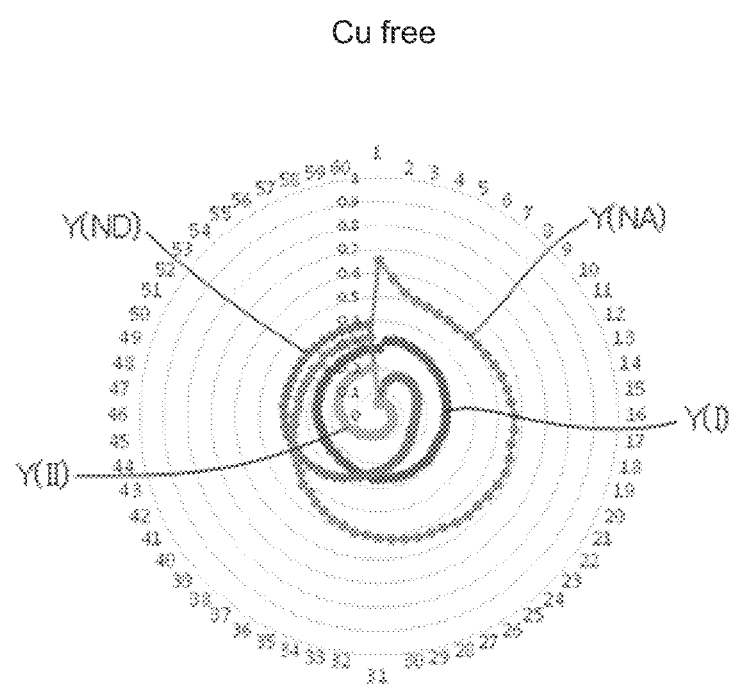
Figure 25J:
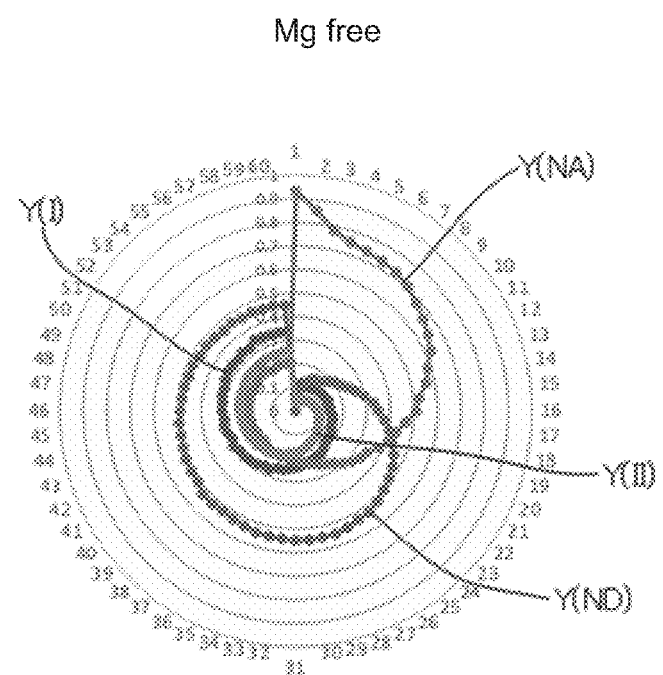
Figure 25K:
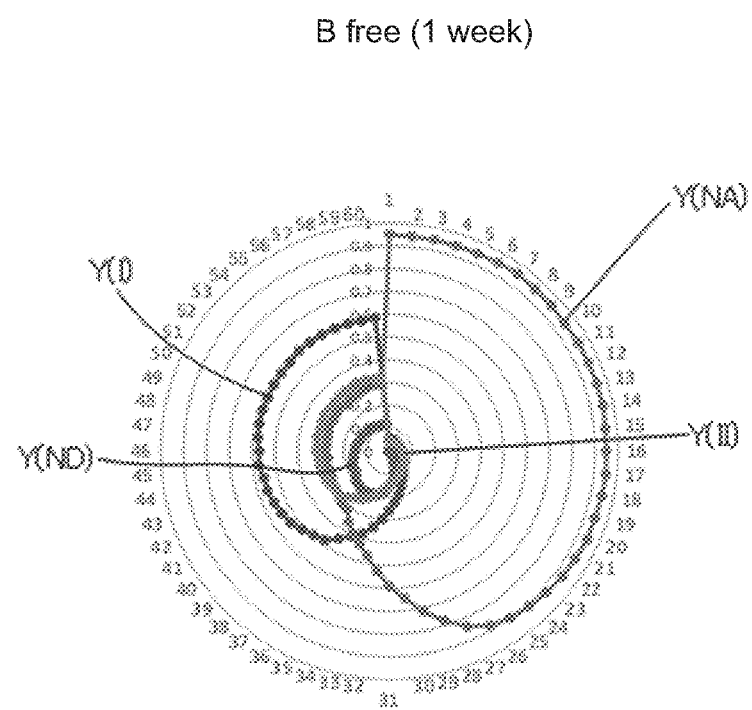
Figure 25L:
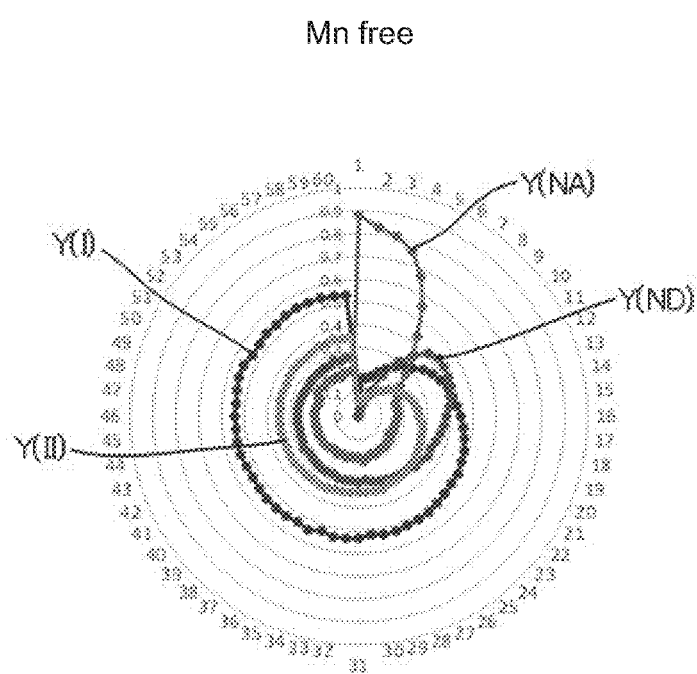
Figure 25M:
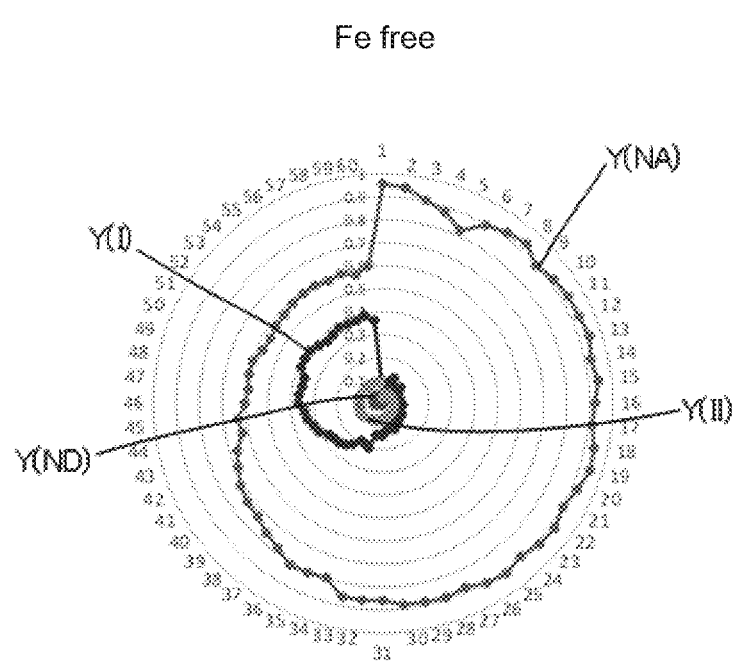
Figure 26A:
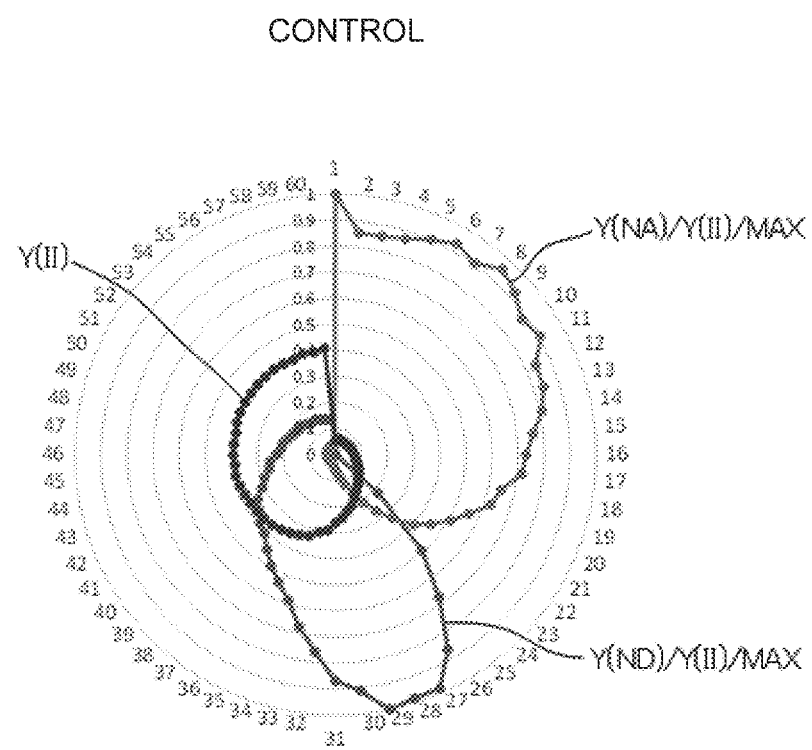
FIG. 26 shows an example of measurement result graphs showing values acquired by dividing Y(I), Y(ND), and Y(NA) by Y(II).
Figure 26B:
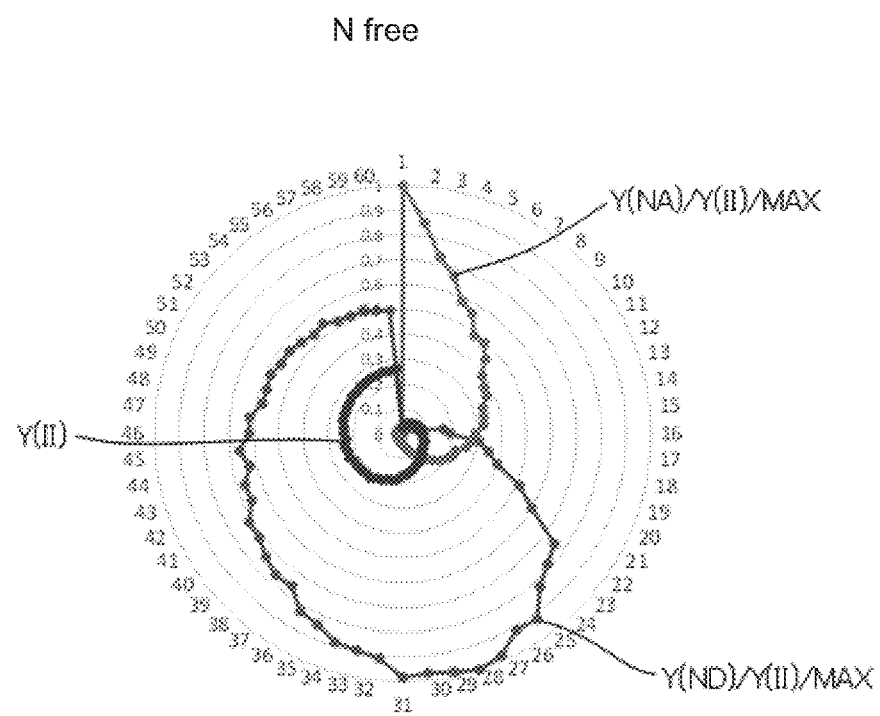
Figure 26C:
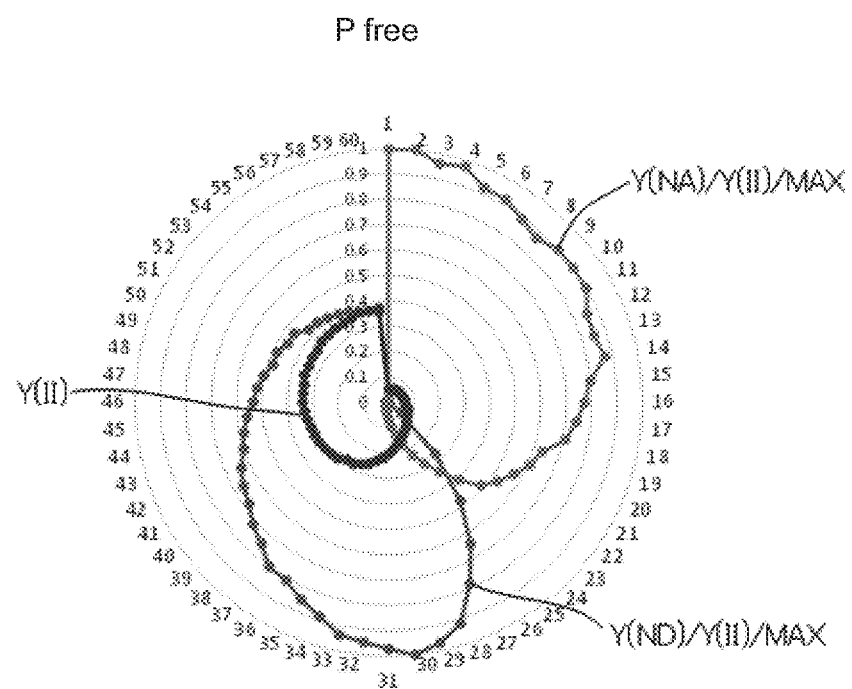
Figure 26D:
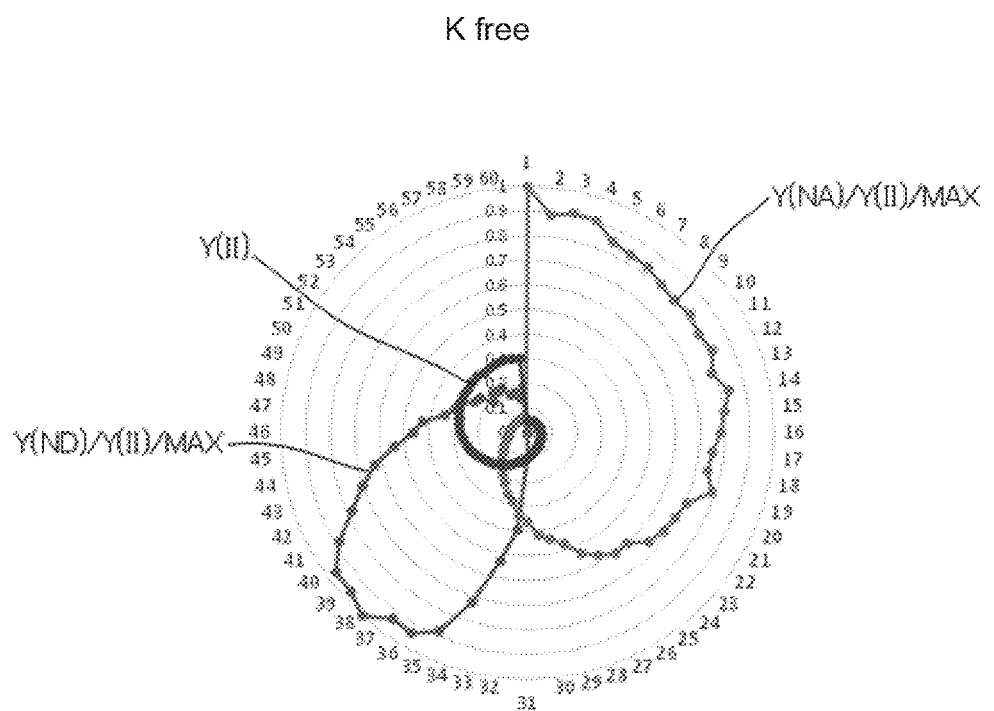
Figure 26E:
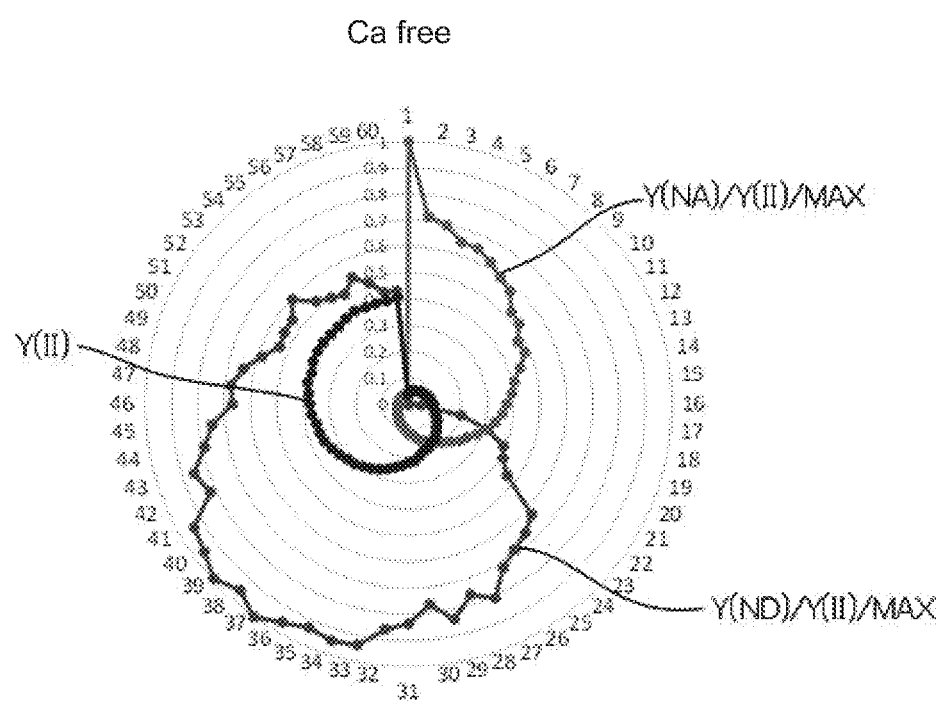
Figure 26F:
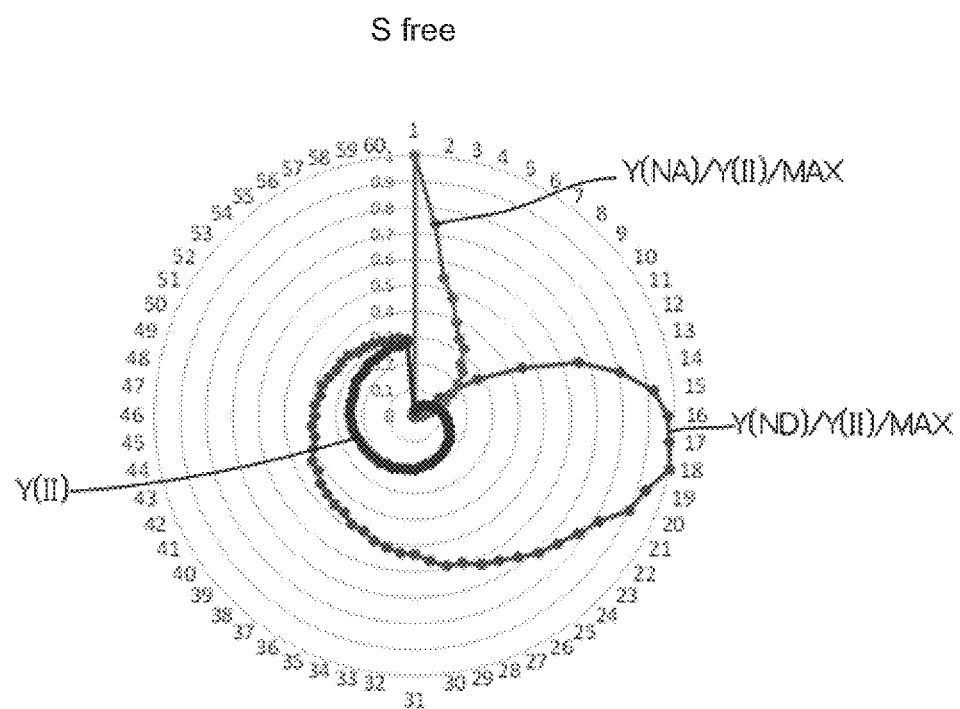
Figure 26G:
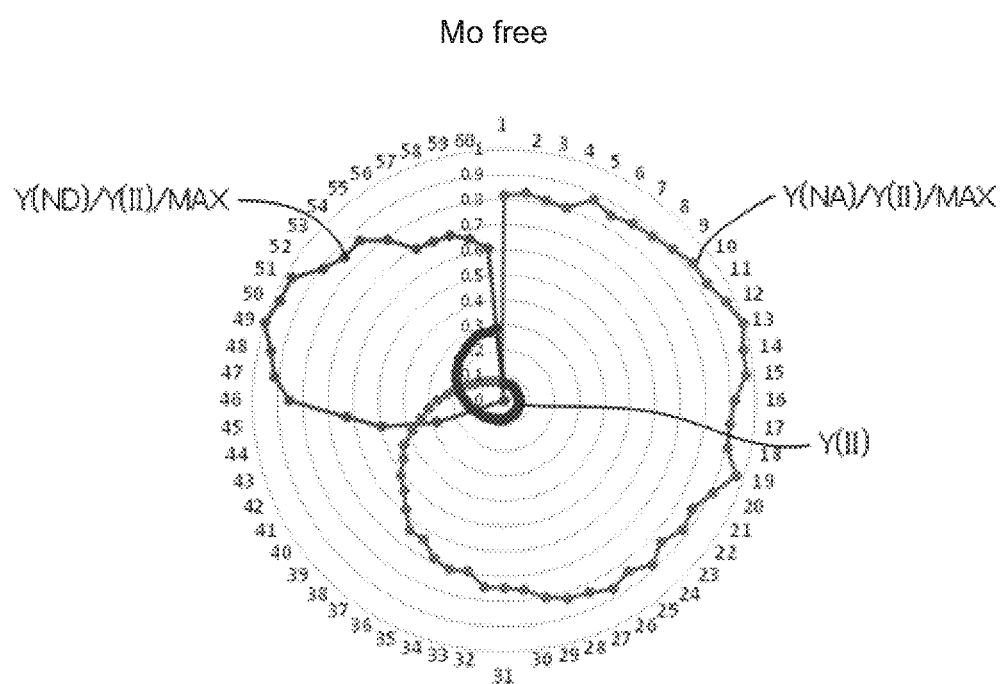
Figure 26H:
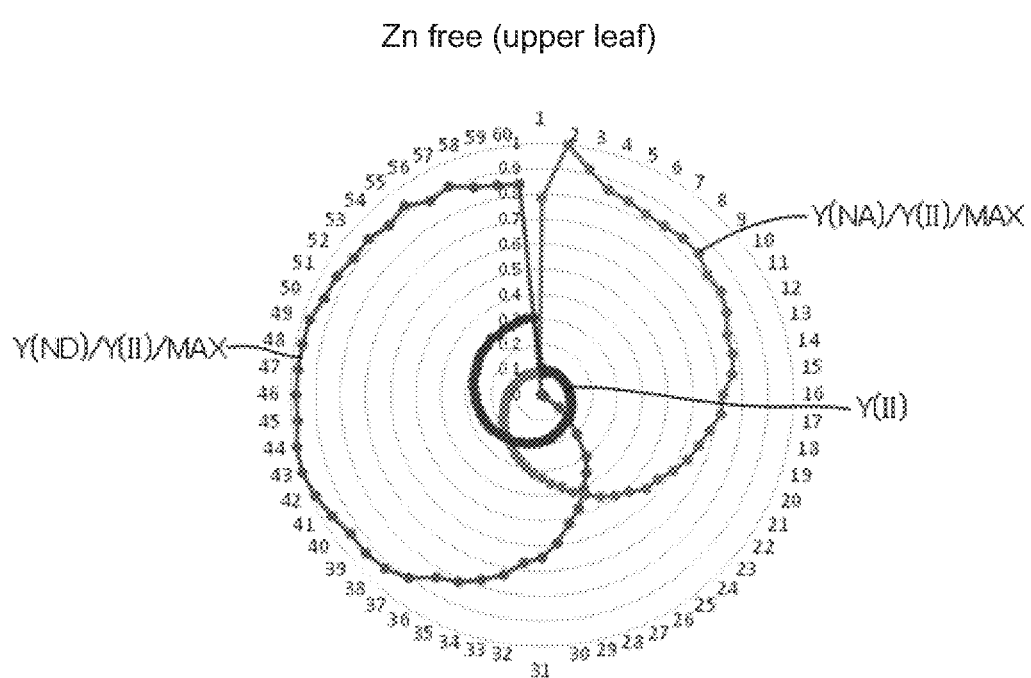
Figure 26I:
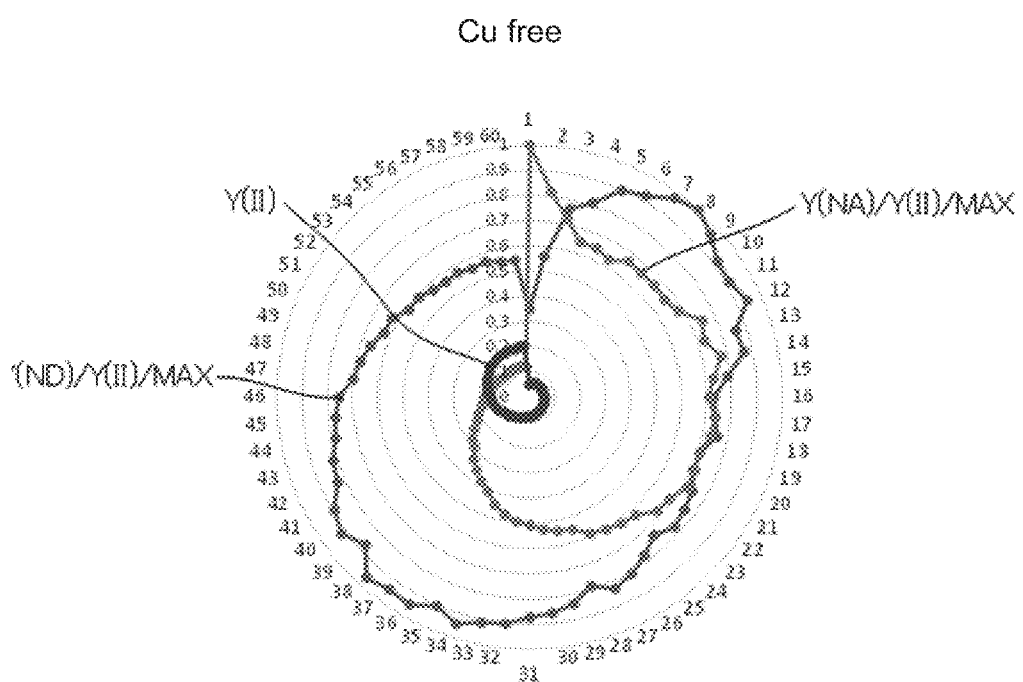
Figure 26J:
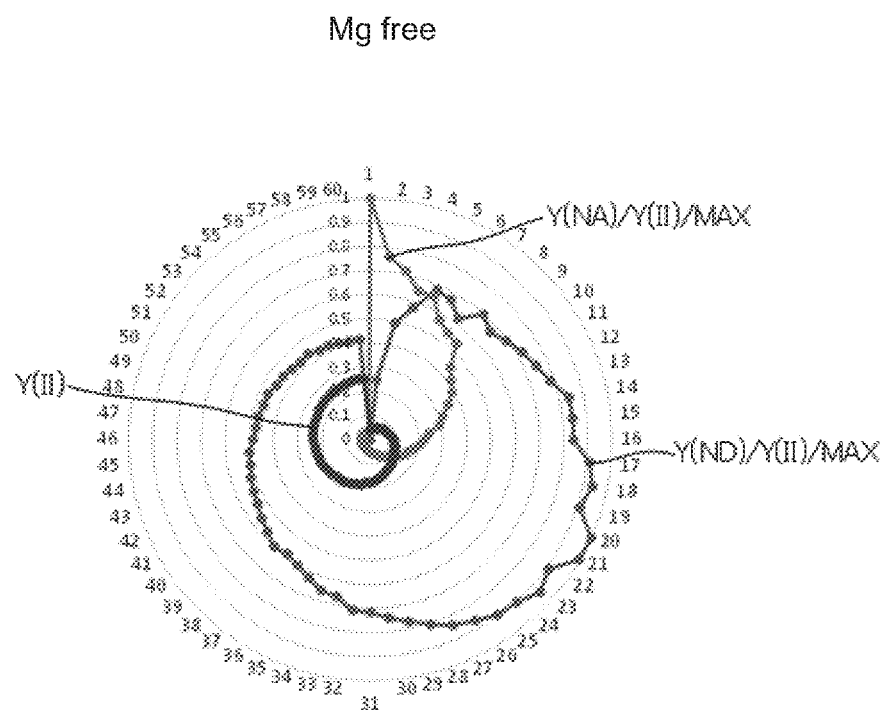
Figure 26K:
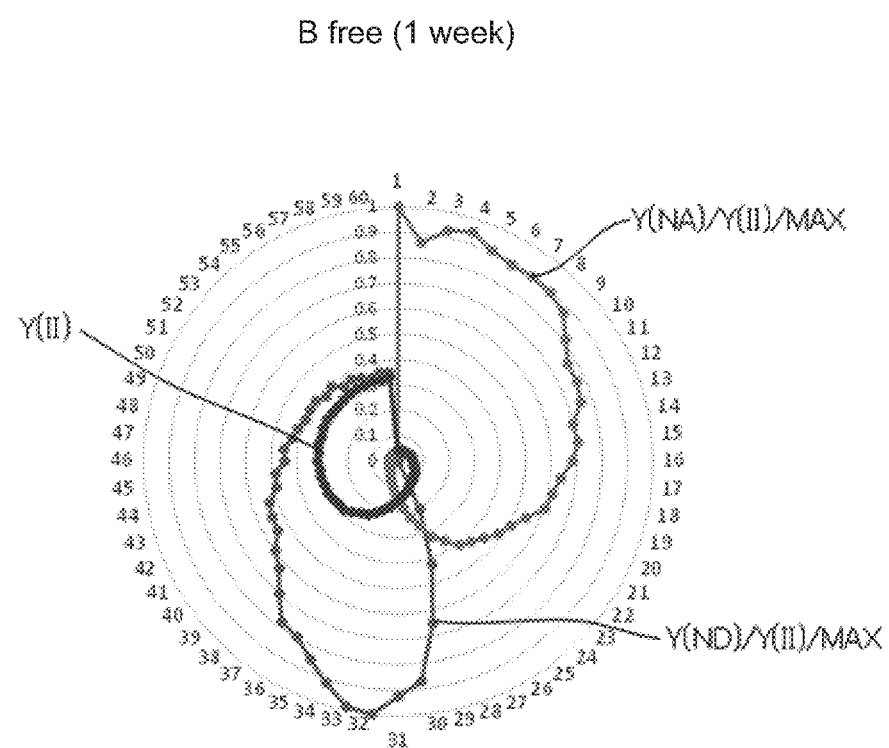
Figure 26L:
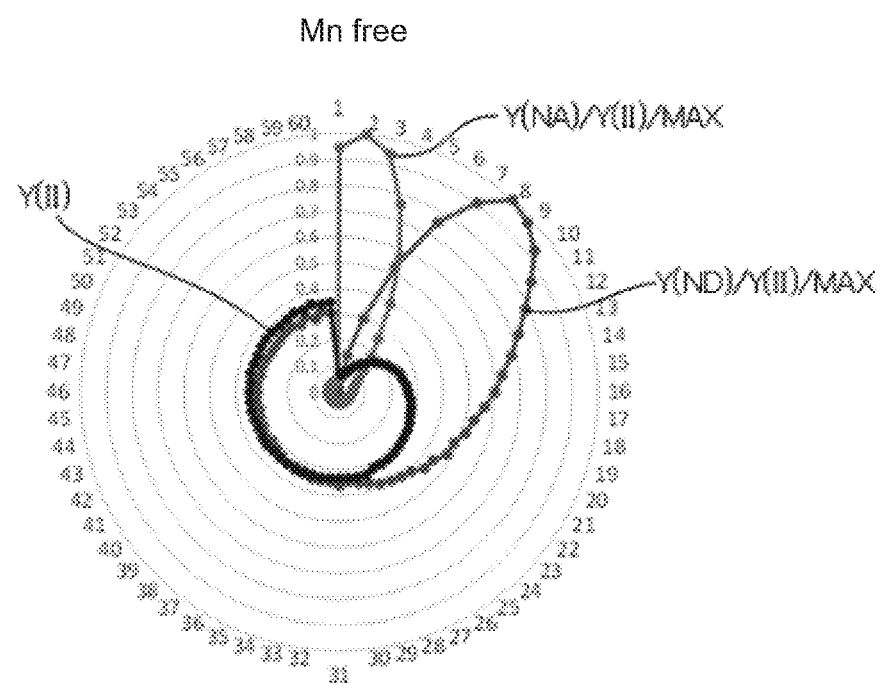
Figure 26M:
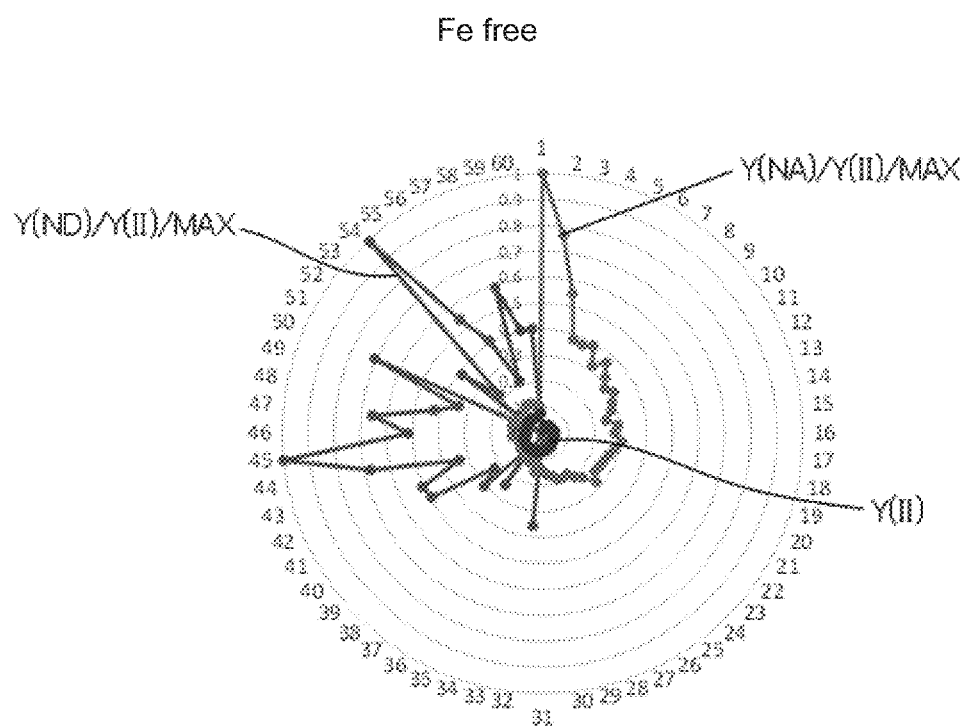
Figure 27A:
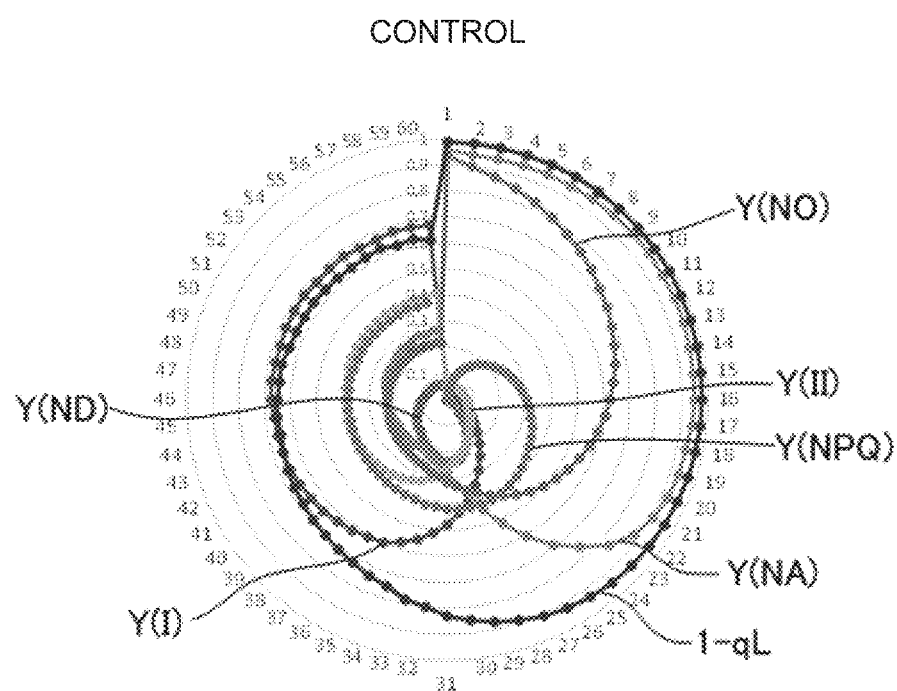
FIG. 27 shows an example of measurement result graphs in which the elapse of time is expressed circularly and Y(I), Y(ND), Y(NA), Y(II), Y(NO), Y(NPQ), and 1-qL are plotted.
Figure 27B:
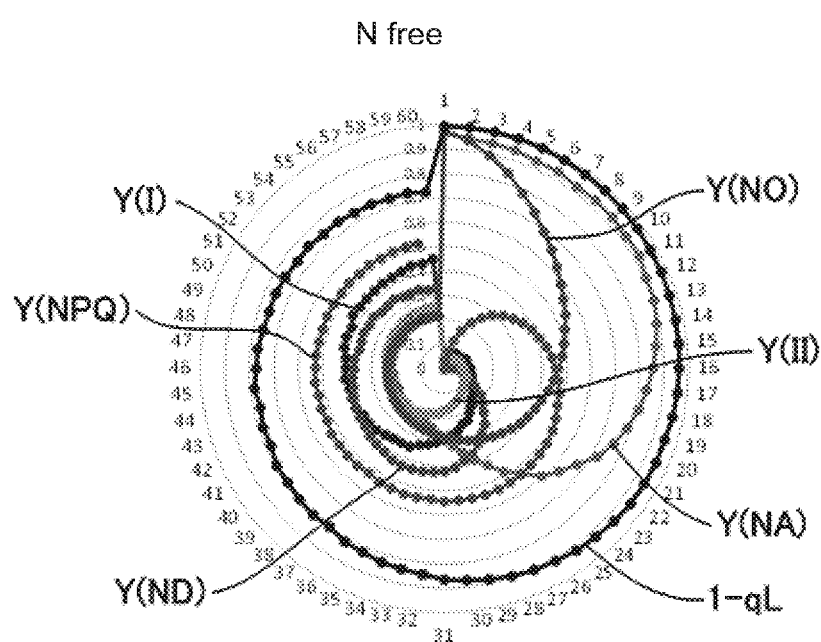
Figure 27C:
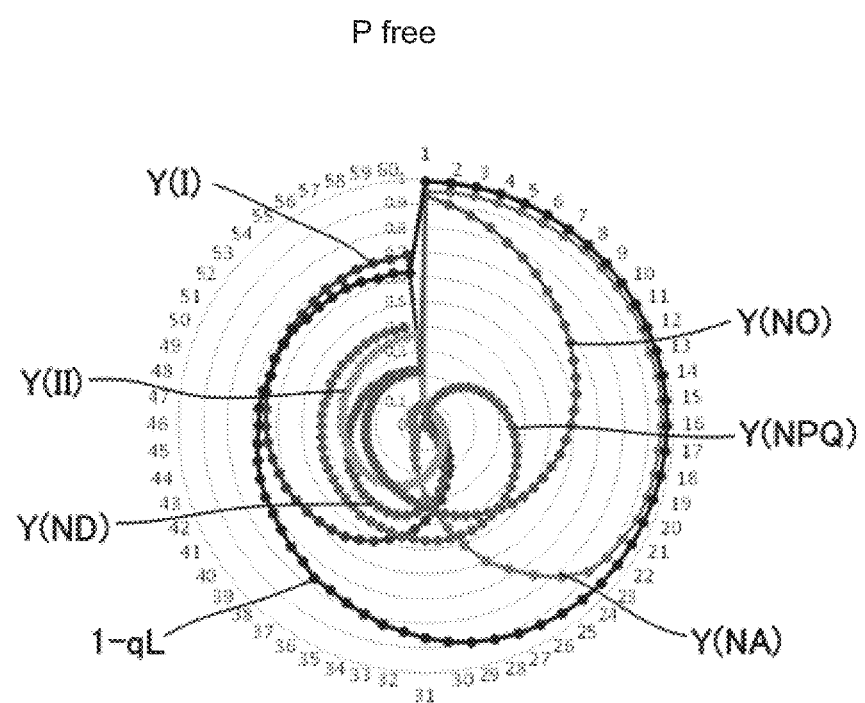
Figure 27D:
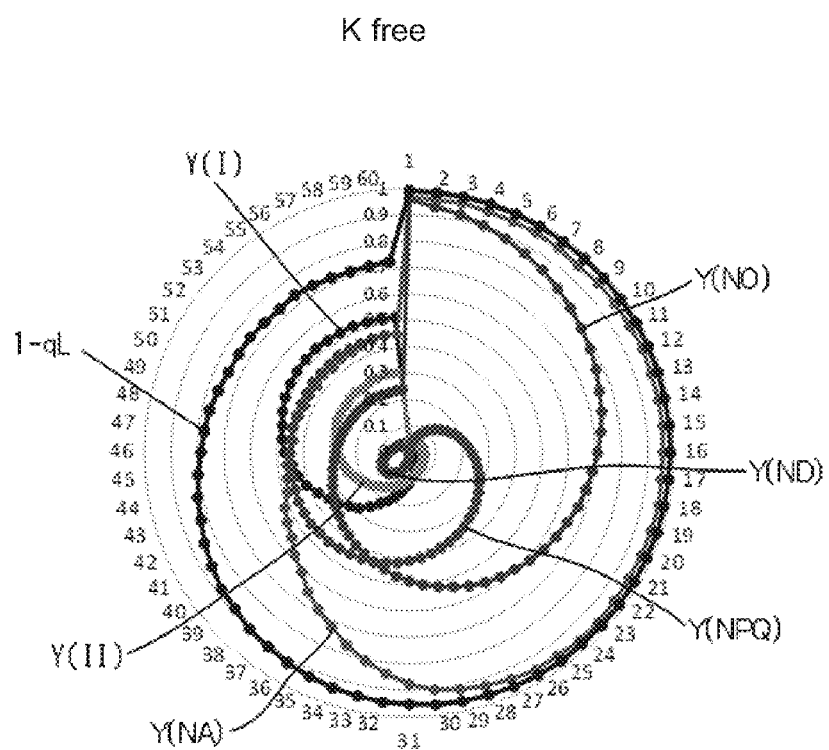
Figure 27E:
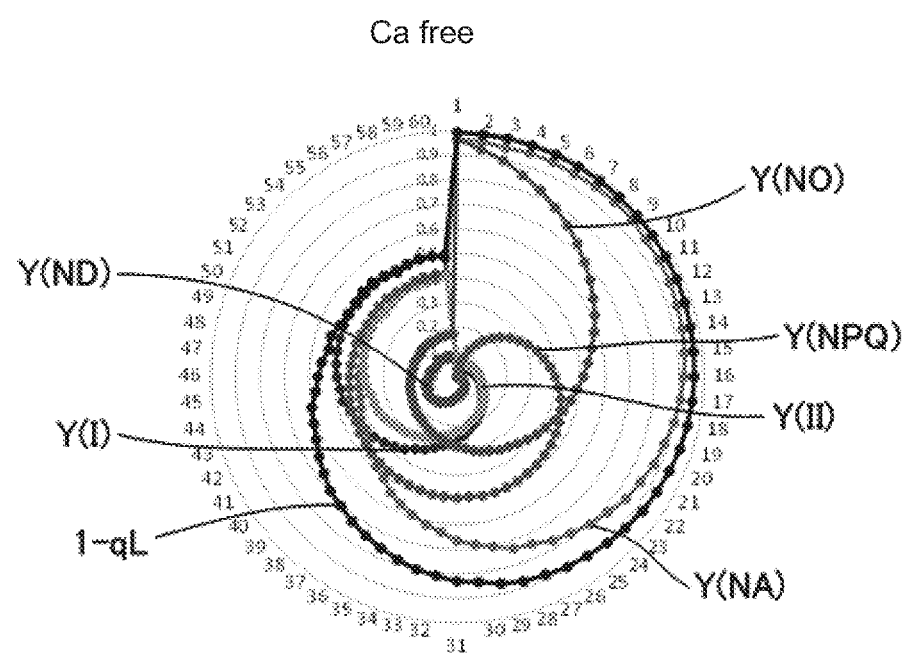
Figure 27F:
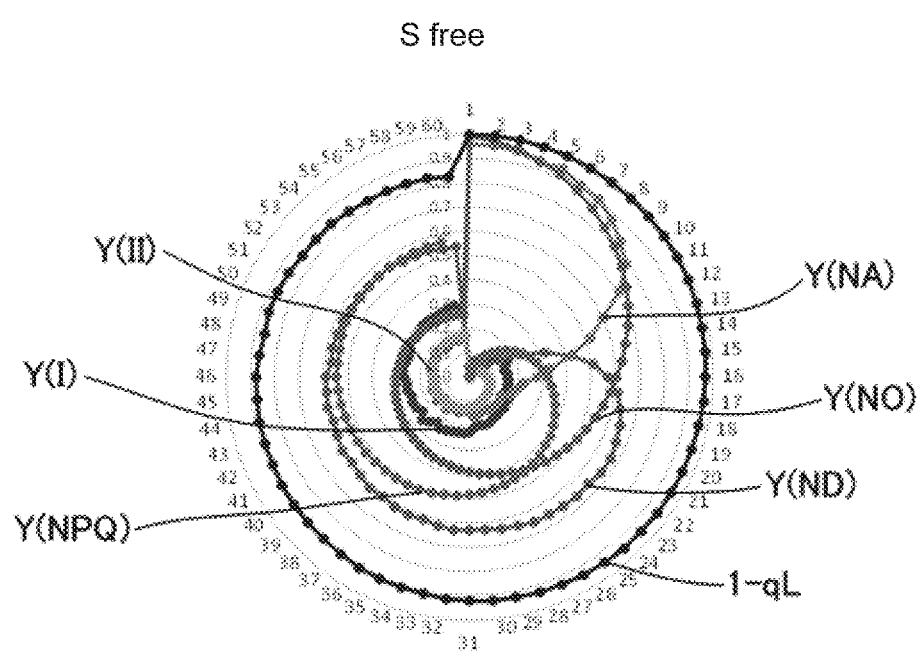
Figure 27G:
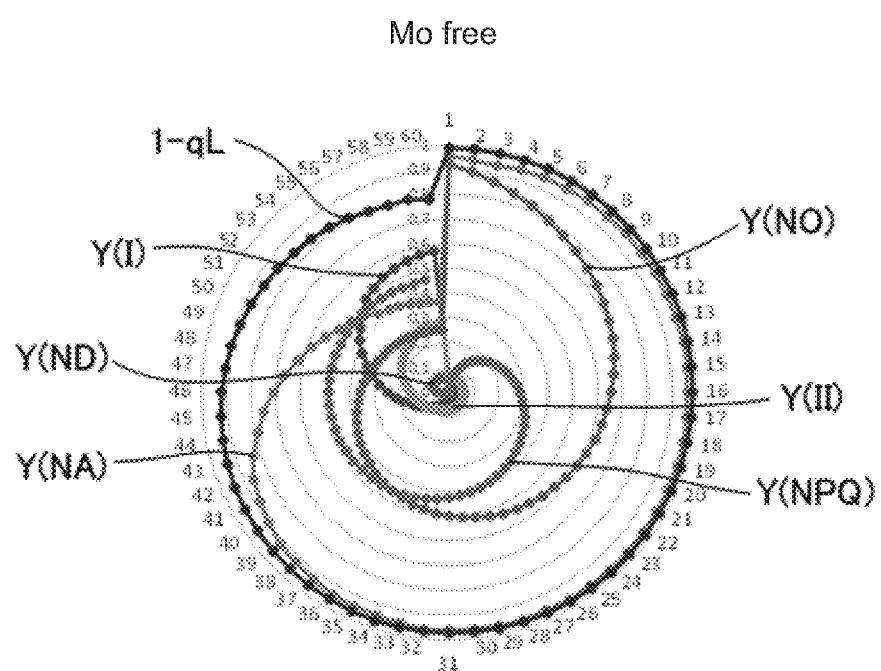
Figure 27H:
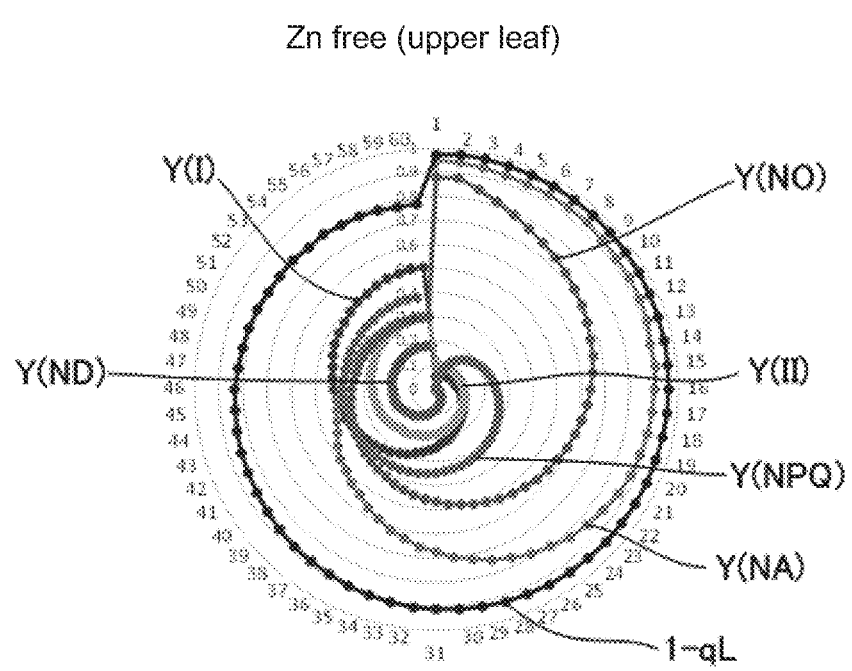
Figure 27I:
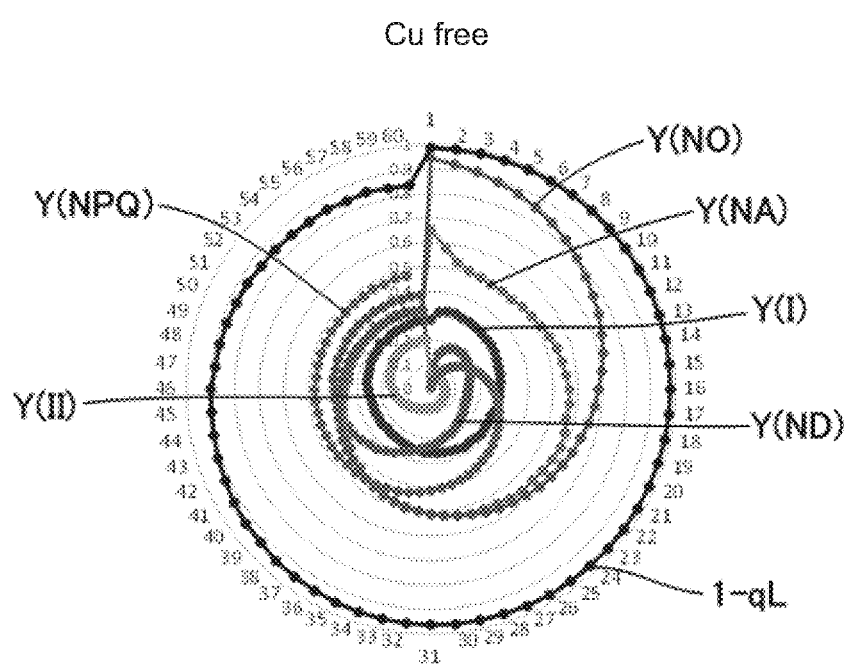
Figure 27J:
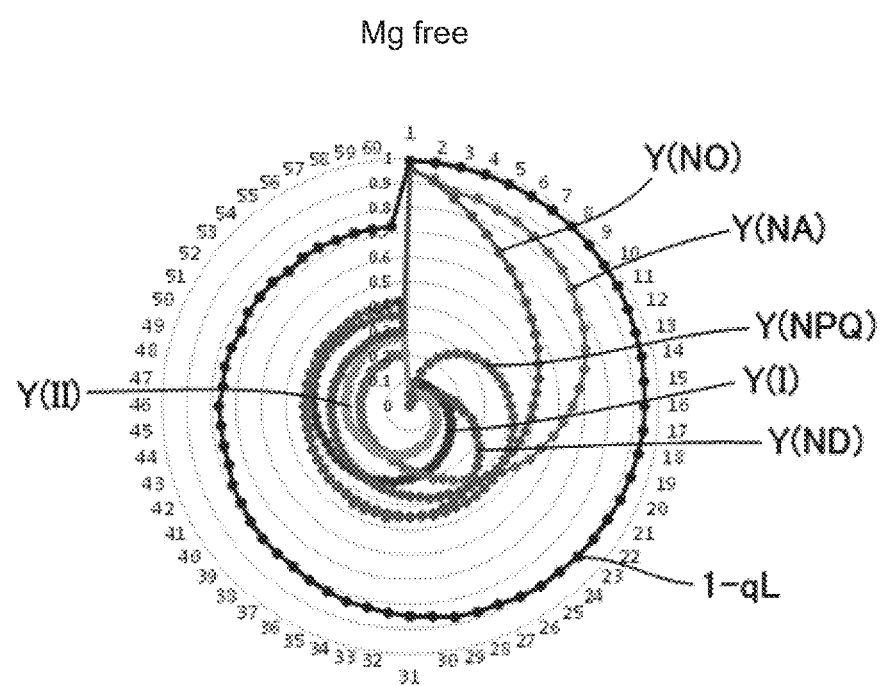
Figure 27K:
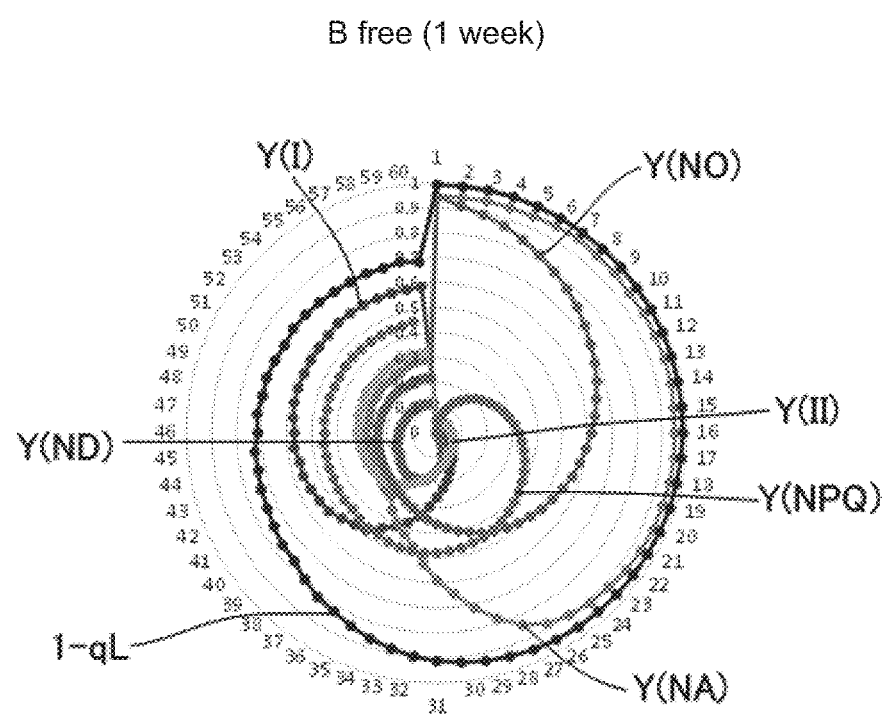
Figure 27L:
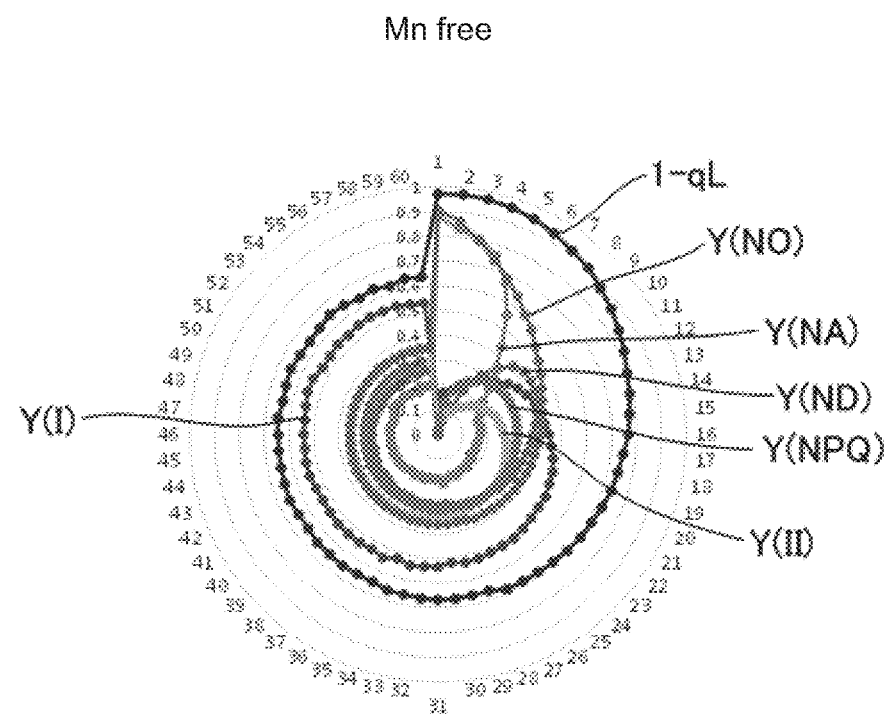
Figure 27M:
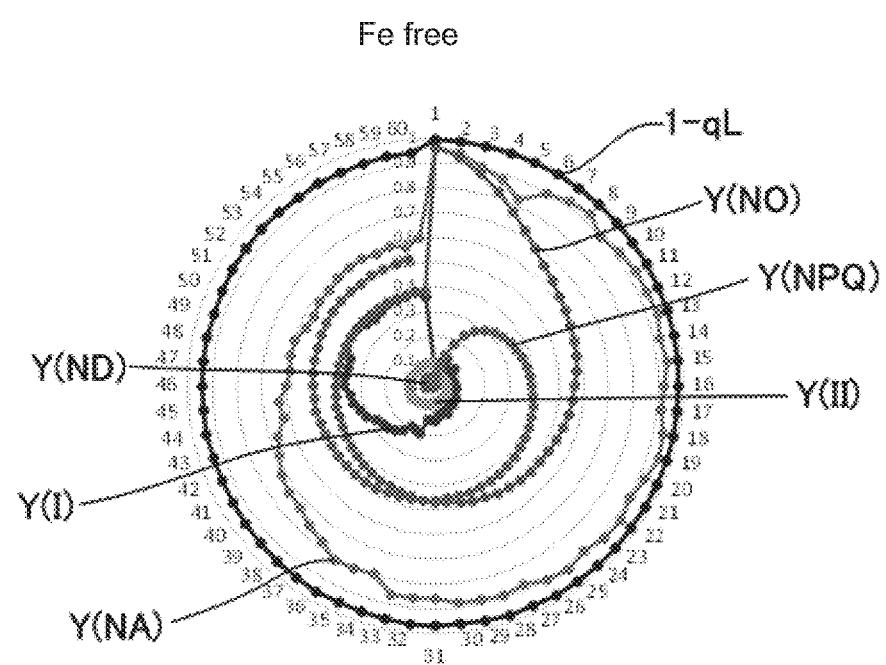
Figure 28A:
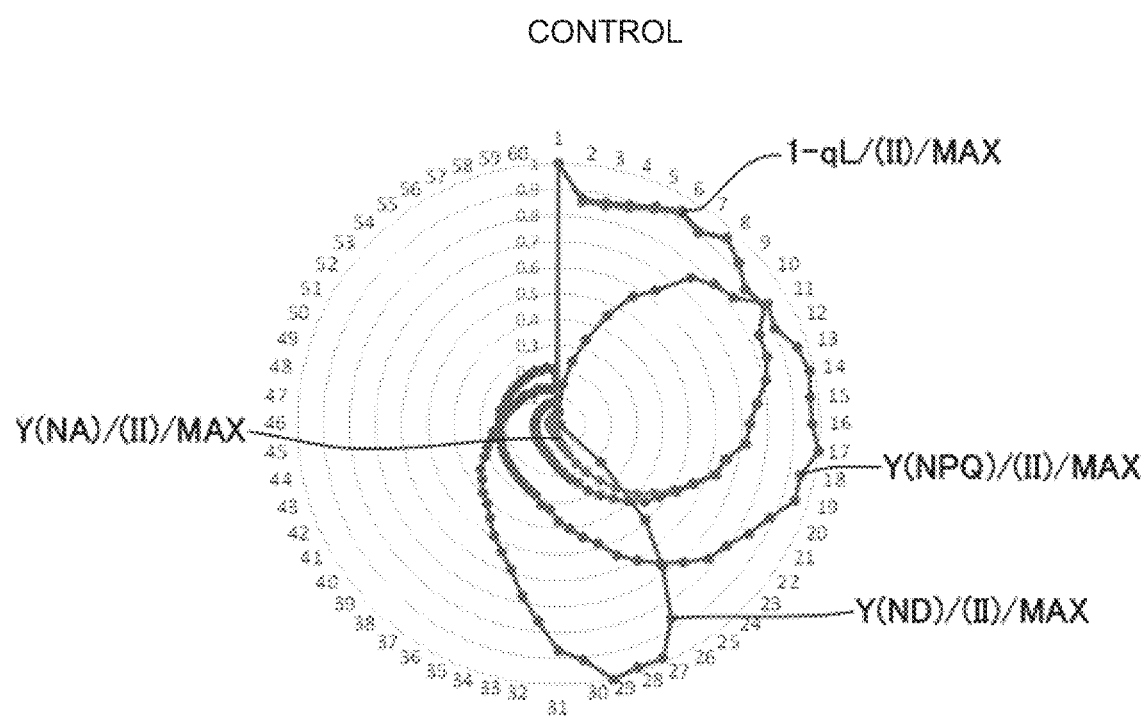
FIG. 28 shows an example of measurement result graphs showing values acquired by dividing Y(ND), Y(NA), Y(NPQ), and 1-qL by Y(II).
Figure 28B:
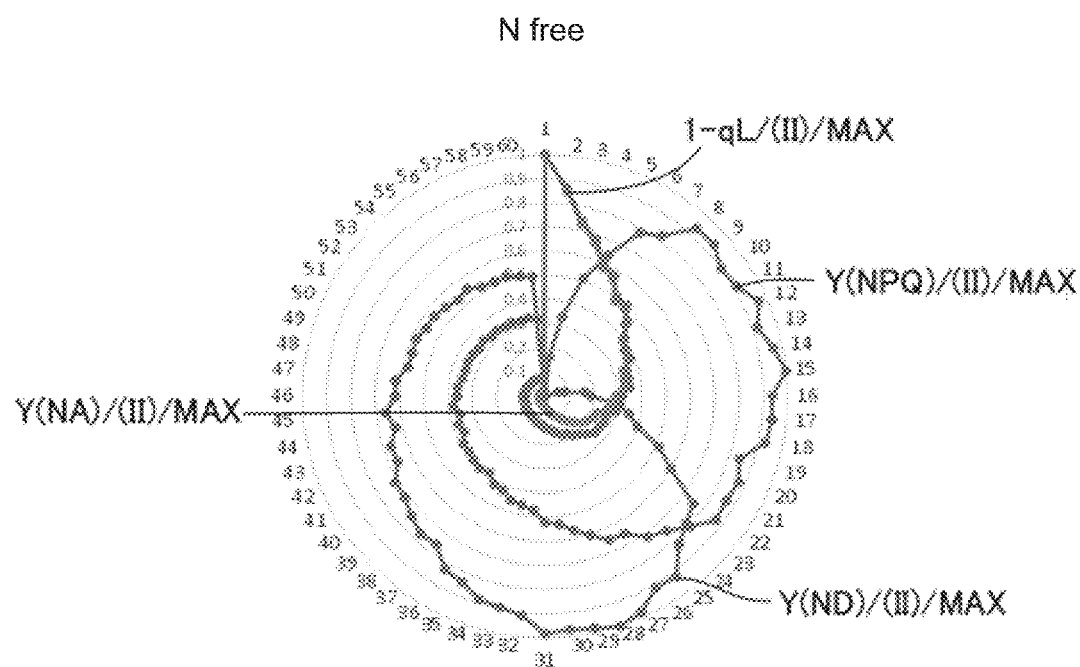
Figure 28C:
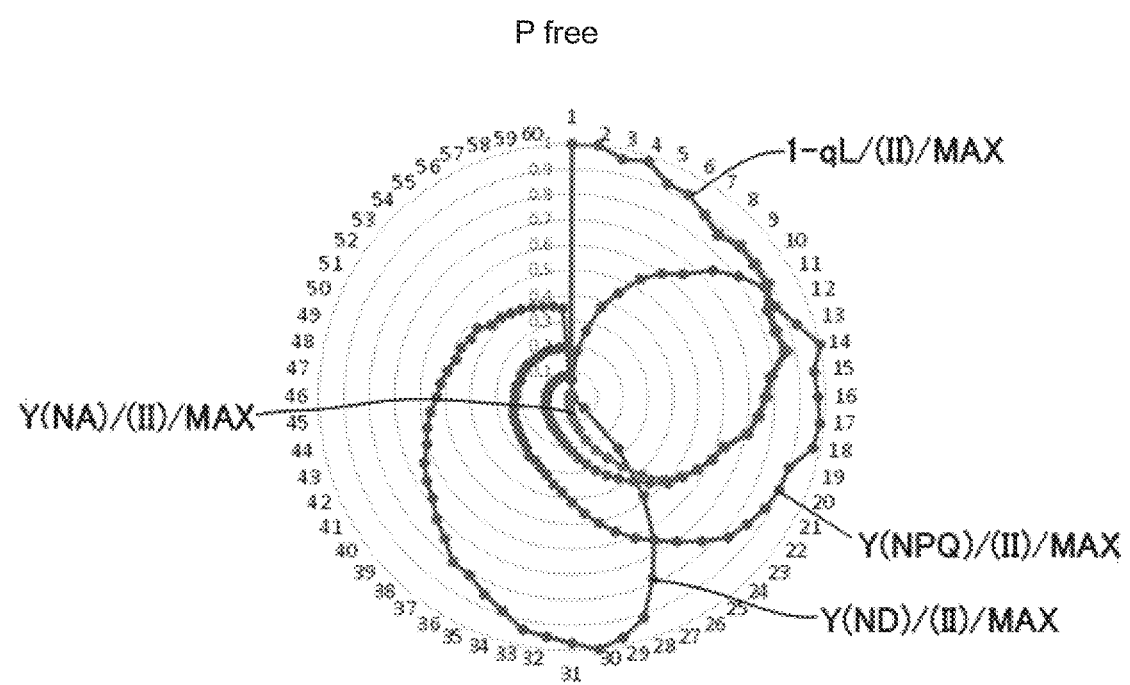
Figure 28D:
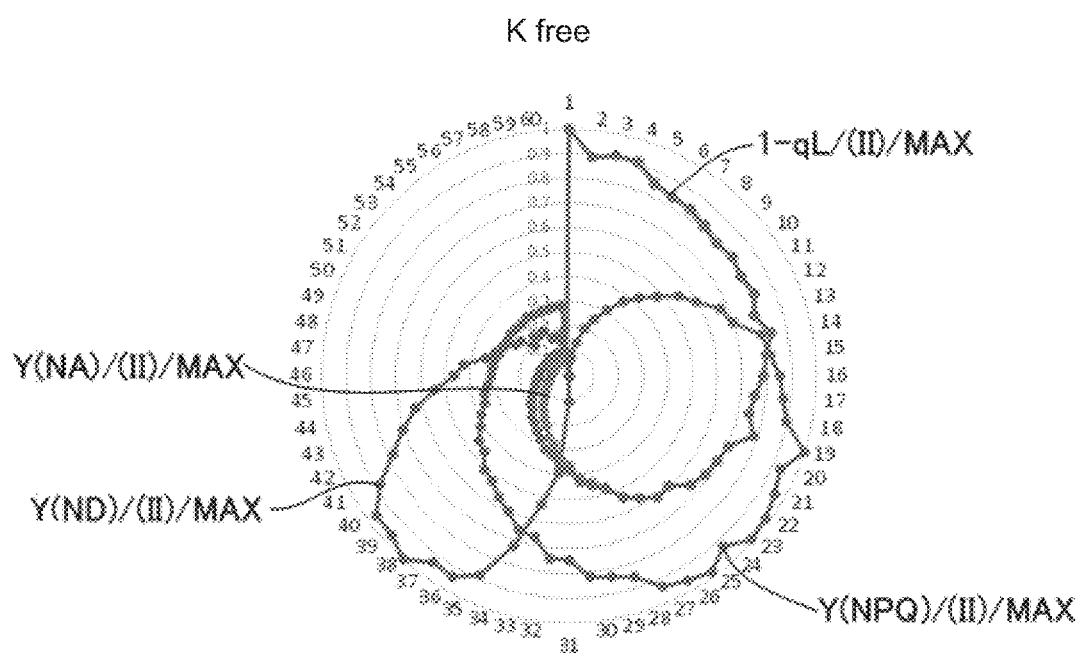
Figure 28E:
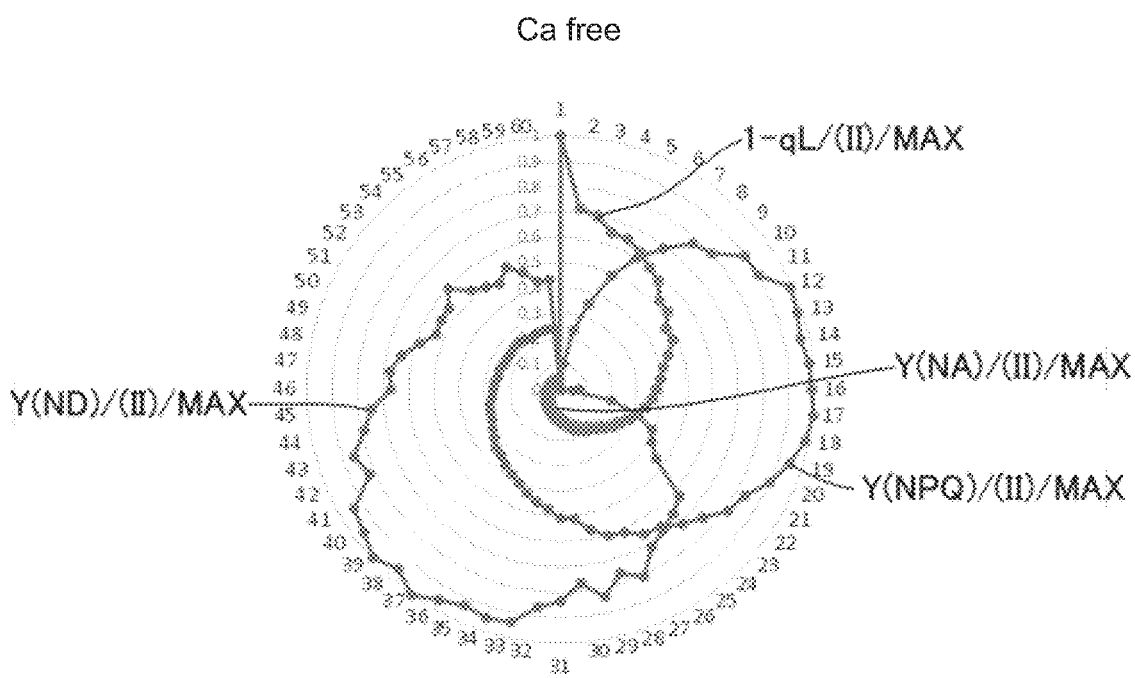
Figure 28F:
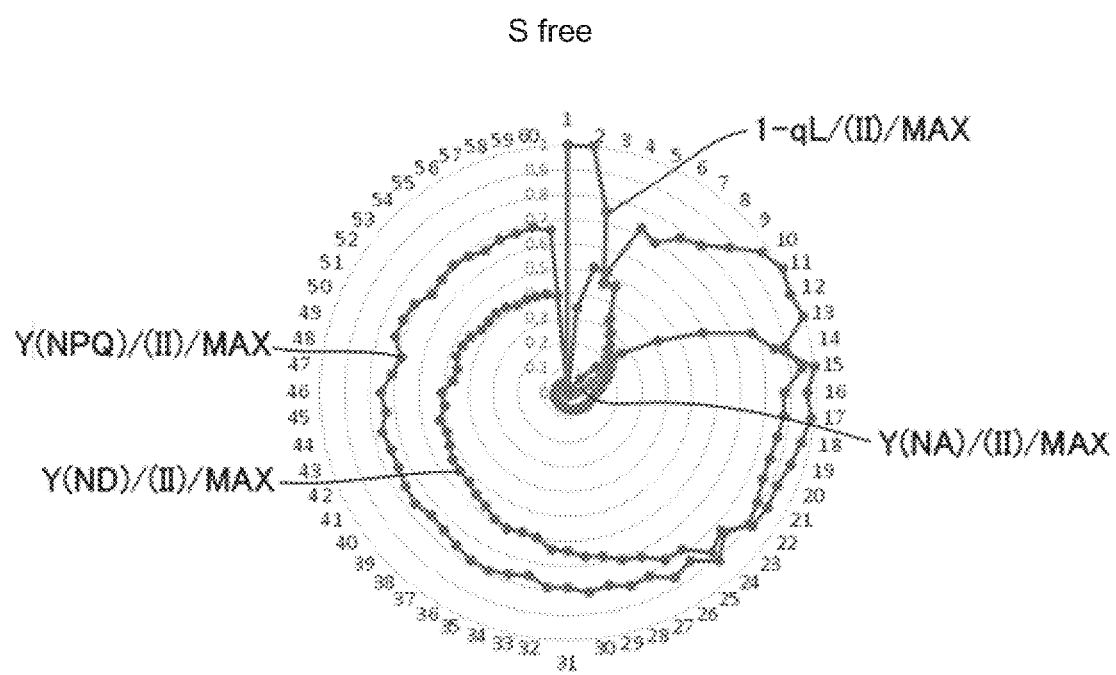
Figure 28G:
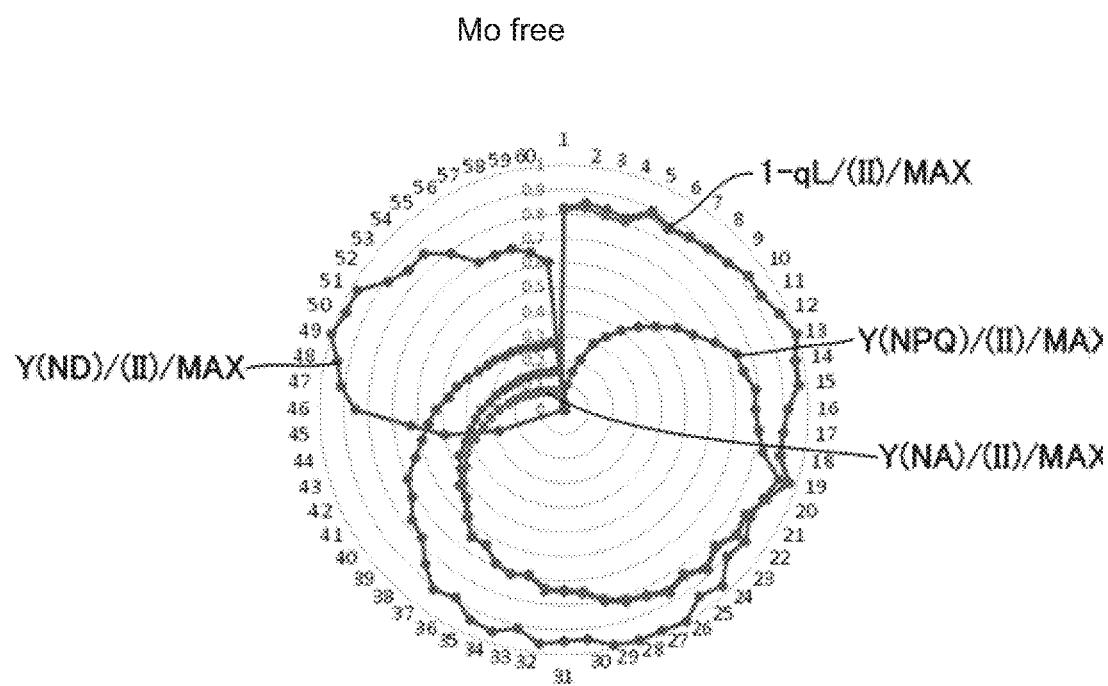
Figure 28H:
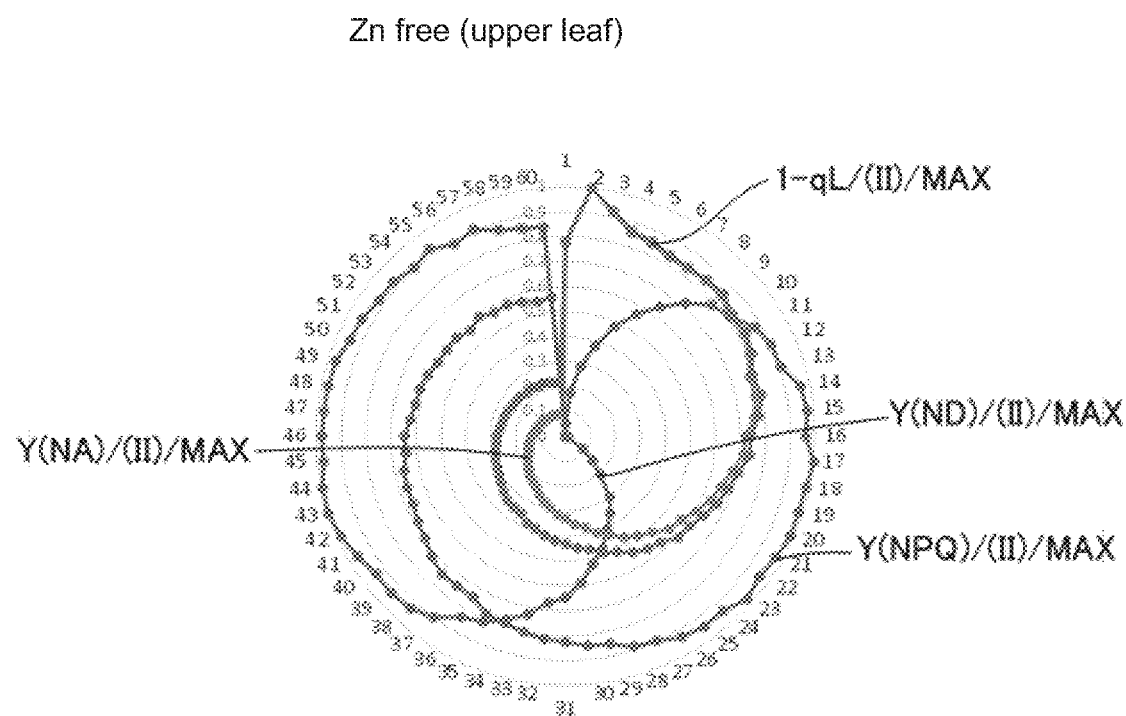
Figure 28I:
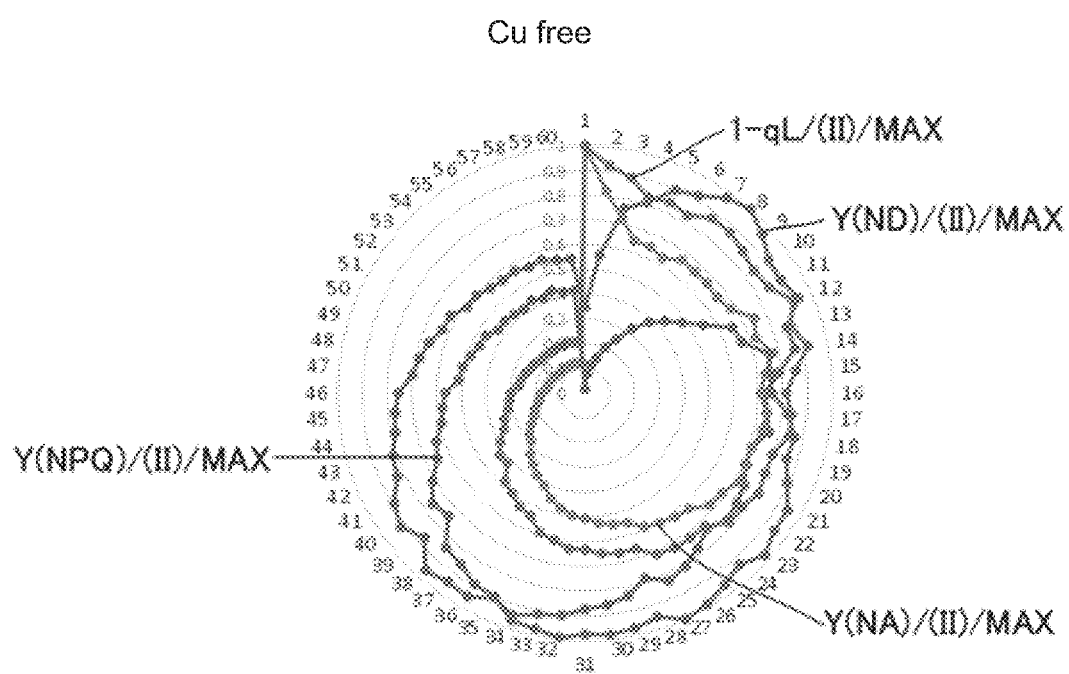
Figure 28J:
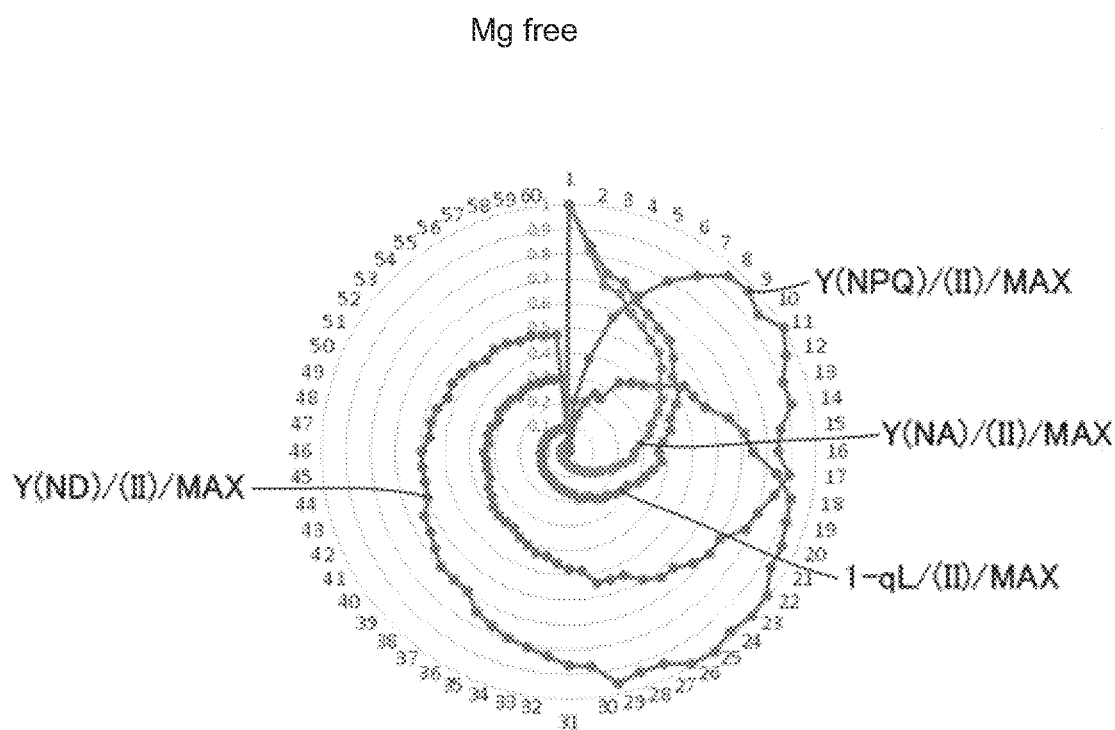
Figure 28K:
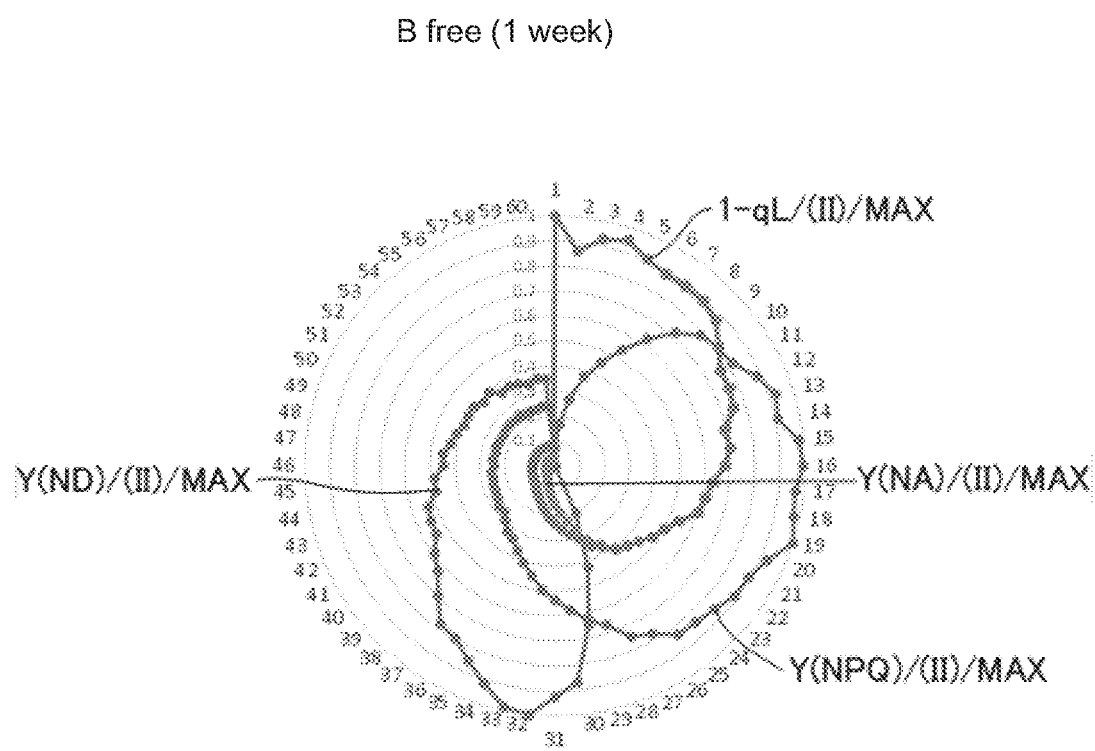
Figure 28L:
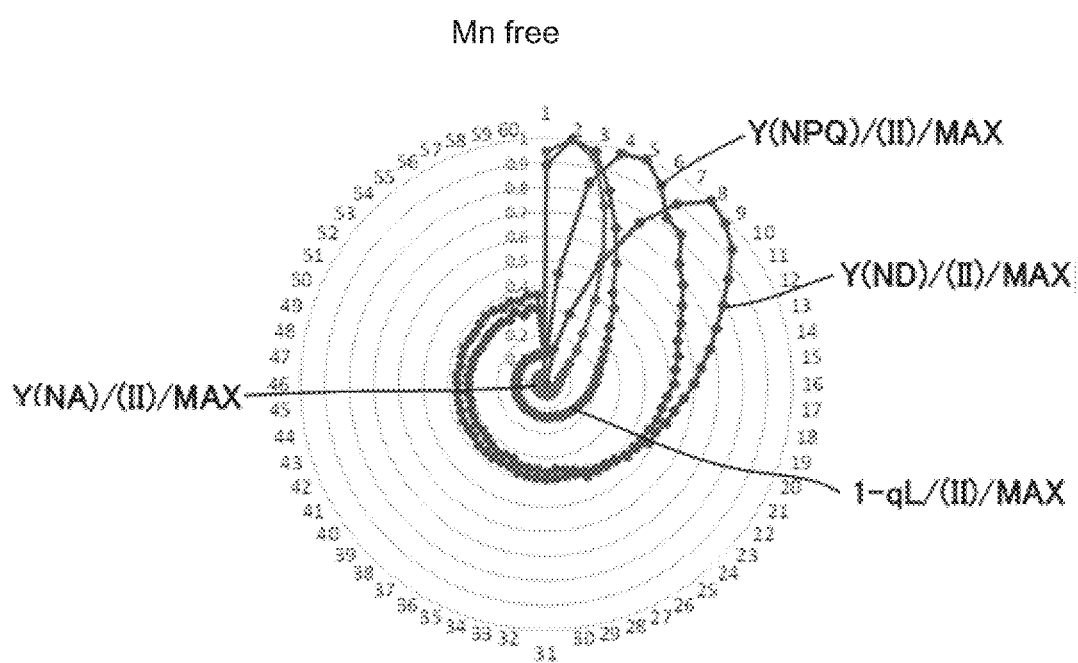
Figure 28M:
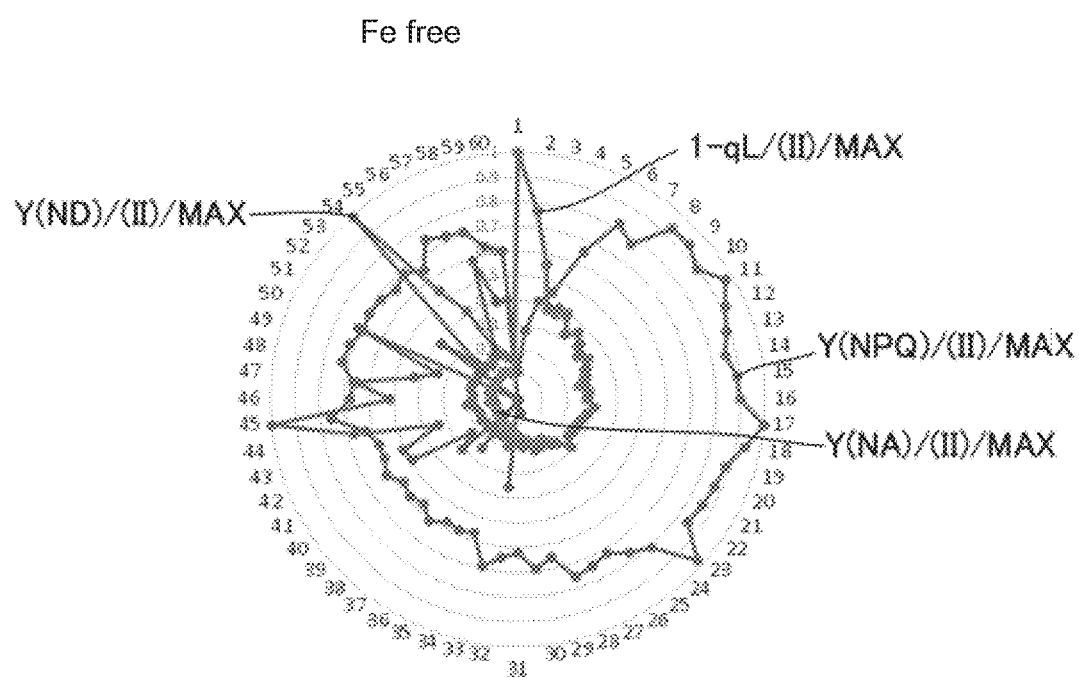
Figure 29A:
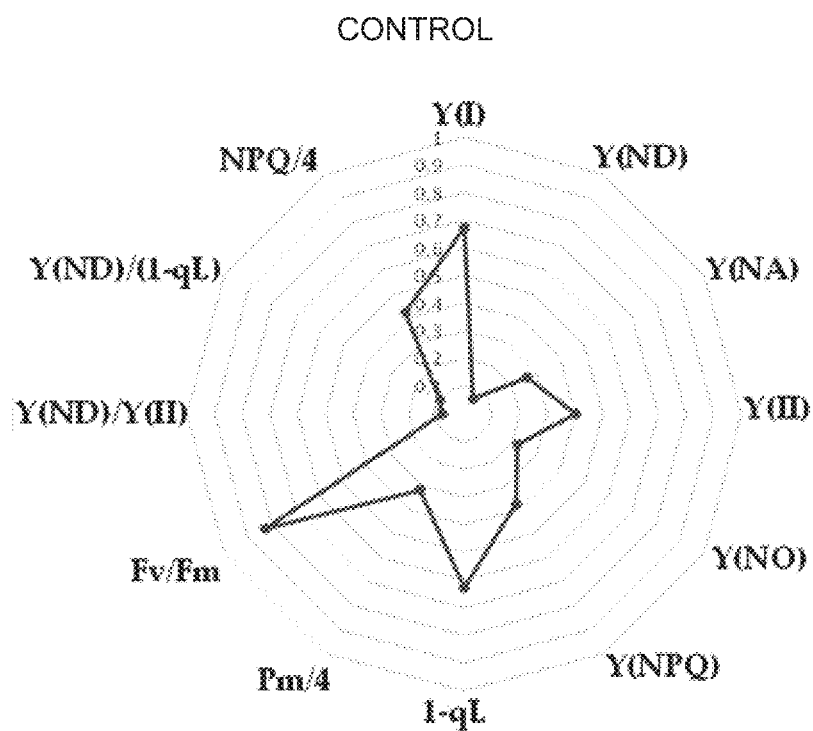
FIG. 29 shows an example of measurement result graphs in which the magnitudes of respective values of Y(I), Y(ND), Y(NA), Y(II), Y(NO), Y(NPQ), and 1-qL are expressed circularly.
Figure 29B:
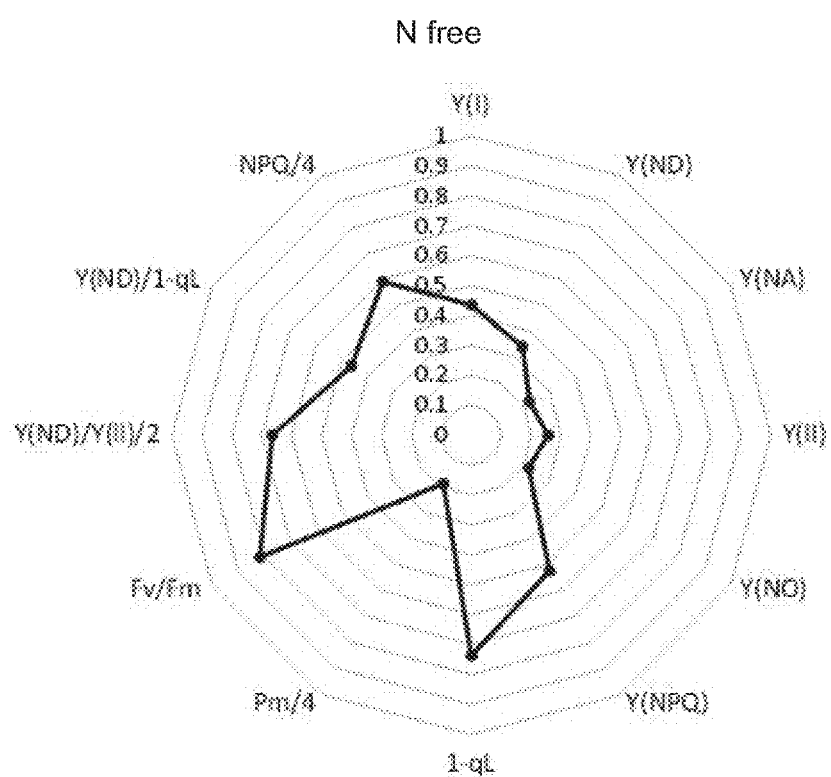
Figure 29C:
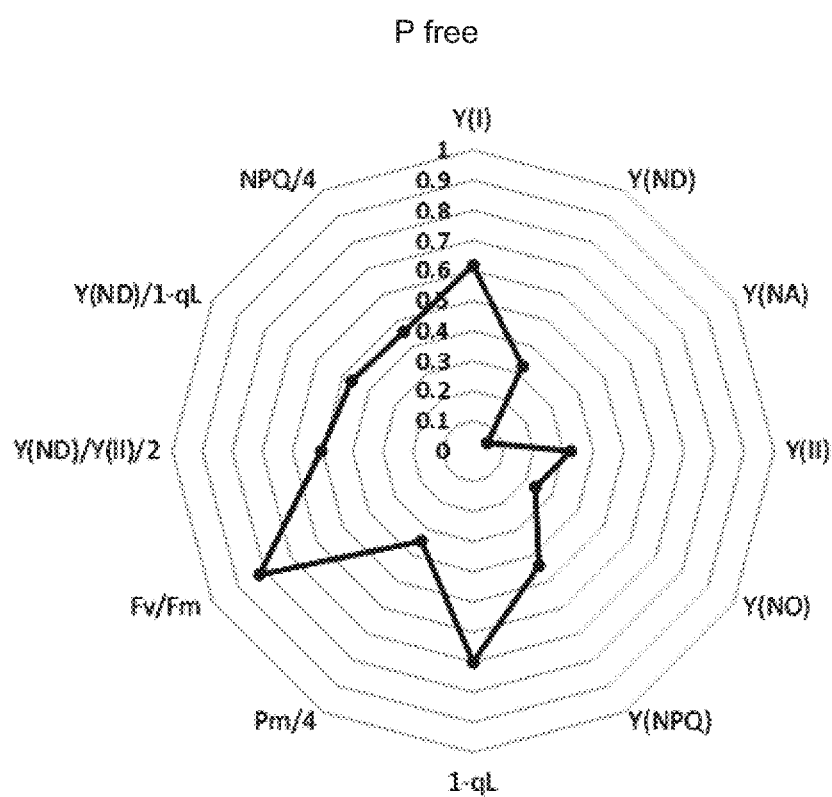
Figure 29D:
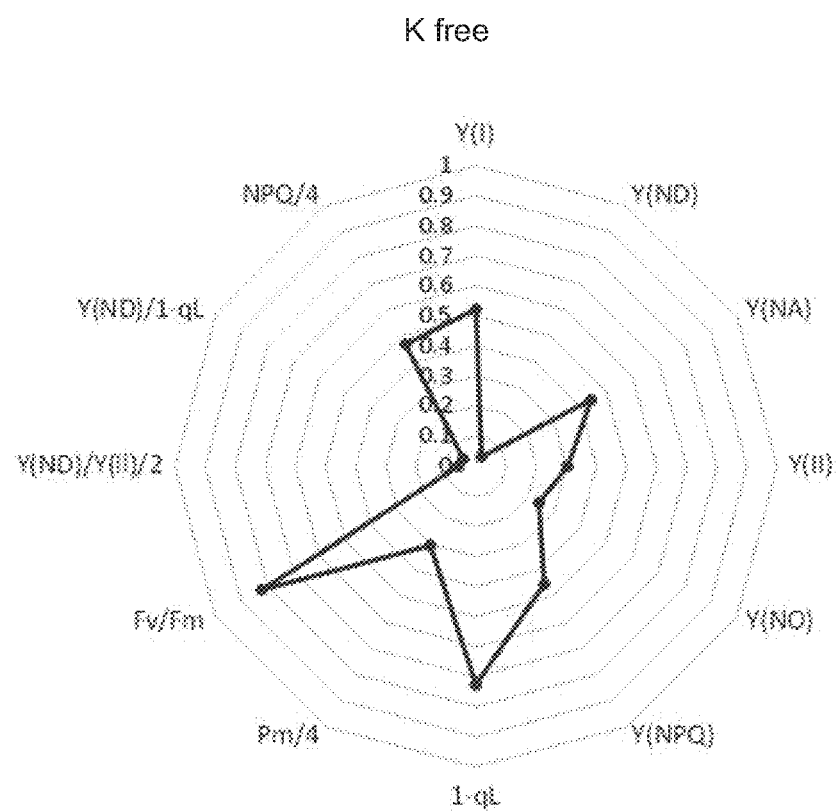
Figure 29E:
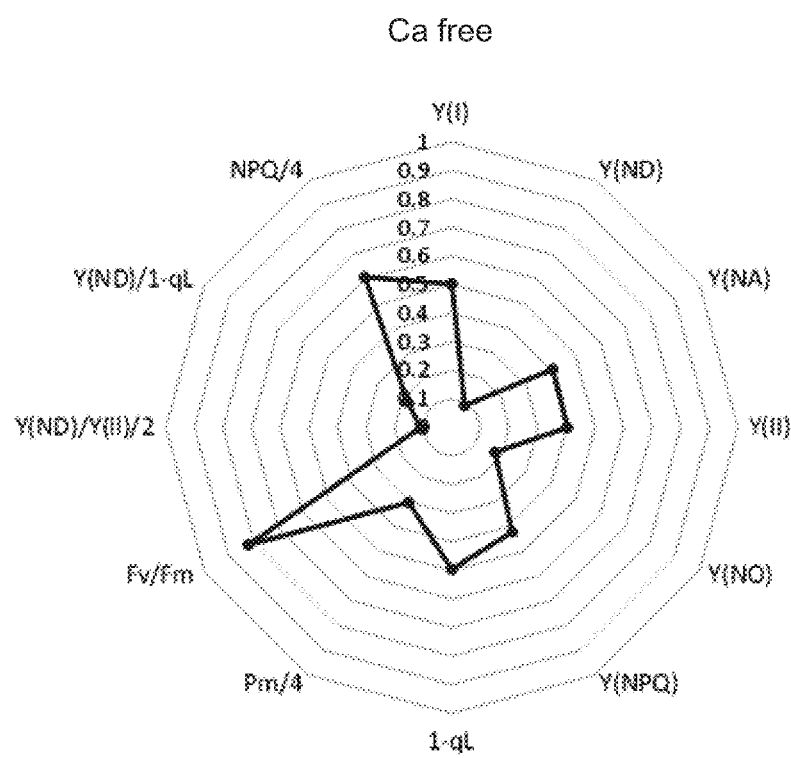
Figure 29F:
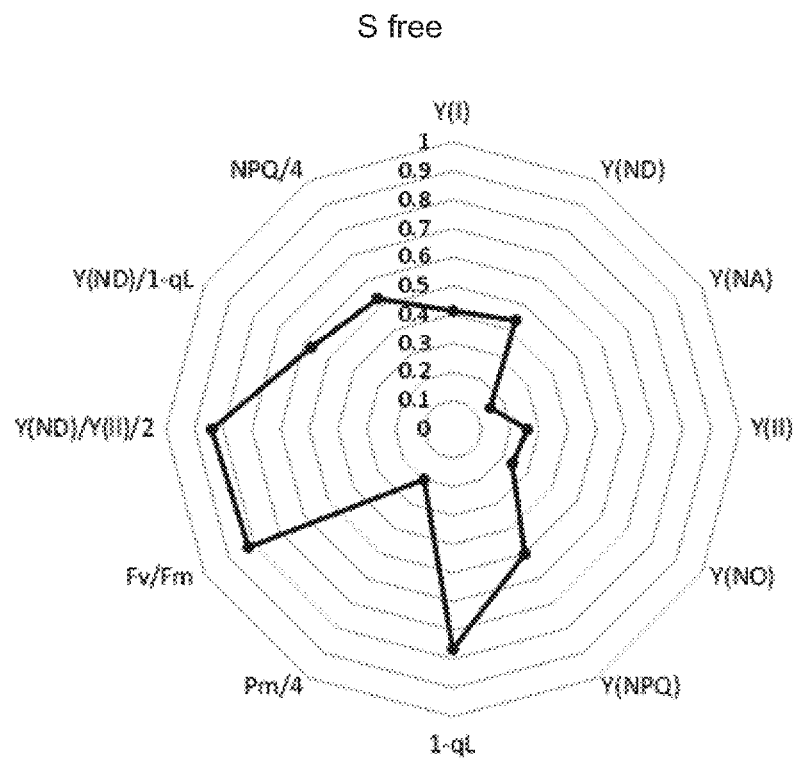
Figure 29G:
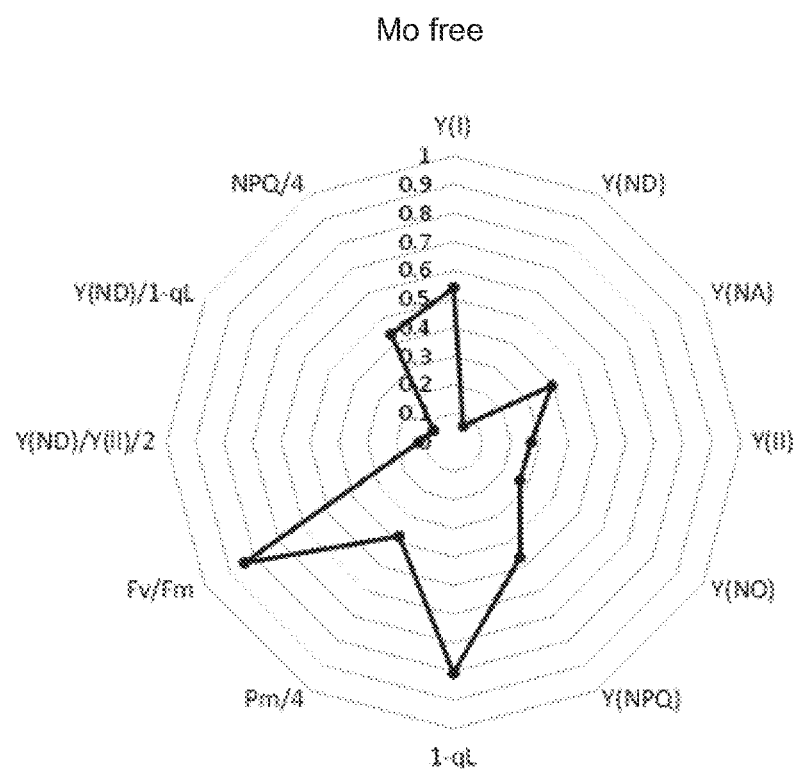
Figure 29H:
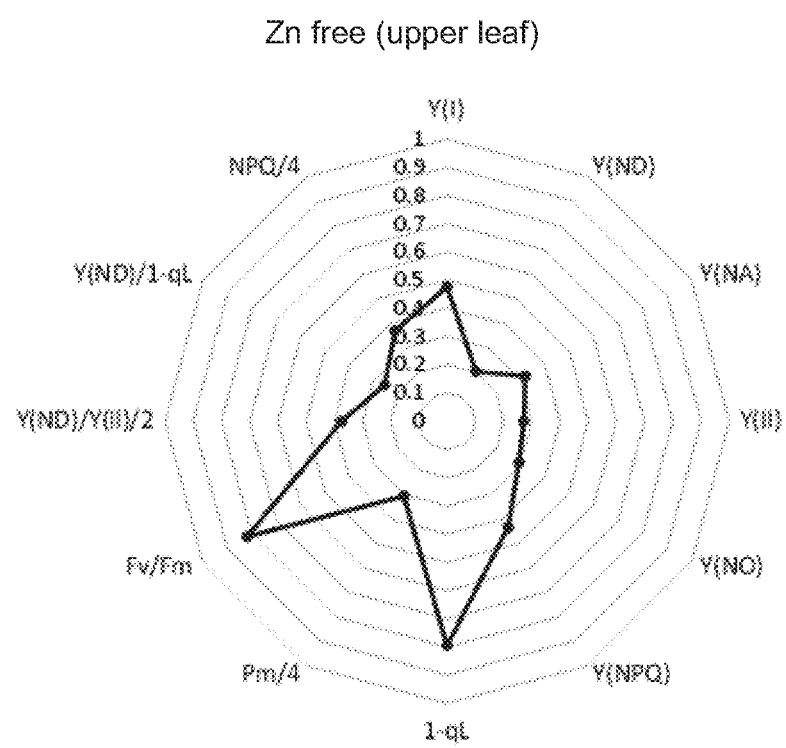
Figure 29I:
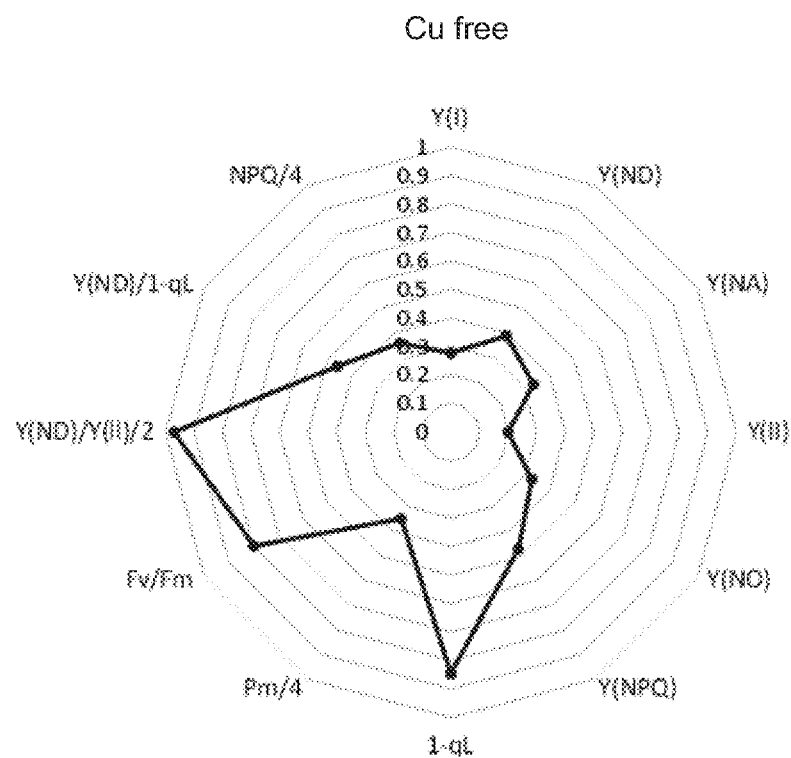
Figure 29J:
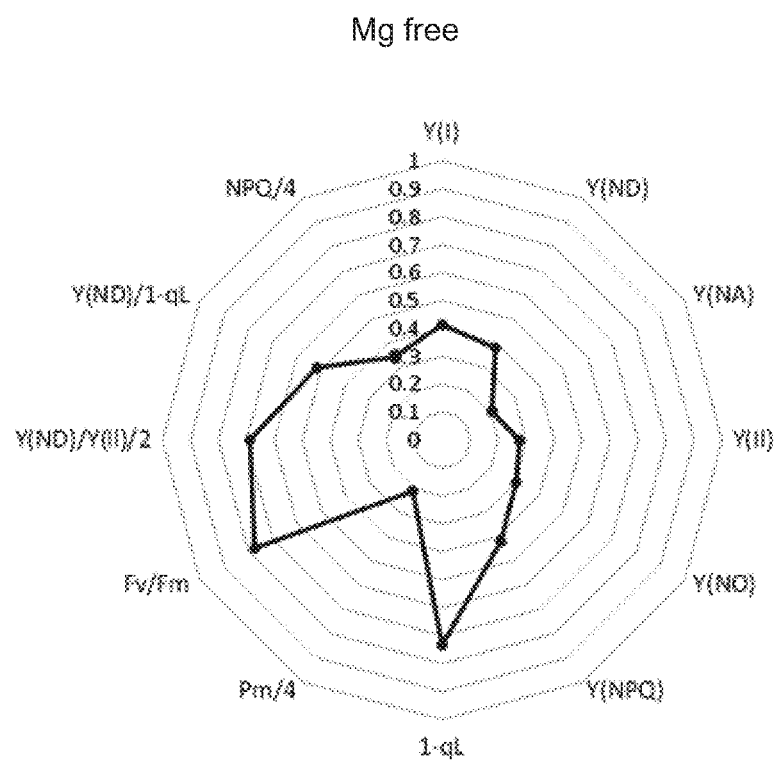
Figure 29K:
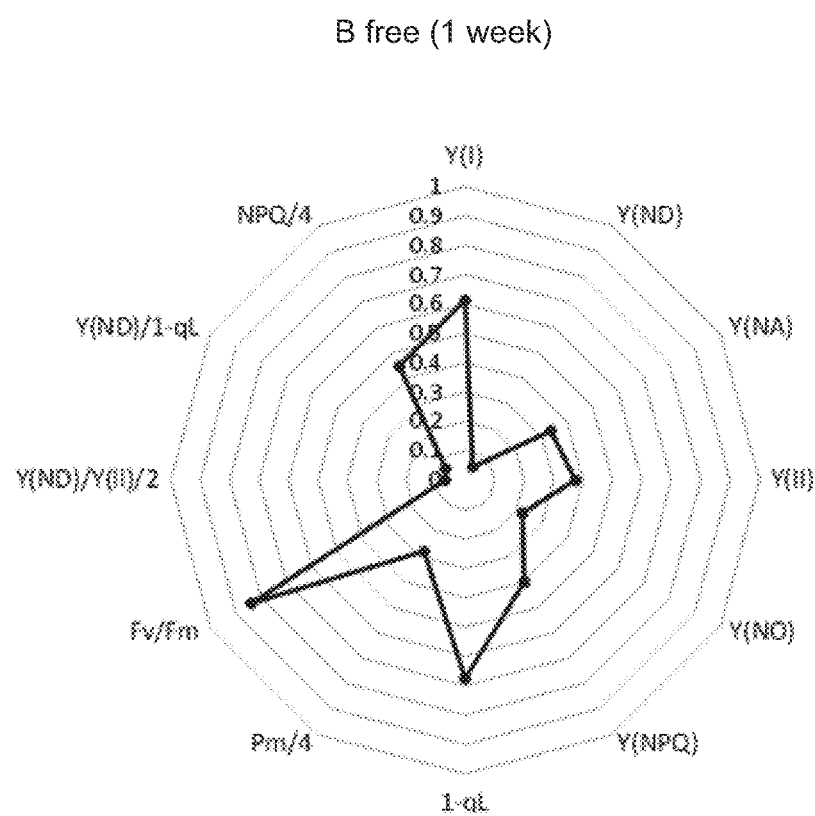
Figure 29L:
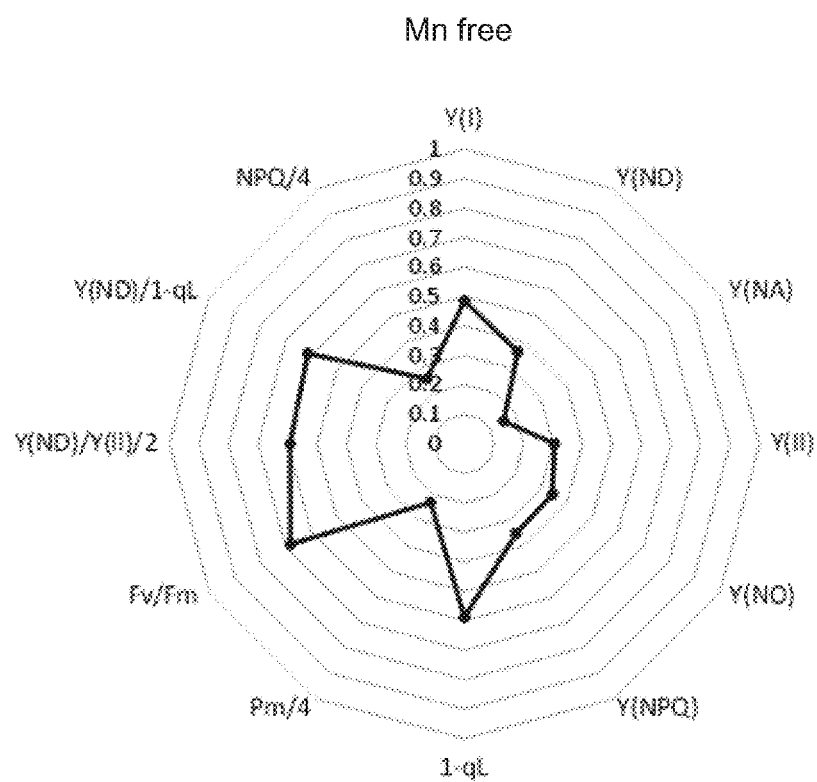
Figure 29M:
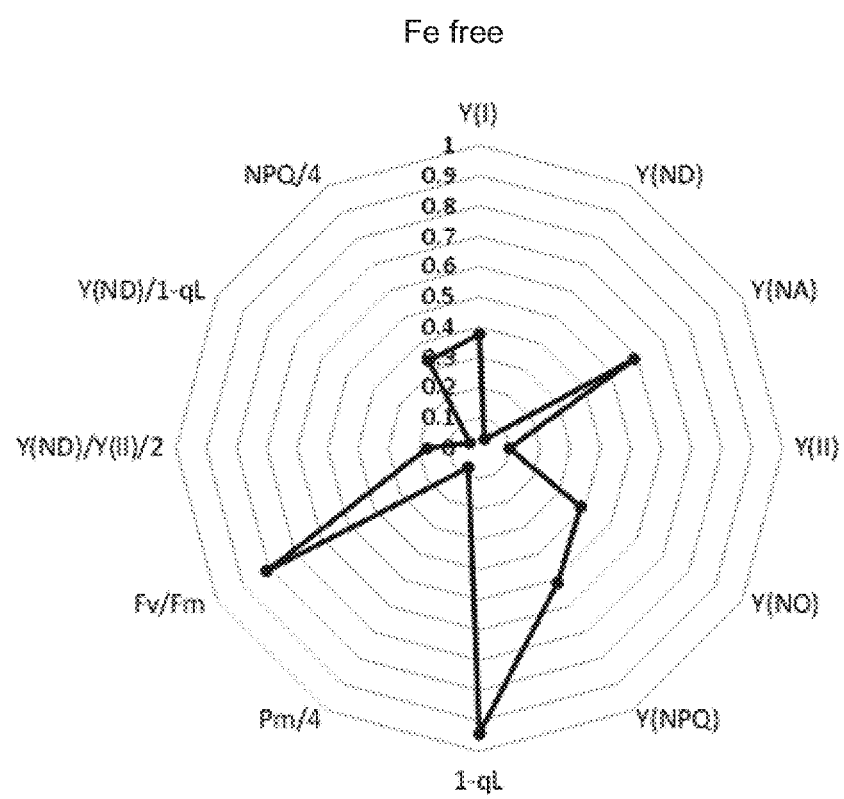

In addition, as described above, the analysis circuit 20a can calculate Y(I) which is the ground state of P700, Y(NA) which is the state in which P700 is absorbing light energy, and Y(ND) as the ROS marker by utilizing the light absorption difference (FIG. 24).

FIG. 25 shows an example of measurement result graphs (also called RFM Original Plots) in which the elapse of time is expressed circularly (in circular graphs) and Y(I), Y(ND), Y(NA), and Y(II) are plotted. In FIG. 25, a full circle of each circular graph is expressed as the elapse of time of ten minutes. In FIG. 25, even when the trajectories of plots (trajectory shapes) are compared, it cannot be said that changes in trajectory shape depending on the difference between deficient elements appear clearly.

On the other hand, FIG. 26 shows an example of measurement result graphs (also called RFM Diagnosis Plots) showing values acquired by dividing Y(I), Y(ND), and Y(NA) by Y(II) in FIG. 25. In FIG. 26, it is understood that characteristics of the trajectory shapes depending on the difference between deficient elements appear in comparison with FIG. 25 above.

In other words, according to FIG. 26, a diagnosis of mineral nutrient stress in plants (a diagnosis of a mineral nutrient deficient state) can be performed by comparing the trajectory shapes in the basic diagnosis graph acquired by a plant in which mineral nutrients are controlled and the sample diagnosis graphs acquired by the plant sample S. In addition, the trajectory shapes in the basic diagnosis graphs and the trajectory shapes in the sample diagnosis graphs can also be compared by utilizing machine learning of AI, for example, and letting a trajectory shape pattern to be automatically recognized.

Similarly, FIG. 27 shows an example of measurement result graphs (also called Diagnosis Plots) in which the elapse of time is expressed circularly and Y(I), Y(ND), Y(NA), Y(II), Y(NO), Y(NPQ), and 1-qL are plotted. In addition, FIG. 28 shows an example of measurement result graphs (also called Original Plots) showing values acquired by dividing Y(ND), Y(NA), Y(NPQ), and 1-qL by Y(II). When FIG. 27 and FIG. 28 are compared, differences in trajectory shapes in FIG. 27 are difficult to understand, whilst differences in trajectory shapes due to deficient elements in FIG. 28 can be identified relatively easily.

In addition, FIG. 29 shows an example of measurement result graphs (also called Radar charts) in which the magnitudes of respective values of Y(I), Y(ND), Y(NA), Y(II), Y(NO), Y(NPQ), and 1-qL are expressed circularly. These measurement results in FIG. 29 can also be utilized for the mineral nutrient stress diagnosis according to the present embodiment.

In other words, when studying the measurement results in FIG. 25 to FIG. 29, the analysis circuit 20a according to the present embodiment can perform the mineral nutrient stress diagnosis (mineral nutrient deficient state diagnosis) for plants by utilizing all or any of Y(II), Y(NPQ), Y(NO), 1-pL, Y(I), Y(NA), and Y(ND) which is the ROS marker.

Further, the analysis circuit 20a creates sample diagnosis graphs in which the elapse of time is expressed circularly and values acquired by dividing Y(I), Y(ND), and Y(NA) by Y(II) are plotted, and compares a basic diagnosis graph showing a plant in which mineral nutrients are controlled and the sample diagnosis graphs, so that a diagnosis of a deficient state of all or any of N, P, K, S, Mg, Ca, B, Zn, Mo, Cu, Fe, and Mn which are essential nutrients in plants can be diagnosed.

Figure 30:
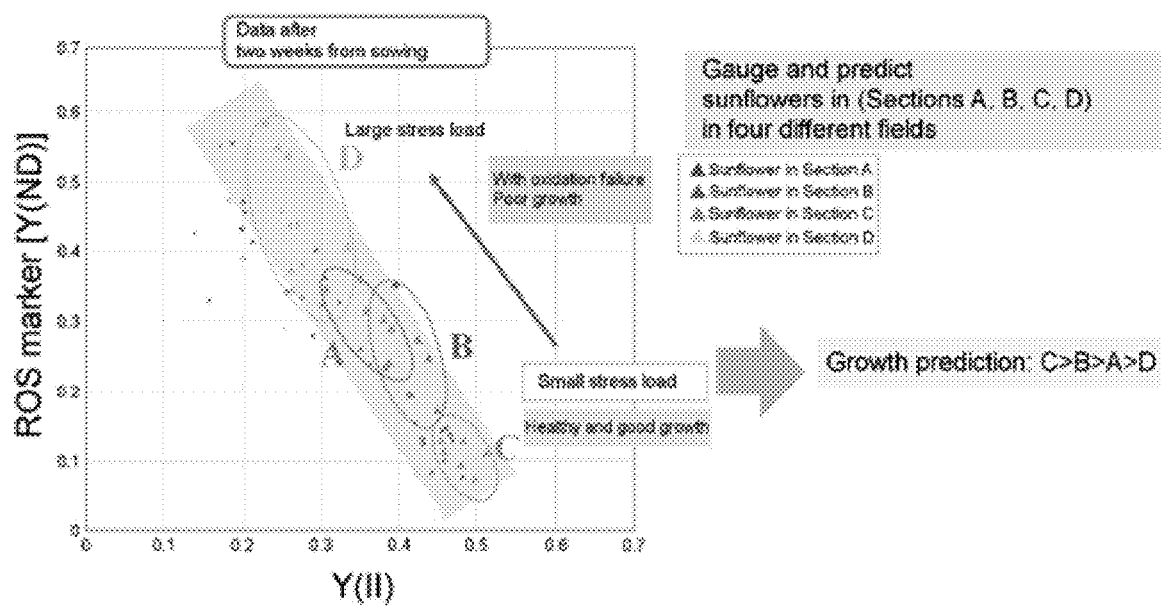
FIG. 30 shows an example of a Y(ND)-Y(II) diagnosis plot according to the present embodiment.

According to the comparison of growth of sunflowers shown in the present example, for example, it is understood that plot positions showing the correlation between the ROS marker and Y(II) are different among fields A to D as shown in FIG. 30. The differences in plot positions can be differentiated (classified) respectively into the region A, the region B, the region C, and the region D in the correlation diagram in FIG. 30. In the present embodiment, the growth of plants can also be predicted by analyzing the regions of the plot positions.

Specifically, the field C (the region C) is a field which is healthy and in which sunflower grows well (a region in which the ROS marker occurs less) as shown in FIG. 30, and growth of plants based on the results in the present example is predicted as C>B>A>D (growth is poor in a region in which the photosynthetic activity decreases and the production of the ROS marker tends to increase).

Figure 31:
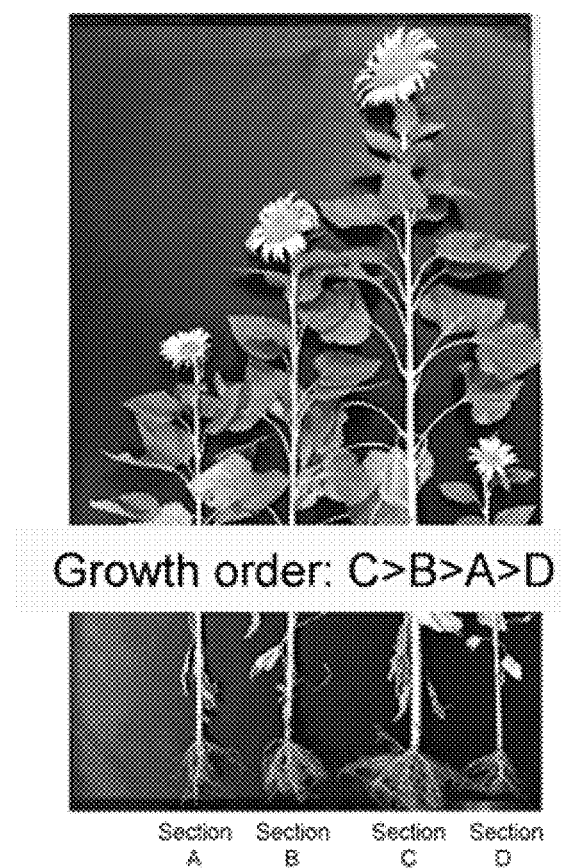
FIG. 31 shows a schematic image of how sunflowers have grown after two months from sowing.

Then, FIG. 31 shows a schematic image of how sunflowers have grown after two months from sowing. As shown in FIG. 31, the order of growth was C>B>A>D similarly to the prediction of growth in FIG. 30. In this manner, by utilizing the environmental stress diagnosis device according to the present embodiment, the degree of growth of plants can be predicted from the correlation between the ROS marker and the photosynthetic activity (Y(II) and V(O$_2$)).

Further, a deficient state of essential nutrients in plants can also be predicted or diagnosed in more detail from plot shapes in sample diagnosis graphs (FIG. 26 and FIG. 28, for example) in which the elapse of time is expressed circularly and values acquired by dividing Y(I), Y(ND), and Y(NA) by Y(II) are plotted as described above.

Figure 32:
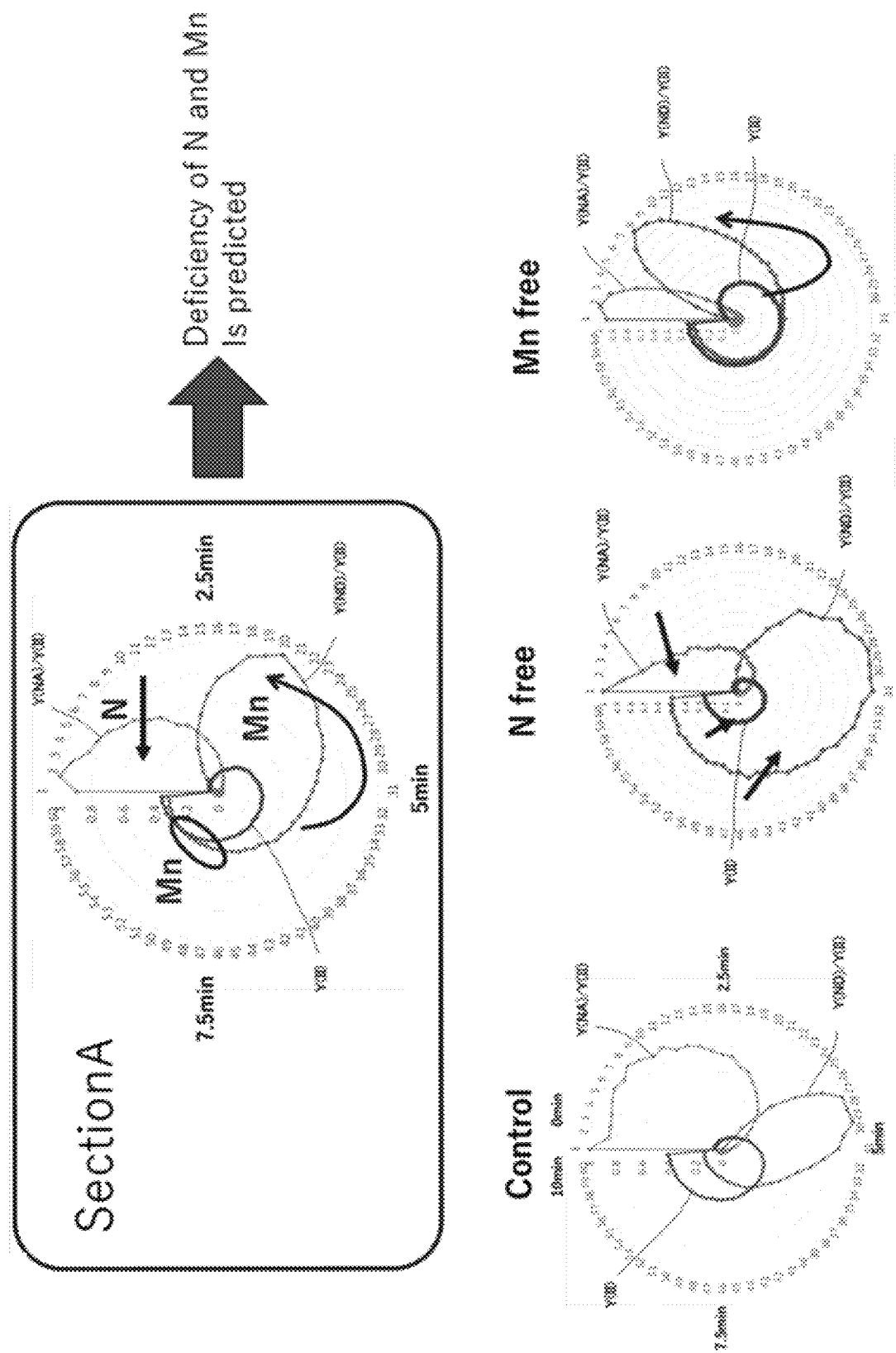
FIG. 32 shows a schematic diagram of a diagnosis image by means of a sample diagnosis graph in the present embodiment.

Specifically, as shown in FIG. 32, a difference in shape is clearly seen between a plot shape in a controlled plant and a plot shape in a state deficient in N or Mn, for example. In this manner, the deficient state of essential nutrients in plants can also be diagnosed early by analyzing the plot shape of a sample diagnosis graph by utilizing the environmental stress diagnosis device according to the present embodiment.

Figure 33:
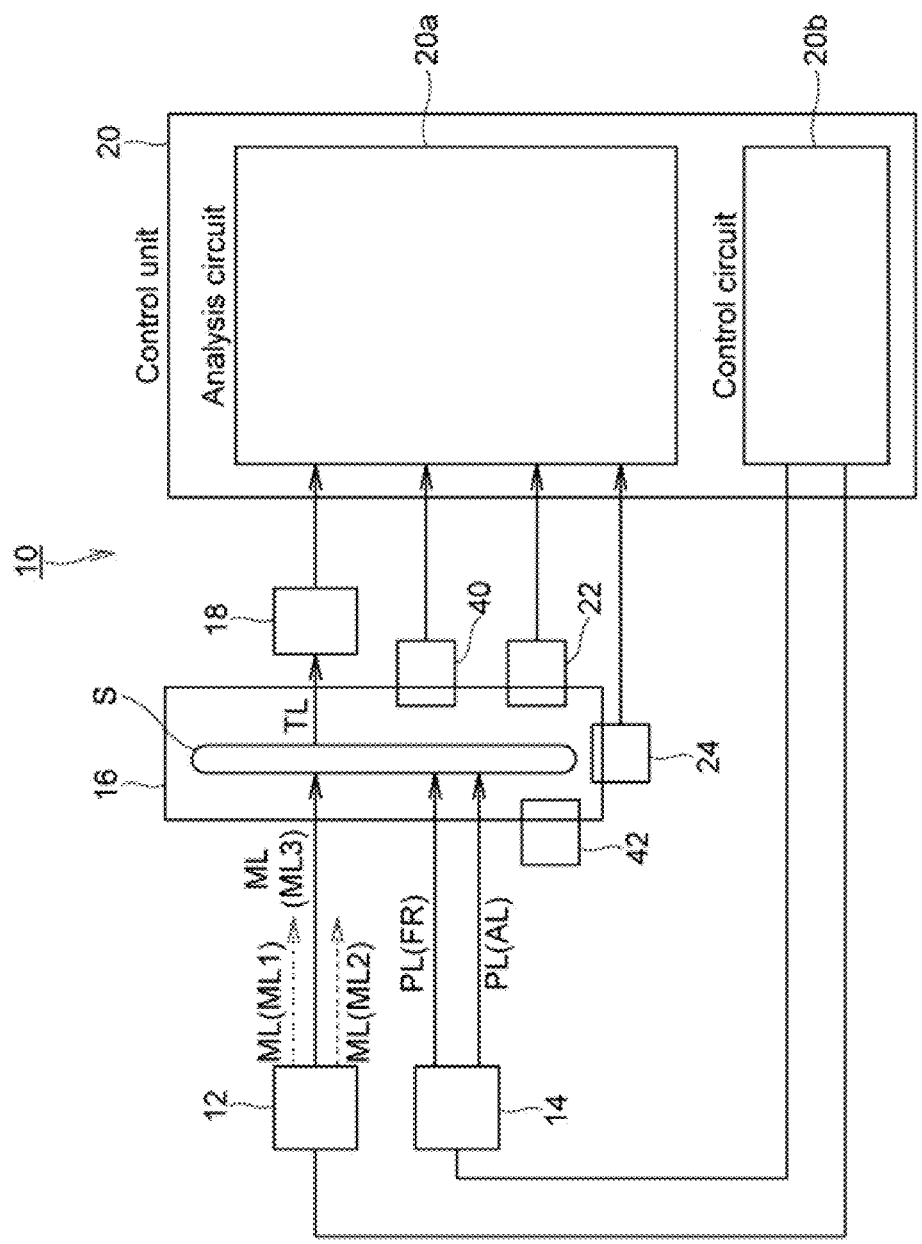
FIG. 33 shows a schematic configuration diagram in which a temperature adjustment unit is added to the environmental stress diagnosis device according to the present embodiment.

In addition, in the environmental stress diagnosis device according to the present embodiment, the sealed chamber 16 can also be equipped with a temperature adjustment unit 42 as shown in FIG. 33. In the present embodiment, a leaf temperature inside (the temperature of the plant sample S) can be controlled by providing the sealed chamber 16 with this temperature adjustment unit 42.

Figure 34:
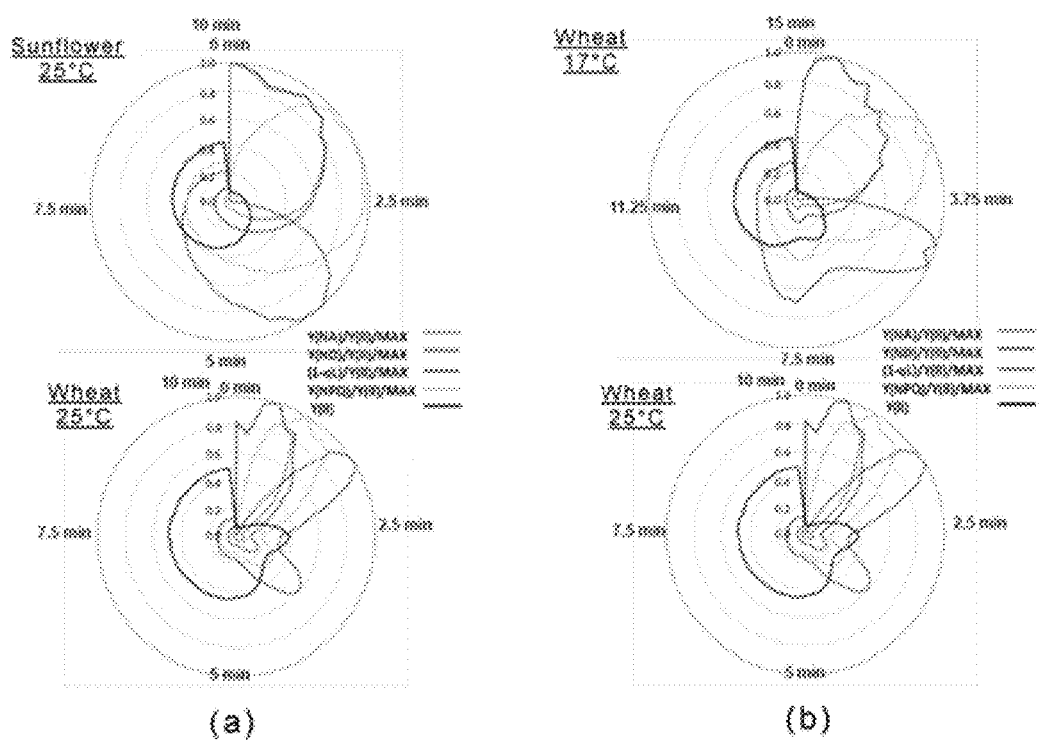
FIG. 34 shows an example of measurement results acquired by utilizing the temperature adjustment unit in the present embodiment.

For example, in a case of comparing measurement results of sunflower and wheat as shown in FIG. 34(a), it will be difficult to grasp characteristics when measurement is performed at the same temperature (25° C.) because movement of the light induction phenomenon is faster in wheat than in sunflower.

Hence, performing temperature adjustment control upon measuring wheat as shown in FIG. 34(b) (17° C. in FIG.

34(*b*)) can make movement of analytic parameters slower to facilitate grasp of characteristics of wheat (the oxygen reaction rate can be forcibly slowed to specify and diagnose nutritional deficiency of wheat).

Although the present embodiment performs the environmental stress diagnosis for plants by utilizing measurement information about the photosystem II or the photosystem I, the measurement information and analysis results acquired in the environmental stress diagnosis device 10 according to the present embodiment, for example, can also be utilized for other applications such as a growth diagnosis and breeding of plants.

In addition, although the environmental stress diagnosis device according to the present embodiment has a structure in which a plant sample is put into the sealed chamber, non-destructive, time-dependent monitoring can also be achieved by adopting a structure of performing measurement with a leaf inserted, for example (by performing measurement without cutting off the leaf). In addition, the present embodiment also enables a plurality of samples to be collectively gauged at the same time by utilizing a plurality of environmental stress diagnosis devices (utilizing a portable terminal, a data server, and the like as well).

REFERENCE SIGNS LIST

10: Environmental stress diagnosis device
12: Measurement light source
14: Induction light source
16: Sealed chamber
18: Transmitted light detector
20: Control unit
20*a*: Analysis circuit
20*b*: Control circuit
22: Oxygen concentration detector
24: Environment sensor
30*a*: Exhaled air introduction port
30*b*: Air output port
40: Fluorescence detector
42: Temperature adjustment unit
ML: Measurement light
ML1: First measurement light
ML2: Second measurement light
ML3: Composite rectangular wave measurement light
PL: Photosynthesis inducing light
FR: First photosynthesis inducing light
AL: Second photosynthesis inducing light
TL: Composite rectangular wave transmitted light

The invention claimed is:

1. An environmental stress diagnosis device that diagnoses an environmental stress state of a plant sample, comprising:
a measurement light source that radiates a measurement light to the plant sample; an induction light source that radiates a photosynthesis inducing light to the plant sample; a sealed chamber that stores the plant sample and allows entry of the measurement light and the photosynthesis inducing light; a transmitted light detector that detects the measurement light transmitted through the plant sample as a transmitted light, and a control unit that receives the transmitted light detected by the transmitted light detector as a measurement signal, wherein
the measurement light source outputs two types of a first measurement light and a second measurement light having different wavelengths,
the induction light source outputs two types of a first photosynthesis inducing light and a second photosynthesis inducing light having different wavelengths,
the control unit has an analysis circuit that analyzes a detection result acquired by the transmitted light detector, and a control circuit that controls the measurement light source and the induction light source to correspond to the plant sample,
the control circuit adjusts and controls the first measurement light and the second measurement light to have different output amplitudes, and controls the measurement light source such that the first measurement light and the second measurement light become opposite-phase rectangular waves,
the control circuit controls the measurement light source to output the first measurement light and the second measurement light in synchronization to form the first measurement light and the second measurement light into a quasi-single composite rectangular wave measurement light of 5 kHz to 30 kHz including a DC component,
the transmitted light detector detects the composite rectangular wave measurement light transmitted through the plant sample as a composite rectangular wave transmitted light,
the analysis circuit calculates a light absorption difference between the first measurement light and the second measurement light transmitted through the plant sample by utilizing the composite rectangular wave transmitted light, and calculates Y(ND) which is a state in which P700 in photosystem I has been oxidized in photosynthesis as a ROS marker which is a reactive oxygen species suppression index for a plant by utilizing the light absorption difference, and
the analysis circuit diagnoses the environmental stress state of the plant sample by utilizing the ROS marker.

2. The environmental stress diagnosis device according to claim 1, wherein:
the environmental stress diagnosis devise is equipped with a communication unit for network connection, and the environmental stress diagnosis device is network-connected to a communication terminal via the communication unit,
the communication terminal is utilized for operating the environmental stress diagnosis device, and displays the ROS marker as a measurement result and an environmental stress diagnosis result, and
the communication terminal is network-connected to a data server in which environmental stress diagnosis data is accumulated, and compares the environmental stress diagnosis data and the ROS marker to diagnose the environmental stress state of the plant sample.

3. The environmental stress diagnosis device according to claim 1, wherein;
the control circuit synchronizes the first measurement light and the second measurement light that are output from the measurement light source by PWM control,
the control circuit compares falling timings of rectangular waves in the first measurement light and the second measurement light with a reference signal waveform as a command frequency, and
in a case in which the falling timings in the first measurement light and the second measurement light lose synchronization due to outputs from the measurement light source, the control circuit adjusts the falling timings in a unit of 0.25 µs to maintain synchronization.

4. The environmental stress diagnosis device according to claim 1, wherein;

the induction light source performs stationary radiation with the first photosynthesis inducing light as continuous radiation, performs pulse radiation with the first photosynthesis inducing light as higher power radiation than the stationary radiation without providing a pausing period after the stationary radiation, thereafter provides a pausing period, performs stationary radiation with the second photosynthesis inducing light, and performs pulse radiation with the second photosynthesis inducing light without providing a pausing period after the stationary radiation, and a radiation time of the pulse radiation is 1 ms to 300 ms.

5. The environmental stress diagnosis device according to claim 1, wherein;

the sealed chamber is equipped with an oxygen concentration detector that measures an oxygen production rate of the plant sample inside the sealed chamber, and the analysis circuit diagnoses the environmental stress state of the plant sample by utilizing a correlation between the ROS marker and the oxygen production rate.

6. The environmental stress diagnosis device according to claim 5, wherein:

the sealed chamber is equipped with all or any of a temperature sensor, a humidity sensor, and an atmospheric pressure sensor as an environment sensor, and the analysis circuit performs correction processing on the oxygen production rate detected by the oxygen concentration detector based on a detection result acquired by the environment sensor.

7. The environmental stress diagnosis device according to claim 5, wherein;

the oxygen concentration detector is a galvanic cell type oxygen concentration detector.

8. The environmental stress diagnosis device according to claim 1, wherein;

the sealed chamber is equipped with an exhaled air introduction port for externally introducing exhaled air and an air output port for replacing air inside the sealed chamber.

9. The environmental stress diagnosis device according to claim 1, wherein;

the environmental stress diagnosis device is further equipped with a fluorescence detector that detects chlorophyll fluorescence from the plant sample, the analysis circuit calculates, from a chlorophyll fluorescence detection result acquired by the fluorescence detector, Y(II) as a photosynthesis rate, Y(NPQ) as light energy that cannot be utilized for photosynthesis, Y(NO) as fundamental heat dissipation performance in photosystem II, and 1-pL as a plastoquinone reduction rate, the analysis circuit calculates Y(I) which is a ground state of P700 and Y(NA) which is a state in which P700 is absorbing light energy by utilizing the light absorption difference, and the analysis circuit diagnoses a mineral nutrient deficient state in the plant sample by utilizing all or any of the Y(II), Y(NPQ), Y(NO), 1-pL, Y(I), Y(NA), and Y(ND) which is the ROS marker.

10. The environmental stress diagnosis device according to claim 9, wherein:

the analysis circuit creates a sample diagnosis graph in which an elapse of time is expressed circularly and values acquired by dividing Y(I), Y(ND), and Y(NA) by Y(II) are plotted, and the analysis circuit compares a basic diagnosis graph showing a plant in which mineral nutrients are controlled and the sample diagnosis graph to diagnose a deficient state of all or any of N, P, K, S, Mg, Ca, B, Zn, Mo, Cu, Fe, and Mn which are essential nutrients in the plant sample.

11. The environmental stress diagnosis device according to claim 9, wherein;

the sealed chamber is equipped with a temperature adjustment unit for controlling a temperature of the plant sample disposed inside the sealed chamber.

12. An environmental stress diagnosis method for a plant, comprising the steps of:

storing a plant sample in a sealed chamber, and by a control circuit, adjusting a first measurement light and a second measurement light that are output from a measurement light source and adjusting a first photosynthesis inducing light and a second photosynthesis inducing light to be output from an induction light source;

controlling the measurement light source by the control circuit such that the second measurement light has higher power than the first measurement light and the first measurement light and the second measurement light become opposite-phase rectangular waves, controlling the measurement light source by the control circuit such that the first measurement light and the second measurement light are output in synchronization to form the first measurement light and the second measurement light into a quasi-single composite rectangular wave measurement light of 5 kHz to 30 kHz including a DC component, and radiating the composite rectangular wave measurement light together with the first photosynthesis inducing light and the second photosynthesis inducing light to the plant sample;

detecting, by a transmitted light detector, the composite rectangular wave measurement light transmitted through the plant sample as a composite rectangular wave transmitted light having a single frequency;

calculating, by an analysis circuit, a light absorption difference between the first measurement light and the second measurement light transmitted through the plant sample by utilizing the composite rectangular wave transmitted light, and calculating, by the analysis circuit, Y(ND) which is a state in which P700 in photosystem I has been oxidized in photosynthesis as a ROS marker which is a reactive oxygen species suppression index for a plant by utilizing the light absorption difference; and diagnosing an environmental stress state of the plant by utilizing the ROS marker.

* * * * *